(12) United States Patent
Rice et al.

(10) Patent No.: US 7,794,942 B2
(45) Date of Patent: **\*Sep. 14, 2010**

(54) CELL LINES PERMISSIVE FOR HCV REPLICATION

(75) Inventors: Charles M. Rice, New York, NY (US);
Keril J. Blight, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 11/960,391

(22) Filed: Dec. 19, 2007

(65) Prior Publication Data

US 2008/0213750 A1 Sep. 4, 2008

Related U.S. Application Data

(63) Continuation of application No. 10/276,051, filed as application No. PCT/US01/16822 on May 23, 2001, now Pat. No. 7,338,759, which is a continuation-in-part of application No. 09/576,989, filed on May 23, 2000, now Pat. No. 7,049,428, which is a continuation-in-part of application No. 09/034,756, filed on Mar. 4, 1998, now Pat. No. 6,392,028, which is a continuation of application No. 08/811,566, filed on Mar. 4, 1997, now Pat. No. 6,127,116.

(60) Provisional application No. 60/039,843, filed on Mar. 4, 1997.

(51) Int. Cl.
| C12Q 1/68 | (2006.01) |
| C12N 15/00 | (2006.01) |
| C12N 5/10 | (2006.01) |
| C12N 15/51 | (2006.01) |

(52) U.S. Cl. ........................... 435/6; 435/455; 435/325; 435/320.1

(58) Field of Classification Search ...................... None
See application file for complete search history.

(56) References Cited

U.S. PATENT DOCUMENTS

7,455,969 B2 * 11/2008 Rice et al. ...................... 435/6
2004/0067486 A1 4/2004 Paonessa et al.

FOREIGN PATENT DOCUMENTS

WO    WO 02/059321    * 8/2002

OTHER PUBLICATIONS

Blight et al., "Highly Permissive Cell Lines for Subgenomic and Genomic Hepatitis C Virus RNA Replication," Journal of Virology, vol. 76 No. 24, pp. 13001-13014, Dec. 2002.*

(Continued)

*Primary Examiner*—Zachariah Lucas
(74) *Attorney, Agent, or Firm*—Thompson Coburn LLP; Charles P. Romano

(57) ABSTRACT

HCV variants are described. The variants include polynucleotides comprising non-naturally occurring HCV sequences and HCV variants that have a transfection efficiency and ability to survive subpassage greater than HCV that have wild-type polyprotein coding regions. Expression vectors comprising the above polynucleotides and HCV variants are also described, as are the provision of cells and host cells comprising the expression vectors. Methods for identifying a cell line that is permissive for infection with HCV are also provided, as are vaccines comprising the above polynucleotides in a pharmaceutically acceptable carrier. Additionally, methods for inducing immunoprotection to HCV in a primate are described, as are methods for testing a compound for inhibiting HCV replication.

10 Claims, 10 Drawing Sheets

OTHER PUBLICATIONS

Blight et al., "Efficient Initiation of HCV RNA Replication in Cell Culture," Science, vol. 290 No. 5498, pp. 1972-1974 (Dec. 2000).*
European Communication for Corresponding European Application No. 03789775.8 dated Mar. 23, 2007.
European Communication for Corresponding European Application No. 03789775.8 dated Apr. 24, 2006.
Lanford et al., "Advances in Model Systems for Hepatitis C Virus Research," Virology, Feb. 2002, pp. 1-9, vol. 293.
Lindenbach et al., "Cell Culture-Grown Hepatitis C Virus is Infectious In Vivo and Can Be Recultured In Vitro," Proceedings of the National Academy of Sciences, USA, Mar. 2006, pp. 3805-3809, vol. 103, No. 10.
Sheehy et al., "In Vitro Replication Models for the Hepatitis C Virus," Journal of Viral Hepatitis, Jan. 2007, pp. 2-10 col. No. 1.
Raymond T. Chung, "Hepatitis C Virus Replication is Directly Inhibited by IFN-alpha in a Full-Length Binary Expression System", Proceedings of the National Academy of Sciences, Aug. 2001, pp. 9847-9852, vol. 98, No. 17, USA.
Ralf Bartenschlager, "Replication of the Hepatitis C Virus in Cell Culture", Antiviral Research, Oct. 2003, pp. 91-102, vol. 60, No. 2, Elsevier.
Krieger et al., "Enhancement of Hepatitis C Virus RNA Replication by Cell Culture-Adaptive Mutations", J Virol., 2001, pp. 14-24, vol. 75:46.
Murray et al., "Persistent Replication of Hepatitis C Virus Replicons Expressing the Beta-Lactamase Reporter in Subpopulations of Highly Permissive Huh7 Cells", J Virol., 2003, pp. 2928-2935, vol. 75:46.
Japanese Office Action for Corresponding Japanese Application No. 2006-339705, dated Apr. 4, 2007.
Mizutani et al., "Characterization of Hepatitis C Virus Replication in Cloned Cells Obtained from a Human T-cell : Leukemia Virus Type 1-Infected Cell Line", MT-2 J. Virol., 1995, pp. 7219-7223, vol. 70.
Kato et al., "Establishment of a Hepatitis C Virus Subgenomic Replicon Derived from Human Hepatocytes Infected in Vitro", Biochemical and Biophysical Research Communications, pp. 756-766, vol. 306, Issue 3.

* cited by examiner

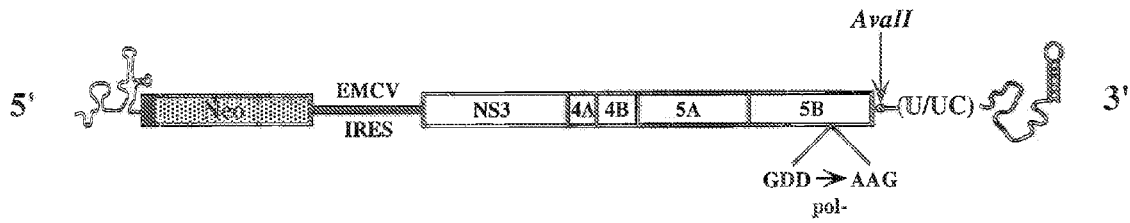

- DNase digest RNA transcripts
- Electroporate RNA into Huh7 cells
- G418-resistant colonies were generated at low frequency
- 28 colonies were picked & 90% of these could be passaged
- No colonies observed for the replicon RNA containing an inactive RDRP

| Clone | Copy number/cell | Cytoplasmic NS3 | Growth Rate |
|---|---|---|---|
| I | >1000 | Yes | Fast |
| II | ~1000-5000 | Yes | Fast |
| IV | ND | Yes | Fast |
| V | 500 | ND | Moderate |
| VI | ~1000 | Yes | Fast |
| VII | >800 | Yes | Fast |
| Clone E | <400 | No | Very slow |

Figure 4

A.
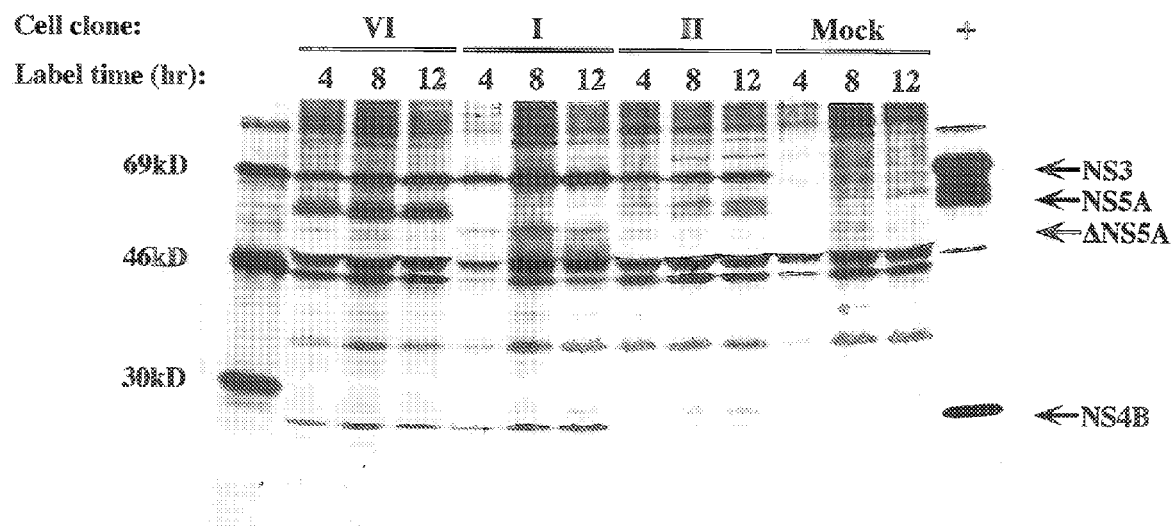
B.
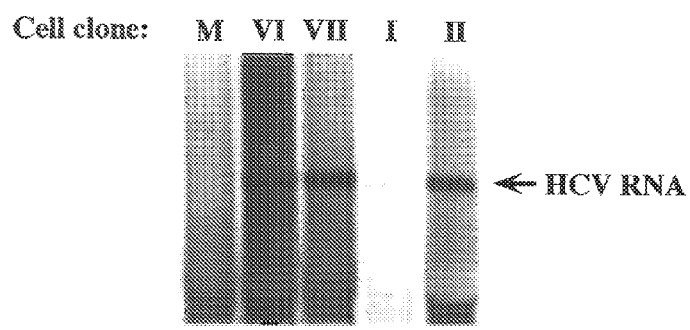
Figure 5

CELL LINES PERMISSIVE FOR HCV REPLICATION

CROSS-REFERENCE TO RELATED APPLICATIONS

This application is a continuation application of U.S. patent application Ser. No. 10/276,051, filed on Apr. 1, 2003, now U.S. Pat. No. 7,338,759, which is a national stage application of PCT Patent Application No. PCT/US2001/016822, filed May 23, 2001, which is a continuation-in-part of U.S. patent application Ser. No. 09/576,989, filed May 23, 2000, now U.S. Pat. No. 7,049,428, which is a continuation-in-part of U.S. patent application Ser. No. 09/034,756, filed Mar. 4, 1998, now U.S. Pat. No. 6,392,028, which is a continuation of U.S. patent application Ser. No. 08/811,566, filed Mar. 4, 1997, now U.S. Pat. No. 6,127,116, and which claims priority to U.S. Provisional Application No. 60/039,843, filed Mar. 4, 1997.

REFERENCE TO GOVERNMENT GRANT

This invention was made with government support under Public Health Service Grants CA 57973 and AI 40034. The government has certain rights in this invention.

BACKGROUND OF THE INVENTION

1) Field of the Invention

The invention relates to materials and methodologies relating to the production and use of hepatitis C virus (HCV) variants. More specifically, HCV variants are provided that are useful for diagnostic, therapeutic, vaccines and other uses.

2) Description of the Related Art

Brief General Overview of Hepatitis C Virus

After the development of diagnostic tests for hepatitis A virus and hepatitis B virus, an additional agent, which could be experimentally transmitted to chimpanzees [Alter et al., *Lancet* 1, 459-463 (1978); Hollinger et al., *Intervirology* 10, 60-68 (1978); Tabor et al., *Lancet* 1, 463-466 (1978)], became recognized as the major cause of transfusion-acquired hepatitis. cDNA clones corresponding to the causative non-A non-B (NANB) hepatitis agent, called hepatitis C virus (HCV), were reported in 1989 [Choo et al., *Science* 244, 359-362 (1989)]. This breakthrough has led to rapid advances in diagnostics, and in our understanding of the epidemiology, pathogenesis and molecular virology of HCV (For review, see Houghton et al., *Curr Stud Hematol Blood Transfus* 61, 1-11 (1994); Houghton (1996), pp. 1035-1058 in FIELDS VIROLOGY, Fields et al., Eds., Raven Press, Philadelphia; Major et al., *Hepatology* 25, 1527-1538 (1997); Reed and Rice, pp. 1-37 in HEPATITIS C VIRUS, Reesink, Ed., Karger, Basel; Hagedorn and Rice (1999), THE HEPATITIS C VIRUSES, Springer, Berlin). Evidence of HCV infection is found throughout the world, and the prevalence of HCV-specific antibodies ranges from 0.4-2% in most countries to more than 14% in Egypt [Hibbs et al., *J. Inf. Dis.* 168, 789-790 (1993)]. Besides transmission via blood or blood products, or less frequently by sexual and congenital routes, sporadic cases, not associated with known risk factors, occur and account for more than 40% of HCV cases [Alter et al., *J. Am. Med. Assoc.* 264, 2231-2235 (1990); Mast and Alter, *Semin. Virol.* 4, 273-283 (1993)]. Infections are usually chronic [Alter et al., *N. Eng. J. Med.* 327, 1899-1905 (1992)], and clinical outcomes range from an inapparent carrier state to acute hepatitis, chronic active hepatitis, and cirrhosis which is strongly associated with the development of hepatocellular carcinoma.

Although interferon (IFN)-α has been shown to be useful for the treatment of a minority of patients with chronic HCV infections [Davis et al., *N. Engl. J. Med.* 321, 1501-1506 (1989); DiBisceglie et al., *New Engl. J. Med.* 321, 1506-1510 (1989)] and subunit vaccines show some promise in the chimpanzee model [Choo et al., *Proc. Natl. Acad. Sci. USA* 91, 1294-1298 (1994)], future efforts are needed to develop more effective therapies and vaccines (See, e.g., Tsambiras et al., 1999, Hepatitis C: Hope on the Horizon, Hepatitis C Symposium of 37$^{th}$ Annual Meeting of the Infectious Diseases Society of America, reviewed at http://www.medscape.com/medscape/cno/1999/IDSA/Story.cfin?story_id=913). The considerable diversity observed among different HCV isolates [for review, see Bukh et al., *Sem. Liver Dis.* 15, 41-63 (1995); Fanning et al., 2000, *Medscape Gastroenterology* 2:mgi6558.fann], the emergence of genetic variants in chronically infected individuals [Enomoto et al., *J. Hepatol.* 17, 415-416 (1993); Hijikata et al., *Biochem. Biophys. Res. Comm.* 175, 220-228 (1991); Kato et al., *Biochem. Biophys. Res. Comm.* 189, 119-127 (1992); Kato et al., *J. Virol.* 67, 3923-3930 (1993); Kurosaki et al., *Hepatology* 18, 1293-1299 (1993); Lesniewski et al., *J. Med. Virol.* 40, 150-156 (1993); Ogata et al., *Proc. Natl. Acad. Sci. USA* 88, 3392-3396 (1991); Weiner et al., *Virology* 180, 842-848 (1991); Weiner et al., *Proc. Natl. Acad. Sci. USA* 89, 3468-3472 (1992)], and the lack of protective immunity elicited after HCV infection [Farci et al., *Science* 258, 135-140 (1992); Prince et al., *J. Infect. Dis.* 165, 438-443 (1992)] present major challenges towards these goals.

Molecular Biology of HCV

Classification. Based on its genome structure and virion properties, HCV has been classified as a separate genus in the flavivirus family, which includes two other genera: the flaviviruses (e.g., yellow fever (YF) virus) and the animal pestiviruses (e.g., bovine viral diarrhea virus (BVDV) and classical swine fever virus (CSFV)) [Francki et al., *Arch. Virol.* Suppl. 2, 223 (1991)]. All members of this family have enveloped virions that contain a positive-strand RNA genome encoding all known virus-specific proteins via translation of a single long open reading frame (ORF).

Structure and physical properties of the virion. Studies on the structure and physical properties of the HCV virion have been hampered by the lack of a cell culture system able to support efficient virus replication and the typically low titers of infectious virus present in serum. The size of infectious virus, based on filtration experiments, is between 30-80 nm [Bradley et al., *Gastroenterology* 88, 773-779 (1985); He et al., *J. Infect. Dis.* 156, 636-640 (1987); Yuasa et al., *J. Gen. Virol.* 72, 2021-2024 (1991)]. Initial measurements of the buoyant density of infectious material in sucrose yielded a range of values, with the majority present in a low density pool of <1.1 g/ml [Bradley et al., *J. Med. Virol.* 34, 206-208 (1991)]. Subsequent studies have used RT/PCR to detect HCV-specific RNA as an indirect measure of potentially infectious virus present in sera from chronically infected humans or experimentally infected chimpanzees. From these studies, it has become increasingly clear that considerable heterogeneity exists between different clinical samples, and that many factors can affect the behavior of particles containing HCV RNA [Hijikata et al., *J. Virol.* 67, 1953-1958 (1993); Thomssen et al., *Med. Microbiol. Immunol.* 181, 293-300 (1992)]. Such factors include association with immunoglobulins [Hijikata et al., (1993) supra] or low density lipoprotein [Thomssen et al., 1992, supra; Thomssen et al., *Med. Microbiol. Immunol.* 182, 329-334 (1993)]. In highly infectious acute phase chimpanzee serum, HCV-specific RNA is usually detected in fractions of low buoyant density (1.03-1.1 g/ml) [Carrick et al., *J. Virol. Meth.* 39, 279-289 (1992); Hijikata et al., (1993) supra]. In other samples, the presence of HCV antibodies and formation of immune complexes correlate with particles of higher density and lower infectivity [Hijikata et al., (1993) supra]. Treatment of particles with chloroform, which destroys infectivity [Bradley et al., *J. Infect. Dis.* 148, 254-265 (1983); Feinstone et al., *Infect. Immun.* 41, 816-821 (1983)], or with nonionic detergents, produced RNA containing particles of higher density (1.17-1.25 g/ml) believed to represent HCV nucleocapsids [Hijikata et al., (1993) supra; Kanto et al., *Hepatology* 19, 296-302 (1994); Miyamoto et al., *J. Gen Virol.* 73,715-718 (1992)].

There have been reports of negative-sense HCV-specific RNAs in sera and plasma [see Fong et al., *Journal of Clinical Investigation* 88:1058-60 (1991)]. However, it seems unlikely that such RNAs are essential components of infectious particles since some sera with high infectivity can have low or undetectable levels of negative-strand RNA [Shimizu et al., *Proc. Natl. Acad. Sci. USA* 90: 6037-6041 (1993)].

The virion protein composition has not been rigorously determined, but HCV structural proteins include a basic C protein and two membrane glycoproteins, E1 and E2.

HCV replication. Early events in HCV replication are poorly understood. A hepatocyte receptor may be CD81, which binds the E2 envelope glycoprotein (Peleri et al., 1998, *Science* 282:938-41). The association of some HCV particles with beta-lipoprotein and immunoglobulins raises the possibility that these host molecules may modulate virus uptake and tissue tropism.

Studies examining HCV replication have been largely restricted to human patients or experimentally inoculated chimpanzees. In the chimpanzee model, HCV RNA is detected in the serum as early as three days post-inoculation and persists through the peak of serum alanine aminotransferase (ALT) levels (an indicator of liver damage) [Shimizu et al., *Proc. Natl. Acad. Sci. USA* 87: 6441-6444 (1990)]. The onset of viremia is followed by the appearance of indirect hallmarks of HCV infection of the liver. These include the appearance of a cytoplasmic antigen [Shimizu et al., (1990) supra] and ultrastructural changes in hepatocytes such as the formation of microtubular aggregates for which HCV previously was referred to as the chloroform-sensitive "tubule forming agent" or "TFA" [reviewed by Bradley, *Prog. Med. Virol.* 37: 101-135 (1990)]. As shown by the appearance of viral antigens [Blight et al., *Amer. J. Path.* 143: 1568-1573 (1993); Hiramatsu et al., *Hepatology* 16: 306-311 (1992); Krawczynski et al., *Gastroenterology* 103: 622-629 (1992); Yamada et al., *Digest. Dis. Sci.* 38: 882-887 (1993)] and the detection of positive and negative sense RNAs [Fong et al., (1991) supra; Gunji et al., *Arch. Virol.* 134: 293-302 (1994); Haruna et al., *J. Hepatol.* 18: 96-100 (1993); Lamas et al., *J. Hepatol.* 16: 219-223 (1992); Nouri Aria et al., *J. Clin. Inves.* 91: 2226-34 (1993); Sherker et al., *J. Med. Virol.* 39: 91-96 (1993); Takehara et al., *Hepatology* 15: 387-390 (1992); Tanaka et al., *Liver* 13: 203-208 (1993)], hepatocytes appear to be a major site of HCV replication, particularly during acute infection [Negro et al., *Proc. Natl. Acad. Sci. USA* 89: 2247-2251 (1992)]. In later stages of HCV infection the appearance of HCV-specific antibodies, the persistence or resolution of viremia, and the severity of liver disease, vary greatly both in the chimpanzee model and in human patients (Fanning et al., supra). Although some liver damage may occur as a direct consequence of HCV infection and cytopathogenicity, the emerging consensus is that host immune responses, in particular virus-specific cytotoxic T lymphocytes, may play a more dominant role in mediating cellular damage.

It has been speculated that HCV may also replicate in extra-hepatic reservoir(s). In some cases, RT/PCR or in situ hybridization has shown an association of HCV RNA with peripheral blood mononuclear cells including T-cells, B-cells, and monocytes [reviewed in Blight and Gowans, *Viral Hepatitis Rev.* 1: 143-155 (1995)]. Such tissue tropism could be relevant to the establishment of chronic infections and might also play a role in the association between HCV infection and certain immunological abnormalities such as mixed cryoglobulinemia [reviewed by Ferri et al., *Eur. J. Clin. Invest.* 23: 399-405 (1993)], glomerulonephritis, and rare non-Hodgkin's B-lymphomas [Ferri et al., (1993) supra; Kagawa et al., *Lancet* 341: 316-317 (1993)]. However, the detection of circulating negative strand RNA in serum, the difficulty in obtaining truly strand-specific RT/PCR [Gunji et al., (1994) supra], and the low numbers of apparently infected cells have made it difficult to obtain unambiguous evidence for replication in these tissues in vivo.

Genome structure. Full-length or nearly full-length genome sequences of numerous HCV isolates have been reported [see, e.g., Lin et al., *J. Virol.* 68: 5063-5073 (1994a); Okamoto et al., *J. Gen. Virol.* 75: 629-635 (1994); Sakamoto et al., *J. Gen. Virol.* 75: 1761-1768 (1994); Trowbridge et al, *Arch Virol.* 143:501-511 (1998); Chamberlain et al, *J. Gen. Virol.* 78:1341-1347 (1997); and citations within Davis, *Am. J. Med.* 27:21S-26S]. HCV genome RNAs are ~9.6 kilobases (kb) in length (FIG. 1) and consist of a 5' nontranslated region (5' NTR), a polyprotein coding region consisting of a single long open reading frame (ORF), and a 3' NTR. The 5' NTR is 341-344 bases long and highly conserved. The length of the long ORF varies slightly among isolates, encoding polyproteins of about 3010 to about 3033 amino acids.

The 3' NTR can be divided into three domains. The first (most 5') domain shows considerable diversity both in composition and length (28-42 bases). Recent work by Yanagi et al. [*Proc. Natl. Acad. Sci. USA* 96:2291-2295(1999)] demonstrate that this region is not necessary for virus replication. The second domain is consists of a variable length polypyrimidine region of poly(A) (in at least HCV-1, type 1a [Han et al., *Proc. Natl. Acad. Sci. USA* 88:1711-1715 (1991)]) or poly(U-UC) (see Chen et al., *Virology* 188:102-113 (1992); Okamoto et al., *J. Gen. Virol.* 72:2697-2704 (1991); Tokita et al., *J. Gen. Virol.* 66:1476-83 (1994)]. The third domain, at the extreme 3' end of the genome, is a highly conserved, novel RNA element of about 98 nucleotides, which is necessary for efficient initiation of viral RNA replication [see, e.g., U.S. Pat. No. 5,874,565 and U.S. patent application Ser. No. 08/811,566 (Now U.S. Pat. No. 6,127,116); Kolykhalov et al., *J. Virol.* 70: 3363-3371 (1996); Tanaka et al., *Biochem. Biophys. Res. Comm.* 215: 744-749 (1996); Tanaka et al., *J. Virol.* 70:3307-12 (1996); Yamada et al., *Virology* 223:255-261 (1996); Cheng et al. *J. Virol.* 73:7044-7049]. This domain and the polypyrimidine regions appear to be critical for infectivity in vivo [Yanagi et al., *Proc. Natl. Acad. Sci. USA* 96:2291-2295 (1999)].

Translation and proteolytic processing. The highly conserved 5' NTR sequence contains multiple short AUG-initiated ORFs and shows significant homology with the 5' NTR region of pestiviruses [Bukh et al., *Proc. Natl. Acad. Sci. USA* 89: 4942-4946 (1992); Han et al., (1991) supra]. A series of stem-loop structures that interact with host factors are present. These structures interact with host factors to initiate polyprotein synthesis through an internal ribosome entry site (IRES) allowing efficient translation initiation at the first AUG of the long ORF [Honda et al., *J. Virol* 73:4941-4951 (1999); Tang et al., *J. Virol.* 73:2359-2364(1999); Psaridi et al., *FEBS Lett.* 453:49-53 (1999)]. Some of the predicted features of the HCV and pestivirus IRES elements are similar to one another [Brown et al., (1992) supra]. The ability of this element to fimction as an IRES suggests that HCV genome RNAs may lack a 5' cap structure.

The organization and processing of the HCV polyprotein (FIG. 1) appears to be most similar to that of the pestiviruses. At least 10 polypeptides have been identified and the order of these cleavage products in the polyprotein is NH2-C-E1-E2-p7-NS2-NS3-NS4A-NS4B—NS5A-NS5B—COOH. As shown in FIG. 1, proteolytic processing is mediated by host signal peptidase and two HCV-encoded proteinases, the NS2-3 autoproteinase and the NS3-4A serine proteinase [see Rice, In "Fields Virology" (B. N. Fields, D. M. Knipe and P. M. Howley, Eds.), Vol. pp. 931-960. Raven Press, New York (1996); Shimotohno et al., *J. Hepatol.* 22: 87-92 (1995) for reviews]. C is a basic protein that serves as the viral core or capsid protein; E1 and E2 are virion envelope glycoproteins; p7 is a hydrophobic protein of unknown function that is inefficiently cleaved from the E2 glycoprotein [Lin et al., (1994a) supra; Mizushima et al., *J. Virol.* 68: 6215-6222 (1994); Selby et al., *Virology* 204: 114-122 (1994)]. NS2-NS5B are nonstructural (NS) proteins which function in viral RNA replication complexes. Their functions have been identified as follows: NS2 is a metalloprotease; NS3 is a protease/helicase that contains motifs characteristic of RNA helicases and that has been shown to possess an RNA-stimulated NTPase activity [Suzich et al., *J. Virol.* 67, 6152-6158 (1993)]; NS4A is a co-factor for NS3; NS4B is of unknown function; NS5A interacts with cellular factors to transcriptionally modulate cellular genes and promote cell growth [Ghosh et al., *J. Biol. Chem.* 275:7184-7188] and provide IFNα resistance; and NS5B is a replicase that contains the GDD motif characteristic of the RNA-dependent RNA polymerases of other positive-strand RNA viruses.

Virion assembly and release. This process has not been examined directly, but the lack of complex glycans, the ER localization of expressed HCV glycoproteins [Dubuisson et al., *J. Virol.* 68: 6147-6160 (1994); Ralston et al., *J. Virol.* 67: 6753-6761 (1993)] and the absence of these proteins on the cell surface [Dubuisson et al., (1994) supra; Spaete et al., *Virology* 188: 819-830 (1992)] suggest that initial virion morphogenesis may occur by budding into intracellular vesicles. Thus far, efficient particle formation and release has not been observed in transient expression assays, suggesting that essential viral or host factors are absent or blocked. HCV virion formation and release may be inefficient, since a substantial fraction of the virus remains cell-associated, as found for the pestiviruses. Extracellular HCV particles partially purified from human plasma contain complex N-linked glycans, although these carbohydrate moieties were not shown to be specifically associated with E1 or E2 [Sato et al., *Virology* 196: 354-357 (1993)]. Complex glycans associated with glycoproteins on released virions would suggest transit through the trans-Golgi and movement of virions through the host secretory pathway. If this is correct, intracellular sequestration of HCV glycoproteins and virion formation might then play a role in the establishment of chronic infections by minimizing immune surveillance and preventing lysis of virus-infected cells via antibody and complement.

Genetic variability. As for all positive-strand RNA viruses, the RNA-dependent RNA polymerase of HCV (NS5B) is believed to lack a 3'-5' exonuclease proofreading activity for removal of misincorporated bases. Replication is therefore error-prone, leading to a "quasi-species" virus population consisting of a large number of variants [Martell et al., *J. Virol.* 66: 3225-3229 (1992); Martell et al., *J. Virol.* 68: 3425-3436 (1994)]. This variability is apparent at multiple levels. First, in a chronically infected individual, changes in the virus population occur over time [Ogata et al., (1991) supra; Okamoto et al., *Virology* 190: 894-899 (1992)]; and these changes may have important consequences for disease. A particularly interesting example is the N-terminal 30 residue segment of the E2 glycoprotein, which exhibits a much higher degree of variability than the rest of the polyprotein [for examples, see Higashi et al., *Virology* 197, 659-668. 1993; Hijikata et al., (1991) supra; Weiner et al., (1991) supra]. There is accumulating evidence that this hypervariable region, called hypervariable region 1 (HVR1), perhaps analogous to the V3 domain of HIV-1 gp120, may be under immune selection by circulating HCV-specific antibodies [Kato et al., (1993) supra; Taniguchi et al., *Virology* 195: 297-301 (1993); Weiner et al., (1992) supra. In this model, antibodies directed against this portion of E2 may contribute to virus neutralization and thus drive the selection of variants with substitutions that permit escape from neutralization. This plasticity suggests that a specific amino acid sequence in the E2 hypervariable region is not essential for other functions of the protein such as virion attachment, penetration, or assembly. Genetic evolution of HVR1 within the first 4 months of infection has been correlated with the ability of a particular strain of the virus to cause chronic infection [Farci et al., *Science* 288:339-344 (2000)].

Genetic variability may also contribute to the spectrum of different responses observed after IFN-α treatment of chronically infected patients. Diminished serum ALT levels and improved liver histology, which usually correlates with a decrease in the level of circulating HCV RNA, is seen in ~40% of those treated [Greiser-Wilke et al., *J. Gen. Virol.* 72: 2015-2019 (1991)]. After treatment, approximately 70% of the responders relapse. In some cases, after a transient loss of circulating viral RNA, renewed viremia is observed during or after the course of treatment. While this might suggest the existence or generation of IFN-resistant HCV genotypes or variants, further work is needed to determine the relative contributions of virus genotype and host-specific differences in immune response.

Sequence comparisons of different HCV isolates around the world have also revealed enormous genetic diversity [reviewed in Bukh et al., (1995) supra]. Because of the lack of biologically relevant serological assays such as cross-neutralization tests, HCV types (designated by numbers), subtypes (designated by letters), and isolates are currently grouped on the basis of nucleotide or amino acid sequence similarity. Worldwide, HCV has been classified into six major genotypes and more than 50 subtypes [Purcell, *Hepatology* 26: 11S-14S (1997)]. Those of greatest importance in the U.S. are genotype 1, subtypes 1a and 1b (see below and Bukh et al., (1995) supra for a discussion of genotype prevalence and distribution). Amino acid sequence similarity between the most divergent genotypes can be a little as ~50%, depending upon the protein being compared. This diversity has important biological implications, particularly for diagnosis, vaccine design, and therapy.

HCV RKA replication. By analogy with other flaviviruses, replication of the positive-sense HCV virion RNA is thought to occur via a minus-strand intermediate. This strategy can be described briefly as follows: (i) uncoating of the incoming virus particle releases the genomic plus-strand, which is translated to produce a single long polyprotein that is probably processed co- and post-translationally to produce individual structural and nonstructural proteins; (ii) the nonstructural proteins form a replication complex that utilizes the virion RNA as template for the synthesis of minus strands; (iii) these minus strands in turn serve as templates for synthesis of plus strands, which can be used for additional translation of viral protein, minus strand synthesis, or packaging into progeny virions. Very few details about HCV replication process are available, due to the lack of a good experimental system for virus propagation. Detailed analyses of authentic HCV replication and other steps in the viral life cycle would be greatly facilitated by the development of an efficient system for HCV replication in cell culture.

Many attempts have been made to infect cultured cells with serum collected from HCV-infected individuals, and low levels of replication have been reported in a number of cells types infected by this method, including B-cell [Bertolini et al., *Res. Virol.* 144: 281-285 (1993); Nakajima et al., *J. Virol.* 70: 9925-9 (1996); Valli et al., *Res. Virol.* 146:285-288 (1995)]. T-cell (Kato et al., *Biochem. Biophys. Res. Commun.* 206: 863-9 (1996); Mizutani et al., *Biochem. Biophys. Res. Comm.* 227:822-826; Mizutani et al., *J. Virol.* 70: 7219-7223 (1996); Nakajima et al., (1996) supra; Shimizu and Yoshikura, *J. Virol*, 68: 8406-8408 (1994); Shimizu et al., *Proc. Natl. Acad. Sci USA*, 89: 5477-5481 (1992); Shimizu et al., *Proc. Natl. Acad. Sci. USA*, 90: 6037-6041 (1993)], and hepatocyte [Kato et al., *Jpn. J. Cancer Res.*, 87: 787-92 (1996); *Tagawa, J. Gastoenterol. and Hepatol.*, 10: 523-527 (1995)] cell lines, as well as peripheral blood monocular cells (PBMCs) [Cribier et al., *J. Gen. Virol.*, 76: 2485-2491 (1995)], and primary cultures of human fetal hepatocytes [Carloni et al., *Arch. Virol. Suppl.* 8: 31-39 (1993); Cribier et al., (1995) supra; Iacovacci et al., *Res. Virol.*, 144: 275-279 (1993)] or hepatocytes from adult chimpanzees [Lanford et al., *Virology* 202: 606-14 (1994)]. HCV replication has also been detected in primary hepatocytes derived from a human HCV patient that were infected with the virus in vivo prior to cultivation [Ito et al., *J. Gen. Virol.* 77: 1043-1054 (1996)] and in the human hepatoma cell line Huh7 following transfection with RNA transcribed in vitro from an HCV-1 cDNA clone [Yoo et al., *J. Virol.*, 69: 32-38 (1995)]. The reported observation of replication in cells transfected with RNA derived from the HCV-1 clone was puzzling, since this clone lacks the required terminal 3'NTR sequence downstream of the homopolymer tract (see below), and because a number of unusual observations were reported (see the background section of U.S. patent application Ser. No. 08/811,566 (Now U.S. Pat. No. 6,127,116. The most well-characterized cell-culture systems for HCV replication utilize a B-cell line (Daudi) or T-cell lines persistently infected with retroviruses (HPB-Ma or MT-2) [Kato et al., (1995) supra; Mizutani et al., *Biochem Biophys Res. Comm.*, 227: 822-826 (1996a); Mizutani et al., (1996) supra; Nakajima et al., (1996) supra; Shimizu and Yoshikura, (1994) supra]; Shimizu, *Proc. Natl. Acad. Sci. USA*, 90: 6037-6041 (1993)]. HPBMa is infected with an amphotropic murine leukemia virus pseudotype of murine sarcoma virus, while MT-2 is infected with human T-cell lymphotropic virus type I (HTLV-I). Clones (HPBMa10-2 and MT-2C) that support HCV replication more efficiently than the uncloned population have been isolated for the two T-cell lines HPBMa and MT-2 [Mizutani et al. *J. Virol.* (1996) supra; Shimizu et al., (1993) supra]. However, the maximum levels of RNA replication obtained in these lines or in the Daudi lines after degradation of the input RNA is still only about $5 \times 10^4$ RNA molecules per $10^6$ cells [Mizutani et al., (1996) supra; Mizutani et al., (1996) supra] or $10^4$ RNA molecules per ml of culture medium [Nakajima et al., (1996) supra]. Although the level of replication is low, long-term infections of up to 198 days in one system [Mizutani et al., *Biochem. Biophys. Res. Comm.* 227: 822-826 (1996a)] and more than a year in another system [Nakajima et al., (1996) supra] have been documented, and infectious virus production has been demonstrated by serial cell-free or cell-mediated passage of the virus to naive cells.

However, efficient replication of an HCV clone comprising the essential conserved terminal 3' NTR sequence had not been observed until the work described in co-pending application Ser. No. 08/811,566, now U.S. Pat. No. 6,127,116, also reported in Kolykhalov et al., *Science* 277:570 (1997), which describes an infectious clone of an isolate of the H strain (type 1a). HCV clones of other subtypes are now known. See, e.g., Yanagi et al., *Virology* 262:250-263 (1999) and Yanagi et al., *Virology* 244:161-172 (1998). While RNA transcripts of these clones are able to infect chimpanzees, cell cultures with these clones only support replication of the virus poorly if at all.

As described in U.S. patent application Ser. No. 08/811, 566 (Now U.S. Pat. No. 6,127,116) (see, e.g., FIG. 2 therein) many variations of a functional clone are possible. These include full length or partial sequences where a foreign gene is inserted. The foreign gene can include, e.g., a reporter gene such as β-galactosidase or luciferase, or a gene encoding a selectable marker such as neo, DHFR, or tk. In a specific example disclosed therein, the neo gene is operably linked to an internal ribosome entry site (IRES), in order for infected cells to be selected by neomycin or G418 resistance. In this way, presence of replicating HCV RNA in essentially all surviving cells is assured. Additionally, the HCV polyprotein coding region of these clones can be deficient in some or all of the structural genes C, E1 and E2. Thus, replicons can be created without the production of virions. By combining the structural gene-deficient construct with a selectable marker such as neo, an efficiently replicating replicon system can be created that can be used to study HCV replication and for other purposes.

Examples of the replicons disclosed in U.S. patent application Ser. No. 08/811,566 (Now U.S. Pat. No. 6,127,116) is provided in Lohmann et al., *Science* 285:110-113 (1999). In that work, DNA clones of HCV replicons of genotype 1, subtype 1b were constructed. Features of those replicons that are not wild-type HCV features are: a polyprotein coding region lacking the genes encoding the HCV structural proteins; an EMCV IRES immediately 5' to the polyprotein region; and a neo gene immediately 3' to the 5' NTR (and the HCV IRES), where the 5' end of the HCV C protein gene is fused to the 5' end of the neo gene. When Huh-7 cells were transfected with RNA transcripts of these clones, 6 to >60 G418-resistant colonies arose per experiment. Although the number of cells treated was not specified, about $10^6$-$10^7$ cells are normally treated in experiments of this type. Therefore, it is believed that the transfection efficiency, as measured by G418-resistant colonies/total treated, was less than 0.01% in those studies.

Controls in the Lohmann et al. work included in-frame deletions of the active site of the NS5B polymerase. Although care was taken to remove template DNA from the control transcripts, several G418-resistant control colonies arose. Still, the number of G418-resistant control colonies that arose was much less than the colonies arising from the cells transfected with the replicons containing the wild-type NS5B.

When the G418-resistant colonies were subpassaged, most could not be maintained. Out of more than 303 G418-resistant colonies from non-control replicon treatments, 9 (<3%) could be subpassaged to establish stable cell lines. Replicons established in infected cell lines were sequenced. Although each replicon had a number of amino acid substitutions, the substitutions were scattered throughout the polyprotein coding region. Therefore, there were no mutations that were consistently in one area of the polyprotein coding region, and it was concluded that the establishment of the nine cell lines was not due to adaptive mutations in those replicons. This contention was experimentally tested by transfection/reconstitution experiments that did not provide evidence for adaptive changes.

Despite the advances described above, more efficient HCV-infected cell systems are needed for the production of concentrated virus stocks, structural analysis of virion components, evaluation of putative antiviral therapies including vaccines and antiviral compounds, and improved analyses of intracellular viral processes, including RNA replication. Thus, there is a need for various types of HCV clones that can be used for any of the above purposes. There is also a need to characterize HCV with respect to regions of the genome that might contribute to more efficient in vitro or in vivo replication and virion production.

SUMMARY OF THE INVENTION

Thus, a primary object of the present invention has been to provide DNA encoding non-naturally occurring HCV that is capable of replication.

A related object of the invention is to provide genomic RNA from the above DNA. Still another object of the invention is to provide attenuated HCV DNA or genomic RNA suitable for vaccine development, which can invade a cell and replicate but cannot propagate infectious virus.

Another object of the invention is to provide in vitro and in vivo models of HCV infection and RNA replication for testing anti-HCV (or antiviral) drugs, for evaluating drug resistance, and for testing attenuated HCV viral vaccines.

An additional object of the invention is to provide replicating HCV replicons. These replicons do not encode structural proteins but may encode a foreign protein such as a reporter gene or a selectable marker.

Still another object of the invention is to provide adaptive replicons, with increased ability to establish replication in continuous or primary cell lines.

Briefly, therefore, the inventors have succeeded in discovering methods of creating replicating HCV variants, including variants with adaptive mutations in HCV that improve their ability to establish RNA replication in culture to create continuous cell lines. These HCV variants and the cell lines that harbor them are useful for studying replication and other HCV characteristics. The cell lines are also useful for developing vaccines and for testing compounds for antiviral properties.

Thus, in some embodiments, the present invention is directed to a polynucleotide comprising a non-naturally occurring HCV sequence that is capable of productive replication in a host cell, or is capable of being transcribed into a non-naturally occurring HCV sequence that is capable of productive replication in a host cell. The HCV sequence comprises, from 5' to 3' on the positive-sense nucleic acid, a functional 5' non-translated region (5' NTR); one or more protein coding regions, including at least one polyprotein coding region that is capable of replicating HCV RNA; and a functional HCV 3non-translated region (3' NTR). In preferred embodiments of these polynucleotides, the 5' NTR is an HCV 5' NTR, the polynucleotide comprises at least one IRES selected from the group consisting of a viral IRES, a cellular IRES, and an artificial IRES, and the polyprotein coding region is an HCV polyprotein coding region.

In certain aspects of these embodiments, the above polynucleotides further comprise an adaptive mutation. The adaptive mutation can be such that the polynucleotide has a transfection efficiency into mammalian cells of greater than 0.01%; more preferably greater than 0.1%; even more preferably, greater than 1%; still more preferably greater than 5%, may be about 6%. The adaptive mutations can be such that the polynucleotide is capable of replication in a non-hepatic cell, for example HeLa cells. The adaptive mutations can also cause the polynucleotide to have attenuated virulence, wherein the HCV is impaired in its ability to cause disease, establish chronic infections, trigger autoimmune responses, and transform cells.

In some embodiments of the above described adaptive mutants, the polyprotein region comprises an NS5A gene that is not a wild-type NS5A gene. Preferably, the NS5A gene comprises a mutation. The mutation is preferably within 50 nucleotides of an ISDR or includes the ISDR; more preferably the mutation is within 20 nt of the ISDR, or includes the ISDR. Examples of these adaptive mutations are those that encode an amino acid sequence change selected from the group consisting of Ser (1179) to Ile, Arg (1164) to Gly, Ala(1174) to Ser, Ser(1172) to Cys, and Ser(1172) to Pro of SEQ ID NO:3. Other adaptive mutations include a deletion of at least a portion of the ISDR, and may comprise the entire ISDR. In a particular embodiment, the adaptive mutation comprises a deletion of nucleotides 5345 to 5485 of SEQ ID NO:6.

In some embodiments of the invention polynucleotides, the HCV polyprotein coding region encodes all HCV structural and nonstructural proteins. In other embodiments, the polyprotein coding region is incapable of making infectious HCV particles, making the HCV variant a replicon. Preferably the inability to make HCV particles is due to a deletion in the structural protein coding region. Some embodiments of these replicons further comprise a foreign gene operably linked to a first IRES and the HCV polyprotein coding region operably linked to a second IRES. Preferably, the replicon comprises a genotype 1 HCV sequence, most preferably subtype 1b. Preferred foreign genes in these replicons are selectable markers or reporter genes. In other preferred replicon embodiments, the first IRES is an HCV IRES, the foreign gene is a neo gene, and the second IRES is a EMCV IRES. Examples of the above replicons include SEQ ID NO:5, SEQ ID NO:6, SEQ ID NO:22 and SEQ ID NO:25. The above replicons also preferably comprise an adaptive mutation, including any of the adaptive phenotypes previously described, including increased transfection efficiency, replication in a non-hepatic cell including HeLa cells, and attenuated virulence, and further comprising any of the adaptive mutations previously described, such as the various NS5A mutations and deletions previously described.

The polynucleotides of the present invention can be in the form of RNA or DNA. Preferred embodiments of the polynucleotides are SEQ ID NOs:5-13 and 22-25, the complements thereof, and the RNA equivalents of the sequences or their complements. In certain embodiments, the polynucleotides are capable of productive infection in a chimpanzee upon intrahepatic injection.

The present invention is also directed to expression vectors comprising DNA forms of any of the above polynucleotides, operably associated with a promoter. Additionally, the invention is directed to cells comprising the above expression vectors as well as host cells comprising any of the polynucleotides described above. The host cells are preferably mammalian cells, more preferably human cells. The host cells are preferably hepatocytes, T-cells, B-cells, or foreskin fibroblasts; most preferably hepatocytes. Certain adaptive mutants can also replicate in HeLa cells. The host cells can be within a non-human mammal capable of supporting transfection and replication of the HCV RNA, and infection when the HCV RNA encodes a virus particle. A preferred non-human mammal is a chimpanzee.

In additional embodiments, the present invention is directed to methods for identifying a cell line that is permissive for RNA replication with HCV. The method includes the steps of contacting a cell in tissue culture with an infectious amount of the above-described polynucleotides, and detecting replication of HCV variants in cells of the cell line.

The present invention is also directed to a method for producing a cell line comprising replicating HCV. The method includes the steps of (a) transcribing the above-described expression vector to synthesize HCV RNA; (b) transfecting a cell with the HCV RNA; and (c) culturing the cell.

Additionally, the present invention is directed to a vaccine. The vaccine includes any of the above-described polynucleotides, in a pharmaceutically acceptable carrier. In related embodiments, the present invention is directed to a method of inducing immunoprotection to HCV in a primate. The method includes administering the vaccine to the primate.

In further embodiments, the present invention is directed to a method of testing a compound for inhibiting HCV replication. The method includes the steps of (a) treating the above described host cells with the compound; and (b) evaluating the treated host cell for reduced replication, wherein reduced HCV replication indicates the ability of the compound to inhibit replication.

In additional embodiments, the present invention is directed to a method of testing a compound for inhibiting HCV infection. The method comprises treating a host cell with the compound before, during or after infecting the host cell with any of the invention polynucleotides.

In still other embodiments, the present invention is directed to an HCV variant that has (a) transfection efficiency greater than 0.01%, as determined by replication-dependent neomycin resistance, or (b) greater ability of initial colonies of cells transfected with the variant to survive subpassage than wild-type HCV genotype 1, subtype 1b. The HCV variant also has, from 5' to 3' on the positive-sense nucleic acid, a functional HCV 5' non-translated region (5'NTR) comprising an extreme 5'-terminal conserved sequence; an HCV polyprotein coding region; and a functional HCV 3' non-translated region (3'NTR) comprising a variable region, a polypyrimidine region, and an extreme 3'-terminal conserved sequence. In preferred embodiments, the transfection efficiency is greater than 0.1%; in more preferred embodiments, greater than 1%; in still more preferred embodiments, greater than 5%. In the most preferred embodiments, the transfection efficiency is about 6%.

The variants can have any of the characteristics of the polynucleotides described above. However, preferred variants comprise the NS5A mutation or deletion described for the polynucleotides above.

Among the several advantages achieved by the present invention are the provision of polynucleotides comprising non-naturally occurring HCV sequences; the provision of HCV variants that have a transfection efficiency and ability to survive subpassage greater than HCV forms that have wild-type polyprotein coding regions; the provision of expression vectors comprising the above polynucleotides and HCV variants; the provision of cells and host cells comprising the above expression vectors, the provision of methods for identifying a cell line that is permissive for RNA replication with HCV; the provision of vaccines comprising the above polynucleotides in a pharmaceutically acceptable carrier; the provision of methods for inducing immunoprotection to HCV in a primate; and the provision of methods for testing a compound for inhibiting HCV replication.

BRIEF DESCRIPTION OF THE DRAWINGS

FIG. 4. Generation of G418-resistant cell clones. At the top is a diagram of the HCVrep1bBartMan replicons as described in FIG. 3. The middle text summarizes the steps used to isolate the adaptive mutants, which are further described in Example 1. The bottom chart summarizes several characteristics of some of the replicons isolated as described in the Example.

FIG. 5. Synthesis of HCV-specific RNA and proteins. FIG. 5A illustrates actinomycin D-resistant RNA replication of four adaptive replicons as further described in the Example. FIG. 5B illustrates the immunoprecipitation of $^{35}$S-labeled HCV-specific proteins of three adaptive replicons as further described in Example 1.

DETAILED DESCRIPTION OF THE INVENTION

Definitions

Figure 1:
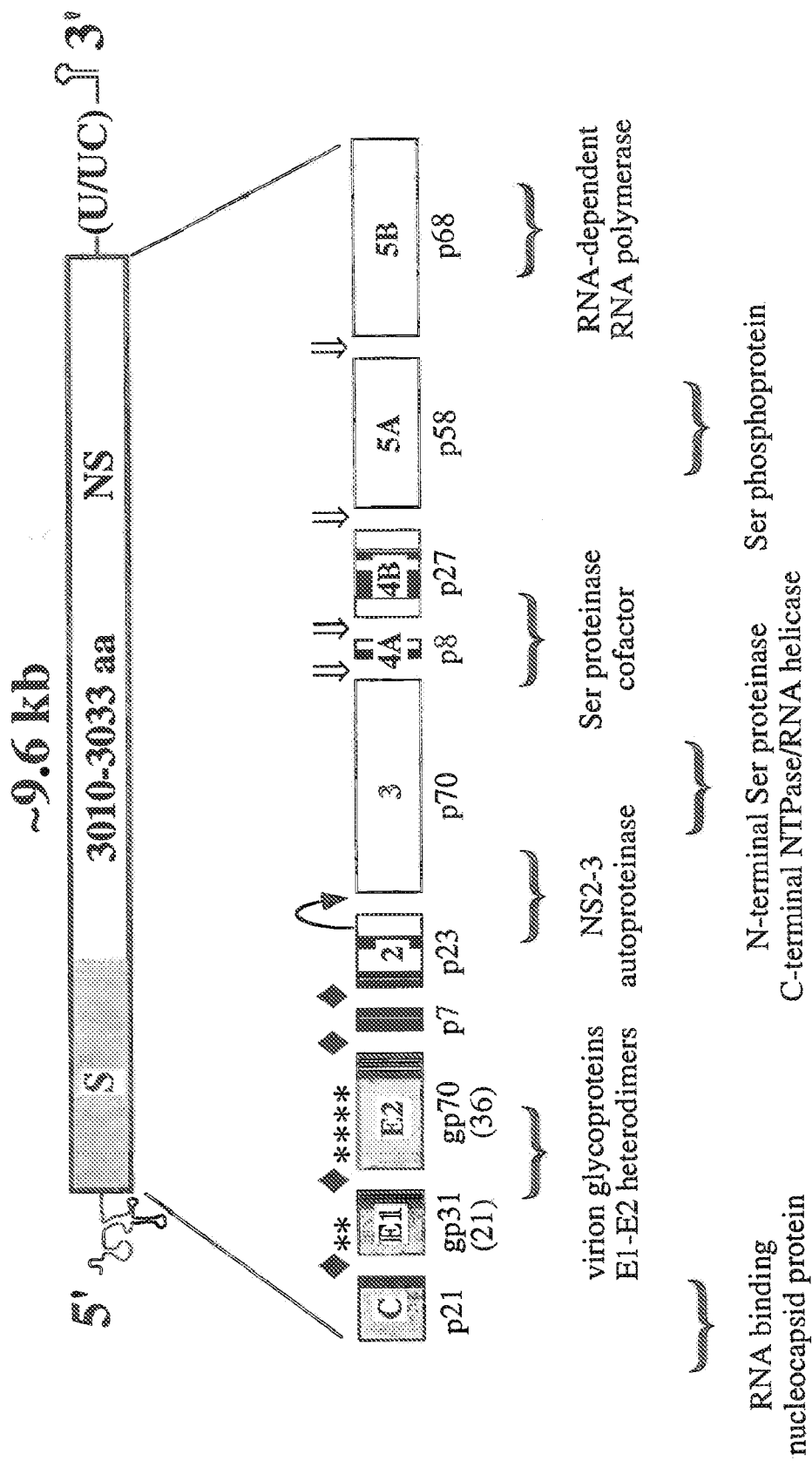
FIG. 1. HCV genome structure, polyprotein processing, and protein features. At the top is depicted the viral genome with the structural and nonstructural protein coding regions, and the 5' and 3' NTRs, and the putative 3' secondary structure. Boxes below the genome indicate proteins generated by the proteolytic processing cascade. Putative structural proteins are indicated by shaded boxes and the nonstructural proteins by open boxes. Contiguous stretches of uncharged amino acids are shown by black bars. Asterisks denote proteins with N-linked glycans but do not necessarily indicate the position or number of sites utilized. Cleavage sites shown are for host signalase (♦), the NS2-3 proteinase (curved arrow), an the NS3-4A serine protease (↓).

Various terms are used herein, which have the following definitions:

As used herein, "HCV polyprotein coding region" means the portion of a hepatitis C virus that codes for the polyprotein open reading frame (ORF). This ORF may encode proteins that are the same or different than wild-type HCV proteins. The ORF may also encode only some of the functional proteins encoded by a wild-type polyprotein coding region. The proteins encoded therein may also be from different isolates of HCV, and non-HCV proteins may also be encoded therein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

In a specific embodiment, the term "about" or "approximately" means within 20%, preferably within 10%, and more preferably within 5% of a given value or range.

The term "virus infection" as used herein, refers to the usual way that wild-type virus particles become established in host cells. This generally includes binding to the host cell, uptake, delivery to the cytosol or nucleus, and initiation of replication.

The term "transfection" as used herein, refers to the infection of a cell with a polynucleotide. The polynucleotide can be DNA or RNA. A preferred method of transfecting a cell with an HCV polynucleotide is with replication competent RNA. Delivery to permissive cells can be facilitated by electroporation, charged liposomes, high salt, DE dextran, etc. Replication competent RNAs can also be launched in cells after transfection of DNA such as plasmids or DNA viruses that have been appropriately engineered to provide transcription initiation and termination signals. The transfected RNAs can represent full-length genome RNAs capable of initating a complete replication cycle (including production of progeny virus), or they may be defective lacking one or more RNA elements or proteins essential for virion production but not RNA replication. The latter RNAs, which are lacking in the ability to produce a virion, will be referred to generally herein as "replication competent RNAs", "RNA replicons" or "replicons".

As used herein, the term "subpassage" connotes the transfer of a colony from one vessel of media to another vessel of media. Examples of vessels of media include dishes, bottles or test tubes with solid or liquid growth media. Unless otherwise indicated, "subpassage" means the transfer of a colony of HCV-transfected cells from a vessel of media where the newly transfected cells were plated to a vessel of media where the colony is isolated.

The term "authentic" is used herein to refer to an HCV polynucleotide, whether a DNA or RNA, that provides for replication and production of functional HCV proteins, or components thereof. The authentic HCV polynucleotides of the present invention are capable of replication and may be infectious, e.g., in a chimpanzee model or in tissue culture, to form viral particles (i.e., "virions"). An authentic HCV polynucleotide of the present invention may also be a "replicon", such that it is incapable of producing the full complement of structural proteins to make a replication competent infectious virion. However, such replicons are capable of RNA replication. Thus, the authentic HCV polynucleotides exemplified in the present application contains all of the virus-encoded information, whether in RNA elements or encoded proteins, necessary for initiation of an HCV RNA replication cycle. The authentic HCV polynucleotides of the invention include modifications described herein, e.g., by site-directed mutagenesis or by culture adaptation, producing a defective or attenuated derivative, or an adaptive variant. Alternatively, sequences from other genotypes or isolates can be substituted for the homologous sequence of the specific embodiments described herein. For example, an authentic HCV nucleic acid of the invention may comprise the adaptive mutations disclosed herein, e.g., on a recipient plasmid, engineered into the polyprotein coding region of a functional clone from another isolate or genotype (either a consensus region or one obtained by very high fidelity cloning). In addition, the HCV polynucleotide of the present invention can include a foreign gene, such as a gene encoding a selectable marker or a reporter protein.

General Description

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Ausubel et al. (ed.) (1993) "Current protocols in molecular biology. Green Publishing Associates, New York; Ausubel et al. (1995), "Short Protocols in Molecular Biology", John Wiley and Sons; Joseph Sambrook et al. (1989), "Molecular Cloning, A Laboratory Manual", second ed., Cold Spring Harbor Laboratory Press; the series, METHODS IN ENZYMOLOGY (Academic Press, Inc.); *Animal Cell Culture* [R. I. Freshney, ed. (1986)]; Lau, ed. (1999), HEPATITIS C PROTOCOLS, Humana Press, New York; and *Immobilized Cells And Enzymes* [IRL Press, (1986)]; all of which are incorporated by reference.

The present invention is directed to variants of hepatitis C virus (HCV) and methods for producing the variants. As used herein, an HCV variant is a non-naturally occurring HCV sequence that is capable of productive replication in a host cell. The genetic sequence of these variants may comprise insertions, deletions, or base mutations from wild type HCV sequences. As further discussed infra, the variants may be produced by genetic engineering, by methods known to the skilled artisan (see, e.g., U.S. patent application Ser. No. 08/811,566 (Now U.S. Pat. No. 6,127,116); Lohmann et al., *Science* 285:110-113(1999)). Alternatively, as further discussed infra, the variants may also be produced by culture selection methods, or a combination of culture selection and genetic engineering.

The variants are in the form of DNA or RNA and can be incorporated into any useful form of those compounds, for example in extrachromosomal DNA that replicates in a microorganism such as *E. coli* or yeast. Included among these are plasmids, phage, BACs, YACs, etc. RNA and virions comprising the variant are also envisioned as within the scope of the invention. The variants of the present invention can also be in the form of cassettes for insertion into a DNA cloning vector. The HCV RNAs are envisioned to be complementary to any HCV DNA disclosed herein. An infectious HCV RNA is a positive strand RNA created from the negative strand template of the HCV DNA clone of the invention.

The variants of the present invention are not narrowly limited to any particular virus subtype. Thus, any particular component of the variant, or the entire variant, may be from any HCV subtype. Preferred subtypes are 1a and 1b, due to the widespread occurrence, as well as the large amount of knowledge available for those two subtypes. However, the use of any other genotype or subtype, as would be considered within the skill of the art, is envisioned as within the scope of the invention. These subtypes include, but are not limited to, any subtypes within genotypes HCV-1, HCV-2, HCV-3, HCV-4, HCV-5, and HCV-6. Moreover, since HCV lacks proofreading activity, the virus itself readily mutates, forming mutant "quasi-species" of HCV that are also contemplated as useful for the present invention. Such mutations are easily identified by sequencing isolates from a subject, as detailed herein or in U.S. patent application Ser. No. 08/811,566 (Now U.S. Pat. No. 6,127,116). It would be expected that the methods and compositions disclosed herein are useful for any known subtype or quasi-species, or any subtype or quasi-species not now known but that is discovered in the future.

The HCV variants of the invention include a 5'-NTR conserved sequence, which generally comprises the 5'-terminal sequence GCCAGCC, and which may have additional bases upstream of this conserved sequence without affecting functional activity of the HCV nucleic acid. In a preferred embodiment, the 5'-GCCAGCC includes from 0 to about 10 additional upstream bases; more preferably it includes from 0 to about 5 upstream bases; more preferably still it includes 0, one, or two upstream bases. In specific embodiments, the extreme 5'-terminal sequence may be GCCAGCC; GGCCAGCC; UGCCAGCC; AGCCAGCC; AAGCCAGCC; GAGCCAGCC; GUGCCAGCC; or GCGCCAGCC, wherein the sequence GCCAGCC is the 5'-terminus of SEQ ID NO:1. However, the scope of the HCV variants of the invention encompasses any functional HCV 5' NTR, whether now known or later discovered.

The HCV variants of the invention also include a 3' NTR that comprises a poly-pyrimidine region as is known in wild-type HCV. These polypyrimidine regions are known to comprise, on the positive-strand HCV RNA, a poly(U)/poly(UC) tract or a poly(A) tract. However, the polypyrimidine region of the present invention may also include other polypyrimidine tracts that are not now known but are later found to be functional in infectious HCV. As is known in the art, the polypyrimidine tract may be of variable length: both short (about 75 bases) and long (133 bases) are effective, although an HCV clone containing a long poly(U/UC) tract is found to be highly infectious. Longer tracts may be found in naturally occurring HCV isolates. Thus, an authentic HCV nucleic acid of the invention may have a variable length polypyrimidine tract.

The 3' NTR also comprises, at its extreme 3' end, the highly conserved RNA element of about 98 nucleotides known in the art, and as described in, e.g., U.S. Pat. No. 5,874,565, U.S. patent application Ser. No. 08/811,566 (Now U.S. Pat. No. 6,127,116), and U.S. Pat. No. 5,837,463. In a specific aspect, the 3'-NTR extreme terminus is RNA homologous to a DNA having the sequence 5'-TGGTGGCTCCATCTTAGC-CCTAGTCACGGCTAGCTGTGAAAGGTCCGTGAGCC GCATGACTGCAGAGAGTGCTGATACTG-GCCTCTCTGCTGATCATGT-3' (SEQ ID NO:2). However, the scope of the invention is meant to encompass HCV variants with any HCV 3' NTR that allows virus replication, whether the sequence is now known or later discovered. Included are 3' NTRs that do not comprise a variable region.

The HCV variants of the present invention also include a polyprotein coding region sufficient to allow replication of the HCV RNA. Thus, the polyprotein coding region may be deficient in functional genes encoding the full complement of the HCV structural genes C, E1 and E2. In addition, the polyprotein coding region may comprise deletions, insertions, or mutations that do not occur in wild-type HCV strains. Further, the polyprotein coding region may be chimeric, such that some of the genes encoded therein are from analogous regions of another virus, as discussed infra.

The HCV variants encompassed by the present invention include variants that do not produce virus particles. These variants, which may be termed "replicons", lack the ability to produce a fully functional complement of the structural proteins C, E1 and E2. The inability to produce the functional structural protein component of the HCV virus may be conferred by deletion of the genes encoding one, two, or all three of these proteins. Alternatively, a deletion of a small portion of the coding sequence of one of the structural proteins, or a mutation in a critical region of the coding sequence, or an insertion into the coding sequence could lead to an HCV that cannot produce virions. In the latter case, the insertion can be any sequence that disrupts the ability of the structural protein from becoming part of a virion, and can include functional sequences, such as those that encode a reporter gene (such as β-galactosidase) or those that confers selectability to the cell harboring the replicon (such as neo). The above manipulations are entirely within the skill of the art. See, e.g., Lohmann et al., supra and Example 1. As discussed infra, such variants are useful for studying replication of the HCV virus, among other things.

The variants of the present invention can also comprise an alteration in the coding sequence of the polyprotein coding region that does not affect the production of functional virions or replicons. These alterations can be such that the amino acid sequence of the mature protein is not changed from the wild-type sequence, due to the degeneracy of the genetic code. Such alterations can be useful, e.g., when they introduce or remove a restriction site, such that the size of HCV fragments produced by digestion with a restriction enzyme is altered. This provides a distinguishing characteristic of that variant, which can be used, e.g., to identify a particular infectious isolate in a multiple infection animal model, or to provide convenient sites for subsequent engineering. Any technique for mutagenesis known in the art can be used, including but not limited to in vitro site-directed mutagenesis [Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710], use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61-70].

Alterations in the polyprotein coding sequence can also introduce conservative amino acid substitutions in the HCV-encoded proteins. Conservative amino acid substitutions refer to the interchangeability of residues having similar side chains. Conservatively substituted amino acids can be grouped according to the chemical properties of their side chains. For example, one grouping of amino acids includes those amino acids have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions are: R-K; E-D, Y—F, L-M; V—I, and Q-H. Conservative amino acid substitutions, when conferred on the structural proteins, can alter antigenic epitopes, and thus the immune reactivity of the virus. Those substitutions could also alter the function of the non-structural proteins, such that the virus reproduces at a different rate or is altered in its ability to replicate in cell culture or in an organism. See, e.g., Example 1, where replicon IV is adaptive to cell culture conditions due to the conservative amino acid substitution Ser→Cys in the NS5A protein.

Alterations in the polyprotein coding region could also introduce nonconservative amino acid substitutions in one or more of the proteins encoded therein. Nonconservative substitutions would be expected to alter protein function more drastically than conservative substitutions, and would thus be more likely than conservative substitutions to alter phenotypic characteristics of the virus such as replication rate, adaptation to cell culture or in vivo culture, and displayed antigenic determinants. Examples are several adaptive mutations in the NS5A coding region described in the, infra.

In some embodiments of the invention, the polyprotein coding region has a consensus sequence derived from more than one HCV isolate. For example, an authentic HCV nucleic acid of the invention may comprise a 5' and 3' sequence from any one subtype of the virus and a polyprotein region from any other subtype. Alternatively, only one of the proteins encoded in the polyprotein might be from another viral subtype. In this way, the effect of a particular protein in conferring characteristics of a particular strain (e.g., reduced virulence, increased replication rate etc.) can be studied.

Chimeras with other viruses, such as with bovine viral diarrhea virus, or another flavivirus, are also envisioned. See, e.g., PCT/US99/08850, incorporated herein by reference. In these embodiments, components of the functional clones can be used to construct chimeric viruses for assay of HCV gene functions and inhibitors thereof [Filocamo et al., *J. Virol.* 71: 1417-1427 (1997); Hahm et al., *Virology* 226: 318-326 (1996); Lu and Wimmer, *Proc Natl Acad Sci USA* 93: 1412-7 (1996)]. In one such extension of the invention, functional HCV elements such as the 5' IRES, proteases, RNA helicase, polymerase, or 3' NTR are used to create chimeric derivatives of BVDV whose productive replication is dependent on one or more of these HCV elements. Such BVDV/HCV chimeras can then be used to screen for and evaluate antiviral strategies against these functional components.

Chimeras where a gene encoding a structural or nonstructural protein from a closely related virus such as GB virus B replaces the corresponding HCV gene would also be expected to be functional. See, e.g., Butkiewicz et al., 2000, *J. Virol.* 74, 4291-4301.

Other alterations in the polyprotein coding region contemplated by the present invention include deletions or insertions in the sequence. Such alterations may also alter replication rate, adaptation to various growth conditions, or antigenic determinants. A preferred example of a useful deletion includes the 47 amino acid deletion and replacement of Ser 1182 to Asp 1229 of SEQ ID NO:3 with Tyr, which is an adaptive mutation in the NS5A that provides greater transfection efficiency than HCVs with wild-type NS5A. See Example 1.

Insertions into the polyprotein coding region can be of any length and into any area of the region, provided the modified HCV is still able to replicate. Preferably, the insertion is engineered in frame with the rest of the polyprotein coding region, to allow correct translation of the polyprotein region downstream from the insertion.

Insertions into the polyprotein coding region could introduce a gene encoding a heterologous protein. The choice of heterologous protein is not narrowly limited and can include a protein that is therapeutic to the infected host or cell, or a protein that is harvested and purified for another purpose. Particularly useful heterologous genes include those used for detection of the variant (i.e., reporter genes), or for selection of cells having the variant. Nonlimiting examples of reporter genes useful in the present invention include β-galactosidase, β-glucuronidase, firefly or bacterial luciferase, green fluorescent protein (GFP) and humanized derivatives thereof, cell surface markers, and secreted markers. Such products are either assayed directly or may activate the expression or activity of additional reporters. Nonlimiting examples of selectable markers for mammalian cells include, but are not limited to, the genes encoding dihydrofolate reductase (DHFR; methotrexate resistance), thymidine kinase (tk; methotrexate resistance), puromycin acetyl transferase (pac; puromycin resistance), neomycin resistance (neo; resistance to neomycin or G418), mycophenolic acid resistance (gpt), hygromycin resistance, blasticidin resistance, and resistance to zeocin. Other selectable markers can be used in different hosts such as yeast (ura3, his3, leu2, trp1).

The present invention also encompasses HCV variants that have alterations in the noncoding regions of the virus. For example, the foreign gene discussed above can also be inserted into a noncoding region of the virus, provided the region with the insert continues to be sufficiently functional to allow replication. To provide for translation of a foreign gene inserted into a noncoding region, the foreign gene must be operatively linked to translational start signals, preferably an internal ribosome entry site (IRES) derived from cellular or viral mRNAs [Jang et al., *Enzyme* 44: 292-309 (1991); Macejak and Sarnow, *Nature* 353: 90-94 1991); Molla et al., *Nature* 356: 255-257 (1992)]. In essence, this strategy creates a second cistron in the variant, separate from the polyprotein coding region cistron. A preferred IRES is the encephalomyocarditis virus (EMCV) IRES.

The foreign gene can also be inserted into the 3' NTR or the 5' NTR. In the 3' NTR, the foreign gene/IRES cassette is preferably inserted into the most 5', variable domain. However, insertions are also envisioned for other regions of the 3' NTR, such as at the junction of the variable region and the polypyrimidine region, or within the polypyrimidine region.

In the 5' NTR, the foreign gene is preferably inserted into the area just adjacent (3' to) the internal HCV IRES. In these variants, the foreign gene is engineered to be operably linked to the HCV IRES. Where this is the case, it is preferred that the second IRES (e.g., an EMCV IRES) is engineered just 5' to the polyprotein coding region, to be operably linked to that region. See Example and Lohmann et al., supra.

Some of the above strategies for functional expression of heterologous genes have been previously described. See Bredenbeek and Rice, (1992) supra for review; see, also FIG. 2, which is also FIG. 2 of U.S. patent application Ser. No. 08/811,566 (Now U.S. Pat. No. 6,127,116).

Additionally, noncoding region alterations such as mutations, deletions or insertions that do not encode a foreign protein are within the scope of the invention. For example, mutations, deletions of insertions in the variable or polypyrimidine regions of the 3' NTR, including deletions of the entire variable region, or in the 5' NTR region, that create or destroy restriction sites or make the variant otherwise identifiable can be used advantageously to create a "tagged" variant. See, e.g., Example, where a mutation in the variable region of the 3' NTR created an easily identifiable AvaII restriction site, and where a deletion in the polypyrimidine region created another identifiable variant.

The polyprotein coding sequence can comprise mutants with desirable functional adaptations such as adaptive or attenuated variants. These improved variants can be superior in any desired characteristic. Nonlimiting examples of characteristics that can be improved by the present methods include more rapid or more accurate replication in vivo or in culture, improved transfection efficiency, improved ability to establish subpassaged cell lines, ability to infect a host or a host cell line, virulence, and attenuation of disease symptoms.

Such HCV variants may be adaptive, e.g., by selection for propagation in animals or in vitro. See, e.g., Example. Alternatively, the variants can be engineered by design to comprise the functional adaptation. See, e.g., Example, where a deletion was designed that had increased transfection efficiency and ability to be subpassaged to create a stable cell line, supporting persistent HCV replication.

Non-functional HCV clones, e.g., that are incapable of genuine replication, that fail to produce HCV proteins, that do not produce HCV RNA as detected by Northern analysis, or that fail to infect susceptible animals or cell lines in vitro, can be corrected using components of the variants of the present invention. By comparing a variant of an authentic HCV nucleic acid sequence of the invention, with the sequence of the non-functional HCV clone, defects in the non-functional clone can be identified and corrected, and the corrected, replicating variant could have characteristics like the variant, such as an adaptive mutation, etc. All of the methods for modifying nucleic acid sequences available to one of skill in the art to effect modifications in the non-functional HCV genome, including but not limited to site-directed mutagenesis, substitution of the functional sequence from an authentic HCV variant for the homologous sequence in the non-functional clone, etc.

Adaptation of HCV for more improved cell culture characteristics. Replication and transfection efficiency and stability of virions and replicons that have wild-type polyprotein replication in cell culture is inefficient. That is, cells transfected with, e.g., RNA transcripts of clones of these strains replicate slowly in culture and the transfected cells are difficult to maintain. Additionally, transfection efficiency is poor. That is, very few cells that are transfected with the RNA replicon are able to support HCV replication. See, e.g., Example 1 and Lohmann et al., supra, where less than 0.01% of Huh-7 cells transfected with RNA transcripts of replicons that have a wild-type (genotype 1, subtype 1b) nonstructural polyprotein coding region grew into colonies on the petri dish where the transfectants were plated. Furthermore, a low percentage of colonies that arose from the original plating (<3%) could be subpassaged onto another dish of media to form an isolated stable cell line supporting HCV replication.

"Transfection efficiency" is defined by determining the percent of cells having replicating HCV RNA that continue to translate proteins encoded by the transfected nucleic acids. The easiest way to measure this is by determining the percentage of cells that exhibit a characteristic conferred by the HCV RNA. See, e.g., Example 1, where replicons comprising a neo gene conferred G418 resistance to the transfected cells, and where the cells were G418 resistant after dividing and forming colonies on the dish where the transfected cells were plated. In that example, G418 resistance would not persist sufficiently for colonies to form unless the HCV RNA was able to replicate and partition into the dividing cells while continuing to replicate and translate the neo gene to confer G418 resistance. Transfection efficiency is thus replication dependent, in that the transfected HCV must replicate, transcribe, and translate the measured characteristic (here, G418 resistance). In the context of the neo selectable marker, this method of determining transfection efficiency is termed "replication-dependent neomycin resistance". This is the preferred way of measuring transfection efficiency because it only measures transcription from HCV that established itself sufficiently to replicate and partition into dividing cells to form a colony.

Another disadvantageous cell culture characteristic of HCV nucleic acid that has wild-type nonstructural polyprotein genes is that only a low percentage of colonies that form after transfection and selection are able to continue to be maintained upon subpassage as continuous cell lines harboring replicating RNA. This was <3% in Lohmann et al., as discussed supra.

Disadvantageous characteristics of HCV having wild-type nonstructural polyprotein genes can be reduced by utilizing certain adaptive mutations and deletions in the NS5A coding region or elsewhere as disclosed herein. Preferred mutations comprise alterations in the encoded amino acid sequence in a region of the NS5A that is just 5' to the coding region of the "interferon sensitivity-determining region" (ISDR). Specifically, various mutations within about 50 nucleotides 5' to the ISDR, more preferably within about 20 nucleotides of the ISDR, where the encoded amino acid sequence is altered, have the effect of adapting an HCV to have higher transfection efficiency and increased ability to withstand subpassage to establish a cell line harboring persistent HCV replication. Specific mutations having this effect include Ser to Ile at amino acid 1179 of SEQ ID NO:3 (subtype 1b nonstructural polyprotein region), conferred, for example, by the mutation g to t at position 5336 of SEQ ID NO:6, embodied in SEQ ID NO:8 (nucleotide[nt] and SEQ ID NO:16 (amino acid[aa]); Arg to Gly at amino acid 1164 of SEQ ID NO:3, conferred, for example, by the mutation from a to g at position 5289 of SEQ ID NO:6, embodied in SEQ ID NO:9 (nt) and SEQ ID NO:17 (aa); Ala to Ser at amino acid 1174 of SEQ ID NO:3, conferred, for example, by the mutation from g to t at position 5320 of SEQ ID NO:6, embodied in SEQ ID NO:10 (nt) and the NS5A amino acid sequence of SEQ ID NO:19; Ser to Cys at amino acid 1172 of SEQ ID NO:3, conferred, for example, by the mutation c to g at position 5315 of SEQ ID NO:6, embodied in the NS5A gene SEQ ID NO:11 and the NS5A amino acid sequence of SEQ ID NO:20; and Ser to Pro at amino acid 1172 of SEQ ID NO:3, conferred, for example by the mutation t to c at position 5314 of SEQ ID NO:6, embodied in the NS5A gene SEQ ID NO:12 and the NS5A amino acid SEQ ID NO:21. The adaptive effect of these mutations is surprising since this region of HCV is normally conserved among HCV isolates. Additionally, deletions within the ISDR, including deletions of the entire ISDR and various flanking sequences, cause this adaptive effect. Among these deletions is the substitution of the ISDR and flanking sequence comprising amino acids 1182 to 1229 of SEQ ID NO:3 with a tyrosine, conferred, for example, by the deletion of nt 5345-5485 of SEQ ID NO:6, and embodied in SEQ ID NO:7 (nt) and the NS5A amino acid SEQ ID NO:14.

HCV variants comprising mutations adaptive to cell culture may also be attenuated, that is impaired in its ability to cause disease, establish chronic infections, trigger autoimmune responses, and transform cells.

The present invention also discloses methods for selecting for adaptive HCV variants. These methods comprise the use of an HCV virion or preferably a replicon, which further comprises a dominant selectable marker such as a neo gene. Cells are transfected with these variants. The transfectants are plated into selection media, such as G418 when the neo gene is utilized in the variant. Colonies that arise to exhibit resistance to the selectable marker are subpassaged into fresh selection media. HCV in colonies that withstand subpassage to establish a cell line harboring HCV replication can be isolated and used to transfect additional cells. Any of these colonies that show increased transfection efficiency or other desirable characteristics, such as the ability to withstand subpassage, are adaptive variants, where the adaptive nature of the variant is conferred by at least one mutation or deletion. Selected areas of the HCV in these adaptive variants are sequenced. Preferably, at least the NS5A is sequenced. More preferably, the entire polyprotein coding region is sequenced. Any mutations in these variants can be further evaluated to determine the adaptive nature of the mutations. That evaluation preferably involves recreating the mutation in an otherwise wild-type coding region and determining if the recreated HCV mutant exhibits the adaptive phenotype of the original mutant.

Adaptive mutations could also be manifested, but are not restricted to: (i) altering the tropism of HCV RNA replication; (ii) altering viral products responsible for deleterious effects on host cells; (iii) increasing or decreasing HCV RNA replication efficiency; (iv) increasing or decreasing HCV RNA packaging efficiency and/or assembly and release of HCV particles; (v) altering cell tropism at the level of receptor binding and entry. Thus, the engineered dominant selectable marker, whose expression is dependent upon productive HCV RNA replication, can be used to select for adaptive mutations in either the HCV replication machinery or the transfected host cell, or both. In addition, dominant selectable markers can be used to select for mutations in the HCV replication machinery that allow higher levels of RNA replication or particle formation. In one example, engineered HCV derivatives expressing a mutant form of DHFR can be used to confer resistance to methotrexate (MTX). As a dominant selectable marker, mutant DHFR is inefficient since nearly stoichiometric amounts are required for MTX resistance. By successively increasing concentrations of MTX in the medium, increased quantities of DHFR will be required for continued survival of cells harboring the replicating HCV RNA. This selection scheme, or similar ones based on this concept, can result in the selection of mutations in the HCV RNA replication machinery allowing higher levels of HCV RNA replication and RNA accumulation. Similar selections can be applied for mutations allowing production of higher yields of HCV particles in cell culture or for mutant HCV particles with altered cell tropism. Such selection schemes involve harvesting HCV particles from culture supernatants or after cell disruption and selecting for MTX-resistant transducing particles by reinfection of naive cells.

Methods similar to the above can be used to establish adaptive variants with variations in characteristics such as the increased or decreased ability to cause infection, the ability to cause infection in a host that wild-type strains are unable to infect, or cells of such a host.

The invention also provides host cell lines transfected with any of the HCV DNA (or HCV RNA) as set forth above. Examples of host cells include, but are by no means limited to, the group consisting of a bacterial cell, a yeast cell, an insect cell, and a mammalian cell. Preferably, the host cell is capable of providing for expression of functional HCV RNA replicase, virions or virus particle proteins.

In a related aspect, as briefly described above, the invention provides a vector for gene therapy or a gene vaccine (also termed herein a genetic vaccine), in which a heterologous protein is inserted into the HCV nucleic acid under conditions that permit expression of the heterologous protein. These vaccines can be either DNA or RNA. In particular, the invention provides an infectious hepatitis C virus (HCV) DNA vector comprising from 5' to 3' on the positive-sense DNA, a promoter; an HCV 5'-non-translated region (NTR) containing the extreme 5'-terminal sequence GCCAGCC; an HCV polyprotein coding region comprising a coding region for a heterologous gene; and a 3' non-translated region (NTR). Preferably, the promoter is selected from the group consisting of bacteriophage T3, T7, and SP6.

In the embodiments of the invention where the functional HCV nucleic acid is DNA, it may further comprise a promoter operatively associated with the 5' NTR. For example, but not by way of limitation, the promoter may be selected from the group consisting of bacteriophage T7, T3, and SP6. However, any suitable promoter for transcription of HCV genomic RNA corresponding to the HCV DNA can be used, depending on the specific transcription system employed. For example, for nuclear transcription (e.g., in an animal transgenic for HCV), an endogenous or viral promoter, such as CMV, may be used. Additionally, these promoter-driven HCV DNAs can be incorporated into an extrachromosomally replicating DNA such as a plasmid or a phage.

Various uses of the invention variants are envisioned herein. Uses relevant to therapy and vaccine development include: (i) the generation of defined HCV virus stocks to develop in vitro and in vivo assays for virus neutralization, attachment, penetration and entry; (ii) structure/function studies on HCV proteins and RNA elements and identification of new antiviral targets; (iii) a systematic survey of cell culture systems and conditions to identify those that support wild-type and variant HCV RNA replication and particle release; (iv) production of adaptive HCV variants capable of more efficient replication in cell culture; (v) production of HCV variants with altered tissue or species tropism; (vi) establishment of alternative animal models for inhibitor evaluation including those supporting HCV variant replication; (vii) development of cell-free HCV replication assays; (viii) production of immunogenic HCV particles for vaccination; (ix) engineering of attenuated HCV derivatives as possible vaccine candidates; (x) engineering of attenuated or defective HCV derivatives for expression of heterologous gene products for gene therapy and vaccine applications; (xi) utilization of the HCV glycoproteins for targeted delivery of therapeutic agents to the liver or other cell types with appropriate receptors.

The invention further provides a method for infecting an animal with HCV variants, where the method comprises administering an infectious dose of HCV variant RNA prepared by transcription of infectious HCV variant DNA. The invention extends to a non-human animal infected with HCV variants or transfected with HCV variant RNA or DNA. Similarly, the invention provides a method for propagating infectious HCV variants in vitro comprising culturing a cell line contacted with an infectious amount of HCV variant RNA prepared by transcription of the infectious HCV DNA, as well as an in vitro cell line infected with HCV variants. In a specific embodiment, the cell line is a hepatocyte cell line transfected or infected with an HCV variant in which an IRES-antibiotic resistance cassette has been engineered to provide for selection. The variant may also comprise the adaptive mutations described above.

In accordance with the gene therapy (genetic vaccine) embodiment of the invention, also provided is a method for transducing an animal capable of HCV RNA replication with a heterologous gene, comprising administering an amount of an HCV variant RNA prepared by transcription of the HCV variant DNA vector.

In another embodiment, the invention provides a method for producing HCV particle proteins comprising culturing a host expression cell line transfected with an HCV variant of the invention under conditions that permit expression of HCV particle proteins; and isolating HCV particle proteins from the cell culture. In a specific embodiment, such an expression cell line may be a cell selected from the group consisting of a bacterial cell, a yeast cell, an insect cell, and a mammalian cell.

The invention further provides an HCV virion comprising an HCV variant RNA genome. Such virions can be used in an HCV vaccine, preferably after attenuation, e.g., by heat or chemical treatment, or through selection of attenuated variants by the methods described above.

The in vivo and in vitro HCV variants of the invention permits controlled screening for anti-HCV agents (i.e., drugs for treatment of HCV), as well as for evaluation of drug resistance. An in vivo method for screening for agents capable of modulating HCV replication may comprise administering a candidate agent to an animal containing an HCV variant, and testing for an increase or decrease in a level of HCV variant infection, replication or activity compared to a level of HCV variant infection, replication or activity in the animal prior to administration of the candidate agent; wherein a decrease in the level of HCV variant infection, replication or activity compared to the level of HCV variant infection, replication or activity in the animal prior to administration of the candidate agent is indicative of the ability of the agent to inhibit HCV variant infection, replication or activity. Testing for the level of HCV variant infection or replication can involve measuring the viral titer (e.g., RNA levels) in a serum or tissue sample from the animal; testing for the level of HCV variant activity can involve measuring liver enzymes. Alternatively, an in vitro method for screening for agents capable of modulating HCV replication can comprise contacting a cell line supporting a replicating HCV variant with a candidate agent; and thereafter testing for an increase or decrease in a level of HCV variant replication or activity compared to a level of HCV variant replication or activity in a control cell line or in the cell line prior to administration of the candidate agent, wherein a decrease in the level of HCV variant replication or activity compared to the level of HCV variant replication or activity in a control cell line or in the cell line prior to administration of the candidate agent is indicative of the ability of the agent to inhibit HCV variant replication or activity. In a specific embodiment, testing for the level of HCV variant replication in vitro may involve measuring the HCV titer, (e.g., RNA levels) in the cell culture; testing for the level of HCV activity in vitro may involve measuring HCV replication.

In addition to the specific HCV variant DNA clones and related HCV variant RNAs, the invention is directed to a method for preparing an HCV variant DNA clone that is capable of replication in a host or host cell line, comprising joining from 5' to 3' on the positive-sense DNA a promoter; an HCV 5' non-translated region (NTR) an HCV polyprotein coding region; and a 3' non-translated region (NTR), where at least one of these regions is not a naturally occurring region. Preferably, the promoter is selected from the group consisting of bacteriophage T7, T3, and SP6. In a specific embodiment, the extreme 5'-terminal sequence is homologous to SEQ ID NO:1, e.g., the 5'-terminal sequence may be selected from the group consisting of GCCAGCC; GGCCAGCC; UGCCAGCC; AGCCAGCC; AAGCCAGCC; GAGCCAGCC; GUGCCAGCC; and GCGCCAGCC, wherein the sequence GCCAGCC is the 5'-terminus of SEQ ID NO:1.

The 3'-NTR poly-U for use in the method of preparing an HCV variant DNA clone may include a long poly-U region. Similarly, the 3'-NTR extreme terminus may be RNA homologous to a DNA having the sequence 5'-TGGTG-GCTCCATCTTAGCCCTAGTCACG-GCTAGCTGTGAAAGGTCCGTGAGCC GCATGACTG-CAGAGAGTGCTGATACTGGCCTCTCTGCTGATCATGT-3' (SEQ ID NO:2); in a specific embodiment, the 3'-NTR extreme terminus has the foregoing sequence.

Components of functional HCV variant DNA clones. Components of the functional HCV variant DNA described in this invention can be used to develop cell-free, cell culture, and animal-based screening assays for known or newly identified HCV antiviral targets as described infra. For each selected target, it is preferred that the HCV variant used has the wild-type form of the target. Examples of known or suspected targets and assays include [see Houghton, In "Fields Virology" (B. N. Fields, D. M. Knipe and P. M. Howley, Eds.), Vol. pp. 1035-1058. Raven Press, New York (1996); Rice, (1996) supra; Rice et al., *Antiviral Therapy* 1, Suppl. 4, 11-17 (1997); Shimotohno, *Hepatology* 21,:887-8 (1995) for reviews], but are not limited to, the following:

The highly conserved 5' NIR, which contains elements essential for translation of the incoming HCV genome RNA, is one target. It is also likely that this sequence, or its complement, contains RNA elements important for RNA replication and/or packaging. Potential therapeutic strategies include: antisense oligonucleotides (supra); trans-acting ribozymes (supra); RNA decoys; small molecule compounds interfering with the function of this element (these could act by binding to the RNA element itself or to cognate viral or cellular factors required for activity).

Another target is the HCV C (capsid or core) protein, which is highly conserved and is associated with the following functions: RNA binding and specific encapsidation of HCV genome RNA; transcriptional modulation of cellular [Ray et al., *Virus Res.* 37: 209-220 (1995)] and other viral [Shih et al., *J. Virol.* 69: 1160-1171 (1995); Shih et al., *J. Virol.* 67: 5823-5832 (1993)] genes; binding of cellular helicase [You et al., *J. Virol.* 73:2841-2853 (1999)]; cellular transformation [Ray et al., *J. Virol.* 70: 4438-4443 (1996a); Ray et al., *J. Biol. Chem.* 272:10983-10986(1997)]; prevention of apoptosis [Ray et al., *Virol.* 226: 176-182 (1996b)]; modulation of host immune response through binding to members of the TNF receptor superfamily [Matsumoto et al., *J. Virol.* 71: 1301-1309 (1997)].

The E1, E2, and perhaps the E2-p7 glycoproteins that form the components of the virion envelope are targets for potentially neutralizing antibodies. Key steps where intervention can be targeted include: signal peptidase mediated cleavage of these precursors from the polyprotein [Lin et al., (1994a) supra]; ER assembly of the E1E2 glycoprotein complex and association of these proteins with cellular chaperones and folding machinery [Dubuisson et al., (1994) supra; Dubuisson and Rice, *J. Virol.* 70: 778-786 (1996)]; assembly of virus particles including interactions between the nucleocapsid and virion envelope; transport and release of virus particles; the association of virus particles with host components such as VLDL [Hijikata et al., (1993) supra; Thomssen et al., (1992) supra; Thomssen et al., *Med. Microbiol. Immunol.* 182: 329-334 (1993)] which may play a role in evasion of immune surveillance or in binding and entry of cells expressing the LDL receptor; conserved and variable determinants in the virion which are targets for neutralization by antibodies or which bind to antibodies and facilitate immune-enhanced infection of cells via interaction with cognate Fc receptors; conserved and variable determinants in the virion important for receptor binding and entry; virion determinants participating in entry, fusion with cellular membranes, and uncoating the incoming viral nucleocapsid.

The NS2-3 autoprotease, which is required for cleavage at the 2/3 site is a further target.

The NS3 serine protease and NS4A cofactor which form a complex and mediate four cleavages in the HCV polyprotein [see Rice, (1997) supra for review) is yet another suitable target. Targets include the serine protease activity itself; the tetrahedral $Zn^{2+}$ coordination site in the C-terminal domain of the serine protease; the NS3-NS4A cofactor interaction; the membrane association of NS4A; stabilization of NS3 by NS4A; transforming potential of the NS3 protease region [Sakamuro et al., *J. Virol* 69: 3893-6 (1995)].

The NS3 RNA-stimulated NTPase [Suzich et al., (1993) supra], RNA helicase [Jin and Peterson, *Arch Biochem Biophys* 323: 47-53 (1995); Kim et al., *Biochem. Biophys. Res. Commun.* 215: 160-6 (1995)], and RNA binding [Kanai et al., *FEBS Lett* 376: 221-4 (1995)] activities; the NS4A protein as a component of the RNA replication complex is another potential target.

The NS5A protein, another replication component, represents another target. This protein is phosphorylated predominantly on serine residues [Tanji et al., *J. Virol.* 69: 3980-3986 (1995)]. Transcription modulating, cell growth promoting, and apoptosis inhibiting activities of NS5A [Ghosh et al., *J. Biol. Chem.* 275:7184-7188 (2000)] can be targeted. Other characteristics of NS5A that could be targets for therapy include the kinase responsible for NS5A phosphorylation and its interaction with NS5A, and the interaction with NS5A and other components of the HCV replication complex.

The NS5B RNA-dependent RNA polymerase, which is the enzyme responsible for the actual synthesis of HCV positive and negative-strand RNAs, is another target. Specific aspects of its activity include the polymerase activity itself [Behrens et al., *EMBO J.* 15: 12-22 (1996)]; interactions of NS5B with other replicase components, including the HCV RNAs; steps involved in the initiation of negative- and positive-strand RNA synthesis; phosphorylation of NS5B [Hwang et al., *Virology* 227:438 (1997)].

Other targets include structural or nonstructural protein functions important for HCV RNA replication and/or modulation of host cell function. Possible hydrophobic protein components capable of forming channels important for viral entry, egress or modulation of host cell gene expression may be targeted.

The 3' NTR, especially the highly conserved elements (poly (U/UC) tract; 98-base terminal sequence) can be targeted. Therapeutic approaches parallel those described for the 5' NTR, except that this portion of the genome is likely to play a key role in the initiation of negative-strand synthesis. It may also be involved in other aspects of HCV RNA replication, including translation, RNA stability, or packaging.

The functional HCV variants of the present invention may encode all of the viral proteins and RNA elements required for RNA packaging. These elements can be targeted for development of antiviral compounds. Electrophoretic mobility shift, UV cross-linking, filter binding, and three-hybrid [SenGupta et al., Proc. Natl. Acad. Sci. USA 93: 8496-8501 (1996)] assays can be used to define the protein and RNA elements important for HCV RNA packaging and to establish assays to screen for inhibitors of this process. Such inhibitors might include small molecules or RNA decoys produced by selection in vitro [Gold et al., (1995) supra].

Complex libraries of the variants of the present invention can be prepared using PCR shuffling, or by incorporating randomized sequences, such as are generated in "peptide display" libraries. Using the "phage method" [Scott and Smith, 1990, Science 249:386-390 (1990); Cwirla, et al., Proc. Natl. Acad. Sci USA., 87:6378-6382 (1990); Devlin et al., Science, 249:404-406 (1990)], very large libraries can be constructed ($10^6$-$10^8$ chemical entities). Clones from such libraries can be used to generate other variants or chimeras, e.g., using various HCV subtypes. Such variants can be generated by methods known in the art, without undue experimentation.

A clone that includes a primer and run-off sequence can be used directly for production of functional HCV variant RNA. A large number of vector-host systems known in the art may be used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, pTET, etc. As is well known, the insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired could be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

Expression of HCV RNA and Polypeptides

The HCV variant DNA, which codes for HCV variant RNA and HCV proteins, particularly HCV RNA replicase or virion proteins, can be inserted into an appropriate expression vector, i.e., a vector which contains the necessary elements for the transcription and translation of the inserted protein-coding sequence. Such elements are termed herein a "promoter." Thus, the HCV variant DNA of the invention is operationally (or operably) associated with a promoter in an expression vector of the invention. An expression vector also preferably includes a replication origin. The necessary transcriptional and translational signals can be provided on a recombinant expression vector. In a preferred embodiment for in vitro synthesis of functional RNAs, the T7, T3, or SP6 promoter is used.

Potential host-vector systems include but are not limited to mammalian cell systems infected with virus recombinant (e.g., vaccinia virus, adenovirus, Sindbis virus, Semliki Forest virus, etc.); insect cell systems infected with recombinant viruses (e.g., baculovirus); microorganisms such as yeast containing yeast vectors; plant cells; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The cell into which the recombinant vector comprising the HCV variant DNA clone has been introduced is cultured in an appropriate cell culture medium under conditions that provide for expression of HCV RNA or such HCV proteins by the cell. Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of HCV variant RNA or protein may be controlled by any promoter/enhancer element known in the art, but these regulatory elements must be functional in the host selected for expression. Promoters which may be used to control expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX [Smith et al., 1988, Gene 67:31-40], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like known in the art.

In addition to the preferred sequencing analysis, expression vectors containing an HCV variant DNA clone of the invention can be identified by four general approaches: (a) PCR amplification of the desired plasmid DNA or specific mRNA, (b) nucleic acid hybridization, (c) presence or absence of selection marker gene functions, (d) analysis with appropriate restriction endonucleases and (e) expression of inserted sequences. In the first approach, the nucleic acids can be amplified by PCR to provide for detection of the amplified product. In the second approach, the presence of nucleic acids in an expression vector can be detected by nucleic acid hybridization using probes comprising sequences that are homologous to the HCV variant DNA. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In the fourth approach, recombinant expression vectors are identified by digestion with appropriate restriction enzymes. In the fifth approach, recombinant expression vectors can be identified by assaying for the activity, biochemical, or immunological characteristics of the gene product expressed by the recombinant, e.g., HCV RNA, HCV virions, or HCV viral proteins.

For example, in a baculovirus expression systems, both non-fusion transfer vectors, such as but not limited to pVL941 (BamHI cloning site; Summers), pVL1393 (BamHI, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamHI cloning site; Summers and Invitrogen), and pBlueBacIII (BamHI, BglII, PstI, NcoI, and HindIII cloning site, with blue/white recombinant screening possible; Invitrogen), and fusion transfer vectors, such as but not limited to pAc700 (BamHI and KpnI cloning site, in which the BamHI recognition site begins with the initiation codon; Summers), pAc701 and pAc702 (same as pAc700, with different reading frames), pAc360 (BamHI cloning site 36 base pairs downstream of a polyhedrin initiation codon; Invitrogen (195)), and pBlueBacHisA, B, C (three different reading frames, with BamHI, BglII, PstI, NcoI, and HindIII cloning site, an N-terminal peptide for ProBond purification, and blue/white recombinant screening of plaques; Invitrogen) can be used.

Examples of mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR); [see Kaufman, *Current Protocols in Molecular Biology*, 16.12 (1991)]. Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamHI cloning site, inducible methallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Regulatable mammalian expression vectors, can be used, such as Tet and rTet [Gossen and Bujard, *Proc. Natl. Acad. Sci. USA* 89:5547-51 (1992); Gossen et al., *Science* 268: 1766-1769 (1995)]. Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors [see, Kaufman (1991) supra] for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Examples of yeast expression systems include the non-fusion pYES2 vector (XbaI, SphI, ShoI, NotI, GstXI, EcoRI, BstXI, BamHI, SacI, KpnI, and HindIII cloning sit; Invitrogen) or the fusion pYESHisA, B, C (XbaI, SphI, ShoI, NotI, BstXI, EcoRI, BamHI, SacI, KpnI, and HindIII cloning site, N-terminal peptide purified with ProBond resin and cleaved with enterokinase; Invitrogen), to mention just two, can be employed according to the invention.

In addition, a host cell strain may be chosen that modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Expression in yeast can produce a glycosylated product. Expression in eukaryotic cells can increase the likelihood of "native" glycosylation and folding of an HCV protein. Moreover, expression in mammalian cells can provide a tool for reconstituting, or constituting, native HCV virions or virus particle proteins.

A variety of transfection methods, useful for other RNA virus studies, can be utilized herein without undue experimentation. Examples include microinjection, cell fusion, calcium-phosphate cationic liposomes such as lipofectin [Rice et al., *New Biol.* 1:285-296 (1989); see "HCV-based Gene Expression Vectors", infra], DE-dextran [Rice et al., *J. Virol.* 61: 3809-3819 (1987)], and electroporation [Bredenbeek et al., *J. Virol.* 67: 6439-6446 (1993); Liljeström et al., *J. Virol.* 65: 4107-4113 (1991)]. Scrape loading [Kumar et al., *Biochem. Mol. Biol. Int.* 32: 1059-1066 (1994)] and ballistic methods [Burkholder et al., *J. Immunol. Meth.* 165: 149-156 (1993)] may also be considered for cell types refractory to transfection by these other methods. A DNA vector transporter may be considered [see, e.g., Wu et al., 1992, J. Biol. Chem. 267:963-967; Wu and Wu, 1988, J. Biol. Chem. 263: 14621-14624; Hartmut et al., Canadian Patent Application No. 2,012,311, filed Mar. 15, 1990].

In vitro Transfection with HCV Variants

Identification of cell lines supporting HCV replication. An important aspect of the invention is a method it provides for developing new and more effective anti-HCV therapy by conferring the ability to evaluate the efficacy of different therapeutic strategies using an authentic and standardized in vitro HCV variant replication system. Such assays are invaluable before moving on to trials using rare and valuable experimental animals, such as the chimpanzee, or HCV-infected human patients. The adaptive variants of the invention are particularly useful for this work because their growth in culture and their ability to withstand subpassage is superior to wild-type strains. Also, the replicons disclosed herein are useful because replication can be evaluated without the confounding effects of the structural proteins.

The HCV variant infectious clone technology can also be used to establish in vitro and in vivo systems for analysis of HCV replication and packaging. These include, but are not restricted to, (i) identification or selection of permissive cell types (for RNA replication, virion assembly and release); (ii) investigation of cell culture parameters (e.g., varying culture conditions, cell activation, etc.) or selection of adaptive mutations that increase the efficiency of HCV replication in cell cultures; and (iii) definition of conditions for efficient production of infectious HCV variant particles (either released into the culture supernatant or obtained after cell disruption). These and other readily apparent extensions of the invention have broad utility for HCV therapeutic, vaccine, and diagnostic development.

General approaches for identifying permissive cell types are outlined below. Optimal methods for RNA transfection (see also, supra) vary with cell type and are determined using RNA reporter constructs. These include, for example, the bicistronic replicons disclosed supra and in the Examples, and bicistronic virus [Wang et al., *J. Virol.* 67: 3338-44 (1993)] with the structure 5'-CAT-HCV IRES-LUC-3'. These HCV variants are used both to optimize transfection conditions (using, e.g., by measuring β-galactosidase or CAT [chloramphenicol acetyltransferase] activity to determine transfection efficiency) and to determine if the cell type is permissive for HCV IRES-mediated translation (e.g., by measuring LUC; luciferase activity). For actual HCV RNA transfection experiments, cotransfection with a 5' capped luciferase reporter RNA [Wang et al., (1993) supra] provides an internal standard for productive transfection and translation. Examples of cell types potentially permissive for HCV replication include, but are not restricted to, primary human cells (e.g., hepatocytes, T-cells, B-cells, foreskin fibroblasts) as well as continuous human cell lines (e.g., HepG2, Huh7, HUT78, HPB-Ma, MT-2, MT-2C, and other HTLV-1 and HTLV-II infected T-cell lines, Namalawa, Daudi, EBV-transformed LCLs). In addition, cell lines of other species, especially those which are readily transfected with RNA and permissive for replication of flaviviruses or pestiviruses (e.g., SW-13, Vero, BHK-21, COS, PK-15, MBCK, etc.), can be tested. Cells are transfected using a method as described supra.

For replication assays, RNA transcripts are prepared using the HCV variant and the corresponding non-functional, e.g., ΔGDD (see Examples) derivative as a negative control, for persistence of HCV RNA and antigen in the absence of productive replication. Template DNA (which complicates later analyses) is removed by repeated cycles of DNaseI treatment and acid phenol extraction followed by purification by either gel electrophoresis or gel filtration, to preferably achieve less than one molecule of amplifiable DNA per $10^9$ molecules of transcript RNA. DNA-free RNA transcripts are mixed with LUC reporter RNA and used to transfect cell cultures using optimal conditions determined above. After recovery of the cells, RNaseA is added to the media to digest excess input RNA and the cultures incubated for various periods of time. An early timepoint (~1 day post-transfection) will be harvested and analyzed for LUC activity (to verify productive transfection) and positive-strand RNA levels in the cells and supernatant (as a baseline). Samples are collected periodically for 2-3 weeks and assayed for positive-strand RNA levels by QC-RT/PCR [see Kolykhalov et al., (1996) supra]. Cell types showing a clear and reproducible difference between the intact infectious transcript and the non-functional derivative, e.g., ΔGDD deletion, control can be subjected to more thorough analyses to verify authentic replication. Such assays include measurement of negative-sense HCV RNA accumulation by QC-RT/PCR [Gunji et al., (1994) supra; Lanford et al., *Virology* 202: 606-14 (1994)], Northern-blot hybridization, or metabolic labeling [Yoo et al., (1995) supra] and single cell methods, such as in situ hybridization [ISH; Gowans et al., In "Nucleic Acid Probes" (R. H. Symons, Eds.), Vol. pp. 139-158. CRC Press, Boca Raton. (1989)], in situ PCR [followed by ISH to detect only HCV-specific amplification products; Haase et al., *Proc. Natl. Acad. Sci. USA* 87: 4971-4975 (1990)], and immunohistochemistry.

HCV particles for studying virus-receptor interactions. In combination with the identification of cell lines that are permissive for HCV replication, defined HCV variant stocks can be used to evaluate the interaction of the HCV with cellular receptors. Assays can be set up which measure binding of the virus to susceptible cells or productive infection, and then used to screen for inhibitors of these processes.

Identification of cell lines for characterization of HCV receptors. Cell lines permissive for HCV RNA replication, as assayed by RNA transfection, can be screened for their ability to be infected by the virus using the HCV variants of the present invention. Cell lines permissive for RNA replication but which cannot be infected by the homologous virus may lack one or more host receptors required for HCV binding and entry. Such cells provide valuable tools for (i) functional identification and molecular cloning of HCV receptors and co-receptors; (ii) characterization of virus-receptor interactions; and (iii) developing assays to screen for compounds or biologics (e.g., antibodies, SELEX RNAs [Bartel and Szostak, In "RNA-protein interactions" (K. Nagai and I. W. Mattaj, Eds.), Vol. pp. 82-102. IRL Press, Oxford (1995); Gold et al., *Annu. Rev. Biochem.* 64: 763-797 (1995)], etc.) that inhibit these interactions. Once defined in this manner, these HCV receptors serve not only as therapeutic targets but may also be expressed in transgenic animals rendering them susceptible to HCV infection [Koike et al., *Dev Biol Stand* 78: 101-7 (1993); Ren and Racaniello, *J Virol* 66: 296-304 (1992)]. Such transgenic animal models supporting HCV replication and spread have important applications for evaluating anti-HCV drugs.

The ability to manipulate the HCV glycoprotein structure may also be used to create HCV variants with altered receptor specificity. In one example, HCV glycoproteins can be modified to express a heterologous binding domain for a known cell surface receptor. The approach should allow the engineering of HCV derivatives with altered tropism and perhaps extend infection to non-chimeric small animal models.

Alternative approaches for identifyingpermissive cell lines. As previously discussed, and as exemplified in the Examples, fumctional HCV variants can be engineered that comprise selectable markers for HCV replication. For instance, genes encoding dominant selectable markers can be expressed as part of the HCV polyprotein, or as separate cistrons located in permissive regions of the HCV RNA genome.

Animal Models for HCV Infection and Replication

In addition to chimpanzees, the present invention permits development of alternative animal models for studying HCV replication and evaluating novel therapeutics. Using clones of the authentic HCV variants described in this invention as starting material, multiple approaches can be envisioned for establishing alternative animal models for HCV replication. In one manifestation, the variants could be used to inoculate immunodeficient mice harboring human tissues capable of supporting HCV replication. An example of this art is the SCID:Hu mouse, where mice with a severe combined immunodeficiency are engrafted with various human (or chimpanzee) tissues, which could include, but are not limited to, fetal liver, adult liver, spleen, or peripheral blood mononuclear cells. Besides SCID mice, normal irradiated mice can serve as recipients for engraftment of human or chimpanzee tissues. These chimeric animals would then be substrates for HCV replication after either ex vivo or in vivo infection with defined virus-containing inocula.

In another manifestation, adaptive mutations allowing HCV replication in alternative species may produce variants that are permissive for replication in these animals. For instance, adaptation of HCV for replication and spread in either continuous rodent cell lines or primary tissues (such as hepatocytes) could enable the virus to replicate in small rodent models. Alternatively, complex libraries of HCV variants created by DNA shuffling [Stemmer, *Proc. Natl. Acad. Sci. USA* 91:10747 (1994)] or other methods known in the art can be created and used for inoculation of potentially susceptible animals. Such animals could be either immunocompetent or immunodeficient, as described above.

The functional activity of HCV variants can be evaluated transgenically. In this respect, a transgenic mouse model can be used [see, e.g., Wilmut et al., *Experientia* 47:905 (1991)]. The HCV RNA or DNA clone can be used to prepare transgenic vectors, including viral vectors, plasmid or cosmid clones (or phage clones). Cosmids may be introduced into transgenic mice using published procedures [Jaenisch, *Science*, 240:1468-1474 (1988)]. In the preparation of transgenic mice, embryonic stem cells are obtained from blastocyst embryos [Joyner, *In Gene Targeting: A Practical Approach. The Practical Approach Series*, Rickwood, D., and Hames, B. D., Eds., IRL Press: Oxford (1993)] and transfected with HCV variant DNA or RNA. Transfected cells are injected into early embryos, e.g., mouse embryos, as described [Hammer et al., *Nature* 315:680 (1985); Joyner, supra]. Various techniques for preparation of transgenic animals have been described [U.S. Pat. No. 5,530,177, issued Jun. 25, 1996; U.S. Pat. No. 5,898,604, issued Dec. 31, 1996]. Of particular interest are transgenic animal models in which the phenotypic or pathogenic effects of a transgene are studied. For example, the effects of a rat phosphoenolpyruvate carboxykinase-bovine growth hormone fusion gene has been studied in pigs [Wieghart et al., *J. Reprod. Fert., Suppl.* 41:89-96 (1996)]. Transgenic mice that express of a gene encoding a human amyloid precursor protein associated with Alzheimer's disease are used to study this disease and other disorders [International Patent Publication WO 96/06927, published Mar. 7, 1996; Quon et al., *Nature* 352:239 (1991)]. Transgenic mice have also been created for the hepatitis delta agent [Polo et al., *J. Virol.* 69:5203 (1995)] and for hepatitis B virus [Chisari, *Curr. Top. Microbiol. Immunol.* 206:149 (1996)], and replication occurs in these engineered animals.

Thus, the functional HCV variants described here, or parts thereof, can be used to create transgenic models relevant to HCV replication and pathogenesis. In one example, transgenic animals harboring the entire genome of an HCV variant can be created. Appropriate constructs for transgenic expression of the entire HCV variant genome in a transgenic mouse of the invention could include a nuclear promoter engineered to produce transcripts with the appropriate 5' terminus, the full-length HCV variant cDNA sequence, a cis-cleaving delta ribozyme [Ball, *J. Virol.* 66: 2335-2345 (1992); Pattnaik et al., *Cell* 69: 1011-1020 (1992)] to produce an authentic 3' terminus, followed possibly by signals that promote proper nuclear processing and transport to the cytoplasm (where HCV RNA replication occurs). Besides the entire HCV variant genome, animals can be engineered to express individual or various combinations of HCV proteins and RNA elements. For example, animals engineered to express an HCV gene product or reporter gene under the control of the HCV IRES can be used to evaluate therapies directed against this specific RNA target. Similar animal models can be envisioned for most known HCV targets.

Such alternative animal models are useful for (i) studying the effects of different antiviral agents on replication of HCV variants, including replicons, in a whole animal system; (ii) examining potential direct cytotoxic effects of HCV gene products on hepatocytes and other cell types, defining the underlying mechanisms involved, and identifying and testing strategies for therapeutic intervention; and (iii) studying immune-mediated mechanisms of cell and tissue damage relevant to HCV pathogenesis and identifying and testing strategies for interfering with these processes.

Selection and Analysis of Drug-Resistant Variants

Cell lines and animal models supporting HCV replication can be used to examine the emergence of HCV variants with resistance to existing and novel therapeutics. Like all RNA viruses, the HCV replicase is presumed to lack proofreading activity and RNA replication is therefore error prone, giving rise to a high level of variation [Bukh et al., (1995) supra]. The variability manifests itself in the infected patient over time and in the considerable diversity observed between different isolates. The emergence of drug-resistant variants is likely to be an important consideration in the design and evaluation of HCV mono and combination therapies. HCV replication systems of the invention can be used to study the emergence of variants under various therapeutic formulations. These might include monotherapy or various combination therapies (e.g., IFN-α, ribavirin, and new antiviral compounds). Resistant mutants can then be used to define the molecular and structural basis of resistance and to evaluate new therapeutic formulations, or in screening assays for effective anti-HCV drugs (infra).

Screening for Anti-HCV Agents

HCV-permissive cell lines or animal models (preferably rodent models) comprising adaptive HCV variants can be used to screen for novel inhibitors or to evaluate candidate anti-HCV therapies. Such therapies include, but would not be limited to, (i) antisense oligonucleotides or ribozymes targeted to conserved HCV RNA targets; (ii) injectable compounds capable of inhibiting HCV replication; and (iii) orally bioavailable compounds capable of inhibiting HCV replication. Targets for such formulations include, but are not restricted to, (i) conserved HCV RNA elements important for RNA replication and RNA packaging; (ii) HCV-encoded enzymes; (iii) protein-protein and protein-RNA interactions important for HCV RNA replication, virus assembly, virus release, viral receptor binding, viral entry, and initiation of viral RNA replication; (iv) virus-host interactions modulating the ability of HCV to establish chronic infections; (v) virus-host interactions modulating the severity of liver damage, including factors affecting apoptosis and hepatotoxicity; (vi) virus-host interactions leading to the development of more severe clinical outcomes including cirrhosis and hepatocellular carcinoma; and (vii) virus-host interactions resulting in other, less frequent, HCV-associated human diseases.

Evaluation of antisense and ribozyme therapies. The present invention extends to the preparation of antisense nucleotides and ribozymes that may be tested for the ability to interfere with HCV replication. This approach utilizes antisense nucleic acid and ribozymes to block translation of a specific MRNA, either by masking that mRNA with an antisense nucleic acid or cleaving it with a ribozyme.

Antisense nucleic acids are DNA or RNA molecules that are complementary to at least a portion of a specific MRNA molecule. Reviews of antisense technology include: Baertschi, *Mol. Cell. Endocrinol.* 101:R15-R24 (1994); Crooke et al., *Annu. Rev. Pharmacol. Toxicol.* 36:107-129 (1996); Alama et al., *Pharmacol. Res*. 36:171-178; and Boyer et al., *J. Hepatol*. 32(1 Suppl):98-112(2000). The last review discusses antisense technology as it applies to HCV.

In the cell, they hybridize to that mRNA, forming a double stranded DNA:RNA or RNA:RNA molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro. Preferably synthetic antisense nucleotides contain phosphoester analogs, such as phosphorothiolates, or thioesters, rather than natural phophoester bonds. Such phosphoester bond analogs are more resistant to degradation, increasing the stability, and therefore the efficacy, of the antisense nucleic acids.

In the genetic antisense approach, expression of the wild-type allele is suppressed because of expression of antisense RNA. This technique has been used to inhibit TK synthesis in tissue culture and to produce phenotypes of the Kruppel mutation in *Drosophila*, and the Shiverer mutation in mice [Izant et al., *Cell*, 36:1007-1015 (1984); Green et al., *Annu. Rev. Biochem*., 55:569-597 (1986); Katsuki et al., *Science*, 241:593-595 (1988)]. An important advantage of this approach is that only a small portion of the gene need be expressed for effective inhibition of expression of the entire cognate mRNA. The antisense transgene will be placed under control of its own promoter or another promoter expressed in the correct cell type, and placed upstream of the SV40 polyA site.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it. Recent reviews include Shippy et al., *Mol. Biotechnol*. 12:117-129 (1999); Schmidt, *Mol. Cells* 9:459-463 (1999); Phylactou et al., *Meth. Enzymol*. 313:485-506 (2000); Oketani et al., *J. Hepatol*. 31:628-634 (1999); Macejak et al., *Hepatology* 31:769-776 (2000). The last two references disclose the use of ribozymes for inhibiting HCV. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to *Tetrahymena*-type ribozymes for inactivating a specific mRNA species, and eighteen base recognition sequences are preferable to shorter recognition sequences.

Screening compound libraries for anti-HCV activity. Various natural product or synthetic libraries can be screened for anti-HCV activity in the in vitro or in vivo models comprising HCV variants as provided by the invention. One approach to preparation of a combinatorial library uses primarily chemical methods, of which the Geysen method [Geysen et al., *Molecular Immunology* 23:709-715 (1986); Geysen et al. *J. Immunologic Method* 102:259-274 (1987)] and the method of Fodor et al. [*Science* 251:767-773 (1991)] are examples. Furka et al. [*14th International Congress of Biochemistry, Volume* 5, Abstract FR:013 (1988); Furka, *Int. J. Peptide Protein Res*. 37:487-493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested for anti-HCV activity.

In another aspect, synthetic libraries [Needels et al., *Proc. Natl. Acad. Sci. USA* 90:10700-4 (1993); Ohlmeyer et al., *Proc. Natl. Acad. Sci. USA* 90:10922-10926 (1993); Lam et al., International Patent Publication No. WO 92/00252; Kocis et al., International Patent Publication No. WO 9428028], and the like can be used to screen for anti-HCV compounds according to the present invention. The references describe adaption of the library screening techniques in biological assays.

Defined/engineered HCVvariant virus particles for neutralization assays. The variants described herein can be used to produce defined stocks of HCV particles for infectivity and neutralization assays. Homogeneous stocks can be produced in the chimpanzee model, in cell culture systems, or using various heterologous expression systems (e.g., baculovirus, yeast, mammalian cells; see supra). These stocks can be used in cell culture or in vivo assays to define molecules or gene therapy approaches capable of neutralizing HCV particle production or infectivity. Examples of such molecules include, but are not restricted to, polyclonal antibodies, monoclonal antibodies, artificial antibodies with engineered/optimized specificity, single-chain antibodies (see the section on antibodies, infra), nucleic acids or derivatized nucleic acids selected for specific binding and neutralization, small orally bioavailable compounds, etc. Such neutralizing agents, targeted to conserved viral or cellular targets, can be either genotype or isolate-specific or broadly cross-reactive. They could be used either prophylactically or for passive immunotherapy to reduce viral load and perhaps increase the chances of more effective treatment in combination with other antiviral agents (e.g., IFN-α, ribavirin, etc.). Directed manipulation of HCV infectious clones can also be used to produce HCV stocks with defined changes in the glycoprotein hypervariable regions or in other epitopes to study mechanisms of antibody neutralization, CTL recognition, immune escape and immune enhancement. These studies will lead to identification of other virus-specific functions for anti-viral therapy.

Dissection of HCV Replication

Other HCV replication assays. This invention allows directed molecular genetic dissection of HCV replication. Such analyses are expected to (i) validate antiviral targets which are currently being pursued; and (ii) uncover unexpected new aspects of HCV replication amenable to therapeutic intervention. Targets for immediate validation through mutagenesis studies include the following: the 5' NTR, the HCV polyprotein and cleavage products, and the 3' NTR. As described above, analyses using the HCV variants and permissive cell cultures can be used to compare parental and mutant replication phenotypes after transfection of cell cultures with infectious RNA. Even though RT-PCR allows sensitive detection of viral RNA accumulation, mutations which decrease the efficiency of RNA replication may be difficult to analyze, unless conditional mutations are recovered. As a complement to first cycle analyses, trans-complementation assays can be used to facilitate analysis of HCV mutant phenotypes and inhibitor screening. Chimeric variants comprising portions of heterologous systems (vaccinia, Sindbis, or non-viral) can be used to drive expression of the HCV RNA replicase proteins and/or packaging machinery [see Lemm and Rice, *J. Virol*. 67: 1905-1915 (1993a); Lemm and Rice, *J. Virol*. 67: 1916-1926 (1993b); Lemm et al., *EMBO J*. 13: 2925-2934 (1994); Li et al., *J. Virol*. 65: 6714-6723 (1991)]. If these elements are capable of functioning in trans, then co-expression of RNAs with appropriate cis-elements should result in RNA replication/packaging. Such systems therefore mimic steps in authentic RNA replication and virion assembly, but uncouple production of viral components from HCV replication. If HCV replication is somehow self-limiting, heterologous systems may drive significantly higher levels of RNA replication or particle production, facilitating analysis of mutant phenotypes and antiviral screening. A third approach is to devise cell-free systems for HCV template-dependent RNA replication. A coupled translation/replication and assembly system has been described for poliovirus in HeLa cells [Barton and Flanegan, *J. Virol*. 67: 822-831 (1993); Molla et al., *Science* 254: 1647-1651 (1991)], and a template-dependent in vitro assay for initiation of negative-strand synthesis has been established for Sindbis virus. Similar in vitro systems using HCV variants are invaluable for studying many aspects of HCV replication as well as for inhibitor screening and evaluation. An example of each of these strategies follows.

Trans-complementation of HCV RNA replication and/or packaging using viral or non-viral expression systems. Heterologous systems can be used to drive HCV replication. For example, the vaccinia/T7 cytoplasmic expression system has been extremely useful for trans-complementation of RNA virus replicase and packaging functions [see Ball, (1992) supra; Lemm and Rice, (1993a) supra; Lemm and Rice, (1993b) supra; Lemm et al., (1994) supra; Pattnaik et al., (1992) supra; Pattnaik et al., *Virology* 206: 760-4 (1995); Porter et al., *J. Virol*. 69: 1548-1555 (1995)]. In brief, a vaccinia recombinant (vTF7-3) is used to express T7 RNA polymerase (T7RNApol) in the cell type of interest. Target cDNAs, positioned downstream from the T7 promoter, are delivered either as vaccinia recombinants or by plasmid transfection. This system leads to high level RNA and protein expression. A variation of this approach, which obviates the need for vaccinia (which could interfere with HCV RNA replication or virion formation), is the pT7T7 system where the T7 promoter drives expression of T7RNApol [Chen et al., *Nucleic Acids Res*. 22: 2114-2120. (1994)]. pT7T7 is mixed with T7RNApol (the protein) and co-transfected with the T7-driven target plasmid of interest. Added T7RNApol initiates transcription, leading to it own production and high level expression of the target gene. Using either approach, RNA transcripts of variants with precise 5' and 3' termini can be produced using the T7 transcription start site (5') and the cis-cleaving HCV ribozyme (Rz) (3') [Ball, (1992) supra; Pattnaik et al., (1992) supra].

These or similar expression systems can be used to establish assays for HCV RNA replication and particle formation using HCV variants, and for evaluation of compounds which might inhibit these processes. T7-driven protein expression constructs and full-length HCV variants incorporating the HCV ribozyme following the 3' NTR can also be used. A typical experimental plan to validate the assay as described for pT7T7, although essentially similar assays can be envisioned using vTF7-3 or cell lines expressing the T7 RNA polymerase. HCV-permissive cells are co-transfected with pT7T7+T7RNApol+p90/HCVFLlong pU Rz (or a negative control, such as ΔGDD). At different times post-transfection, accumulation of HCV proteins and RNAs, driven by the pT7T7 system, are followed by Western and Northern blotting, respectively. To assay for HCV-specific replicase function, actinomycin D is added to block DNA-dependent T7 transcription [Lemm and Rice, (1993a), supra] and actinomycin D-resistant RNA synthesis is monitored by metabolic labeling. Radioactivity will be incorporated into full-length HCV RNAs for p90/HCVFL long pU/Rz, but not for p90/HCVFLΔGDD/Rz. Using HCV variants of the invention, this assay system, or elaborated derivatives, can be used to screen for inhibitors and to study their effects on HCV RNA replication.

Cell-free systems for assaying HCV replication and inhibitors thereof. Cell-free assays for studying HCV RNA replication and inhibitor screening can also be established using the variants described in this invention. Either virion or transcribed RNAs are used as substrate RNA. For HCV, full-length HCV variant RNAs transcribed in vitro can be used to program such in vitro systems and replication assayed essentially as described for poliovirus [see Barton et al., (1995) supra]. In case hepatocyte-specific or other factors are required for HCV variant RNA replication, the system can be supplemented with hepatocyte or other cell extracts, or alternatively, a comparable system can be established using cell lines which have been shown to be permissive for replication of the HCV variants.

One concern about this approach is that proper cell-free synthesis and processing of the HCV polyprotein must occur. Sufficient quantities of properly processed replicase components may be difficult to produce. To circumvent this problem, the T7 expression system can be used to express high levels of HCV replicase components in appropriate cells [see Lemm et al., (1997) supra]. P15 membrane fractions from these cells (with added buffer, $Mg^{2+}$, an ATP regenerating system, and NTPs) should be able to initiate and synthesize full-length negative-strand RNAs upon addition of HCV-specific template RNAs.

Establishment of either or both of the above assays allows rapid and precise analysis of the effects of HCV mutations, host factors, involved in replication and inhibitors of the various steps in HCV RNA replication. These systems will also establish the requirements for helper systems for preparing replication-deficient HCV vectors.

Vaccination and Protective Immunity

There are still many unknown parameters that impact on development of effective HCV vaccines. It is clear in both man and the chimpanzee that some individuals can clear the infection. Also, 10-20% of those treated with IFN or about twice this percentage treated with IFN and ribavirin show a sustained response as evidenced by lack of circulating HCV RNA. Other studies have shown a lack of protective immunity, as evidenced by successful reinfection with both homologous virus as well as with more distantly related HCV types [Farci et al., (1992) supra; Prince et al., (1992) supra]. Nonetheless, chimpanzees immunized with subunit vaccines consisting of E1E2 oligomers and vaccinia recombinants expressing these proteins are partially protected against low dose challenges [Choo et al., *Proc. Natl. Acad. Sci. USA* 91:1294 (1994)]. The HCV variant technology described in this invention has utility not only for basic studies aimed at understanding the nature of protective immune responses against HCV, but also for novel vaccine production methods.

Active immunity against HCV can be induced by immunization (vaccination) with an immunogenic amount of an attenuated or inactivated HCV variant virion, or HCV virus particle proteins, preferably with an immunologically effective adjuvant. An "immunologically effective adjuvant" is a material that enhances the immune response.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA or RNA encoding the antigen into tissues of a subject for expression of the antigen by the cells of the subject's tissue. Such vaccines are termed herein genetic vaccines, DNA vaccines, genetic vaccination, or nucleic acid-based vaccines. Methods of transfection as described above, such as DNA vectors or vector transporters, can be used for DNA vaccines.

DNA vaccines are described, e.g., in International Patent Publication WO 95/20660 and International Patent Publication WO 93/19183, the disclosures of which are hereby incorporated by reference in their entireties. The ability of directly injected DNA that encodes a viral protein or genome to elicit a protective immune response has been demonstrated in numerous experimental systems [Conry et al., *Cancer Res.*, 54:1164-1168 (1994); Cox et al., *Virol*, 67:5664-5667 (1993); Davis et al., *Hum. Mole. Genet.*, 2:1847-1851 (1993); Sedegah et al., *Proc. Natl. Acad. Sci.*, 91:9866-9870 (1994); Montgomery et al., *DNA Cell Bio.*, 12:777-783 (1993); Ulmer et al., *Science*, 259:1745-1749 (1993); Wang et al, *Proc. Natl. Acad. Sci.*, 90:4156-4160 (1993); Xiang et al., *Virology*, 199: 132-140 (1994)]. Studies to assess this strategy in neutralization of influenza virus have used both envelope and internal viral proteins to induce the production of antibodies, but in particular have focused on the viral hemagglutinin protein (HA) [Fynan et al., *DNA Cell. Biol.*, 12:785-789 (1993A); Fynan et al., *Proc. Natl. Acad. Sci.*, 90:11478-11482 (1993B); Robinson et al., *Vaccine*, 11:957, (1993); Webster et al., *Vaccine*, 12:1495-1498 (1994)].

Vaccination through directly injecting DNA or RNA that encodes a protein to elicit a protective immune response produces both cell-mediated and humoral responses. This is analogous to results obtained with live viruses [Raz et al., *Proc. Natl. Acad. Sci.*, 91:9519-9523 (1994); Ulmer, 1993, supra; Wang, 1993, supra; Xiang, 1994, supra]. Studies with ferrets indicate that DNA vaccines against conserved internal viral proteins of influenza, together with surface glycoproteins, are more effective against antigenic variants of influenza virus than are either inactivated or subvirion vaccines [Donnelly et al., *Nat. Medicine*, 6:583-587 (1995)]. Indeed, reproducible immune responses to DNA encoding nucleoprotein have been reported in mice that last essentially for the lifetime of the animal [Yankauckas et al., *DNA Cell Biol.*, 12: 771-776 (1993)].

A vaccine of the invention can be administered via any parenteral route, including but not limited to intramuscular, intraperitoneal, intravenous, intraarterial (e.g., Ripatic artery) and the like. Preferably, since the desired result of vaccination is to elucidate an immune response to HCV, administration directly, or by targeting or choice of a viral vector, indirectly, to lymphoid tissues, e.g., lymph nodes or spleen. Since immune cells are continually replicating, they are ideal target for retroviral vector-based nucleic acid vaccines, since retroviruses require replicating cells.

Passive immunity can be conferred to an animal subject suspected of suffering an infection with HCV by administering antiserum, neutralizing polyclonal antibodies, or a neutralizing monoclonal antibody against HCV to the patient. Although passive immunity does not confer long-term protection, it can be a valuable tool for the treatment of an acute infection of a subject who has not been vaccinated. Preferably, the antibodies administered for passive immune therapy are autologous antibodies. For example, if the subject is a human, preferably the antibodies are of human origin or have been "humanized," in order to minimize the possibility of an immune response against the antibodies. In addition, genes encoding neutralizing antibodies can be introduced in vectors for expression in vivo, e.g., in hepatocytes.

Antibodies for passive immune therapy. Preferably, HCV variant virions or virus particle proteins prepared as described above are used as an immunogen to generate antibodies that recognize HCV. The variants utilized should have wild-type coat Such antibodies include but are not limited to polyclonal, monoclonal, chimeric, single chain, Fab fragments, and an Fab expression library. Various procedures known in the art may be used for the production of polyclonal antibodies to HCV. For the production of antibody, various host animals can be immunized by injection with the HCV virions or polypeptide, e.g., as describe infra, including but not limited to rabbits, mice, rats, sheep, goats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward HCV as described above, any technique that provides for the production of antibody molecules by continuous cell lines in culture may be used. These include but are not limited to the hybridoma technique originally developed by Kohler and Milstein [*Nature* 256:495-497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals [International Patent Publication No. WO 89/12690, published 28 Dec. 1989]. In fact, according to the invention, techniques developed for the production of "chimeric antibodies" [Morrison et al., *J. Bacteriol.* 159: 870 (1984); Neuberger et al., *Nature* 312:604-608 (1984); Takeda et al., *Nature* 314:452-454 (1985)] by splicing the genes from a mouse antibody molecule specific for HCV together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce HCV-specific single chain antibodies. An additional embodiment of the invention utilizes the techniques described for the construction of Fab expression libraries [Huse et al., *Science* 246:1275-1281 (1989)] to allow rapid and easy identification of monoclonal Fab fragments with the desired specificity.

Antibody fragments containing the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

HCV particles for subunit vaccination. The functional HCV variants of the present invention can be used to produce HCV-like particles for vaccination. Proper glycosylation, folding, and assembly of HCV particles may be important for producing appropriately antigenic and protective subunit vaccines. Several methods can be used for particle production. They include engineering of stable cell lines for inducible or constitutive expression of HCV-like particles (using bacterial, yeast or mammalian cells), or the use of higher level eukaryotic heterologous expression systems such as recombinant baculoviruses, vaccinia viruses [Moss, *Proc. Natl. Acad. Sci. U.S.A.* 93: 11341-11348 (1996)], or alphaviruses [Frolov et al., (1996) supra]. HCV particles for immunization may be purified from either the media or disrupted cells, depending upon their localization. Such purified HCV particles or mixtures of particles representing a spectrum of HCV genotypes, can be injected with our without various adjuvants to enhance immunogenicity.

Infectious non-replicating HCV particles. In another manifestation, particles of HCV variants capable of receptor binding, entry, and translation of genome RNA can be produced. Heterologous expression approaches for production of such particles include, but are not restricted to, *E. coli*, yeast, or mammalian cell lines, appropriate host cells infected or harboring recombinant baculoviruses, recombinant vaccinia viruses, recombinant alphaviruses or RNA replicons, or recombinant adenoviruses, engineered to express appropriate HCV RNAs and proteins. In one example, two recombinant baculoviruses are engineered. One baculovirus expresses the HCV structural proteins (e.g. C-E1-E2-p7) required for assembly of HCV particles. A second recombinant expresses the entire HCV genome RNA, with precise 5' and 3' ends, except that a deletion, such as ΔGDD or GDD→AAG (see example 1), is included to inactivate the HCV NS5B RDRP. Other mutations abolishing productive HCV replication could also be utilized instead or in combination. Cotransfection of appropriate host cells (Sf9, Sf21, etc.) with both recombinants will produce high levels of HCV structural proteins and genome RNA for packaging into HCV-like particles. Such particles can be produced at high levels, purified, and used for vaccination. Once introduced into the vaccinee, such particles will exhibit normal receptor binding and infection of HCV-susceptible cells. Entry will occur and the genome RNA will be translated to produce all of the normal HCV antigens, except that further replication of the genome will be completely blocked given the inactivated NS5B polymerase. Such particles are expected to elicit effective CTL responses against structural and nonstructural HCV protein antigens. This vaccination strategy alone or preferably in conjunction with the subunit strategy described above can be used to elicit high levels of both neutralizing antibodies and CTL responses to help clear the virus. A variety of different HCV genome RNA sequences can be utilized to ensure broadly cross-reactive and protective immune responses. In addition, modification of the HCV particles, either through genetic engineering, or by derivatization in vitro, could be used to target infection to cells most effective at eliciting protective and long lasting immune responses.

Live-attenuated HCV derivatives. The ability to manipulate the HCV genome RNA sequence and thereby produce mutants with altered pathogenicity provides a means of constructing live-attenuated HCV variants appropriate for vaccination. Such vaccine candidates express protective antigens but would be impaired in their ability to cause disease, establish chronic infections, trigger autoimmune responses, and transform cells.

Additionally, viruses propagated in cell culture frequently acquire mutations in their RNA genomes that display attenuated phenotypes in vivo, while still retaining their immunogenicity. Attenuated virus strains would be impaired in their ability to cause disease and establish chronic infections. Production of HCV variants adapted for tissue culture may represent potential candidates for live-attenuated vaccines. An attractive possibility is the production of HCV derivatives containing the deletion in NS5A described in this application as clone I (see Example 1). Such a variant is less likely to revert to wild type in the host.

HCV Variant-Based Gene Expression Vectors

Figure 2:
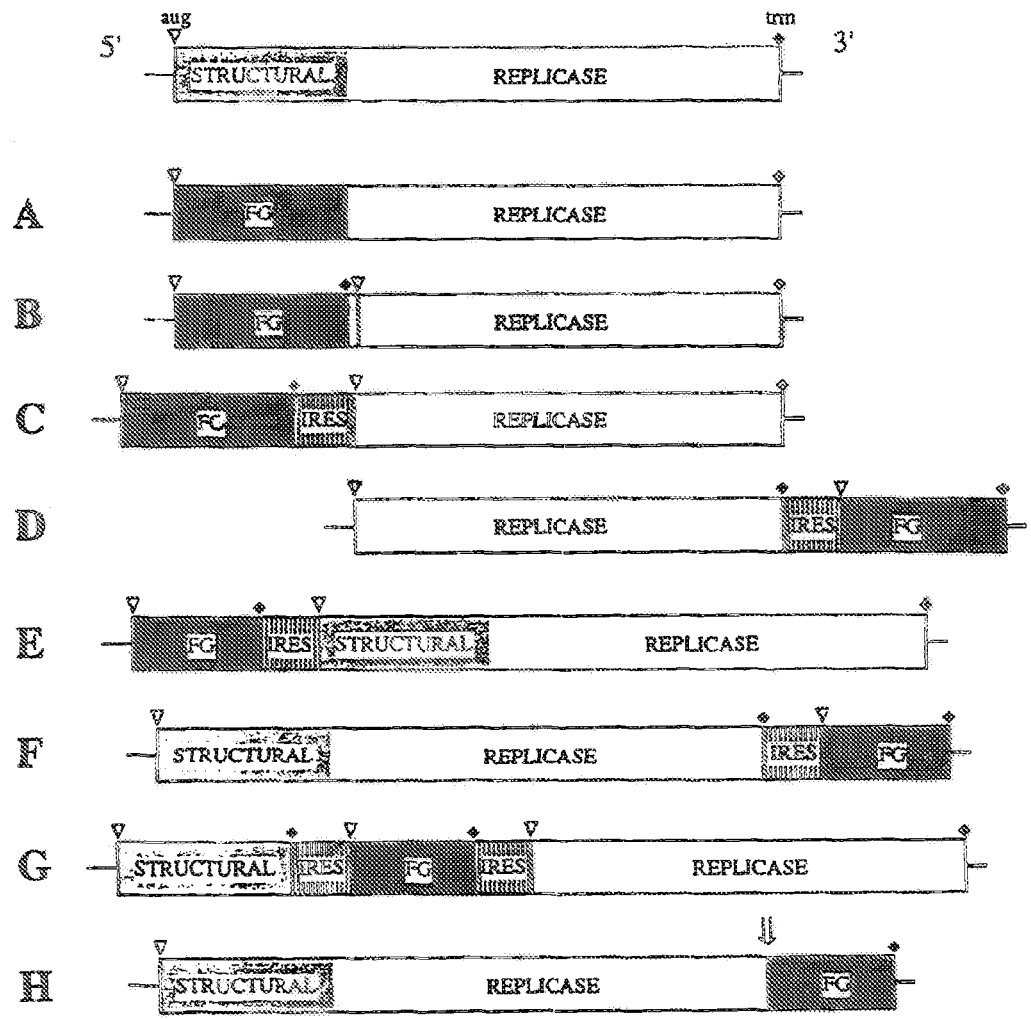
FIG. 2. Strategies for expression of heterologous RNAs and proteins using HCV vectors. At the top is a diagram of the positive-polarity RNA virus HCV, which expresses mature viral proteins by translation of a single long ORF and proteolytic processing. The regions of the polyprotein encoding the structural proteins (STRUCTURAL) and the nonstructural proteins (REPLICASE) are indicated as lightly-shaded and open boxes, respectively. Below are shown a number of proposed replication-competent "replicon" expression constructs. The first four constructs (A-D) lack structural genes and would therefore require a helper system to enable packaging into infectious virions. Constructs E-G would not require helper functions for replication or packaging. Darkly shaded boxes indicate heterologous or foreign gene sequences (FG). Translation initiation (aug) and termination signals (trm) are indicated by open triangles and solid diamonds, respectively. Internal ribosomes entry sites (IRES) are shown as boxes with vertical stripes. Constructs A and H illustrate the expression of a heterologous product as an in-frame fusion with the HCV polyprotein. Such protein fusion junctions can be engineered such that processing is mediated either by host or viral proteinases (indicated by the arrow).

Some of the same properties of HCV leading to chronic liver infection of humans may also be of great utility for designing vectors for gene expression in cell culture systems, genetic vaccination, and gene therapy. The HCV variants described herein can be engineered to produce chimeric RNAs designed for the expression of heterologous gene products (RNAs and proteins). Strategies have been described above and elsewhere [Bredenbeek and Rice, (1992) supra; Frolov et al., (1996) supra] and include, but are not limited to (i) in-frame fusion of the heterologous coding sequences with the HCV polyprotein; (ii) creation of additional cistrons in the HCV genome RNA; and (iii) inclusion of IRES elements to create multicistronic self-replicating HCV vector RNAs capable of expressing one or more heterologous genes (FIG. 2). Functional HCV RNA backbones utilized for such vectors include, but are not limited to, (i) live-attenuated derivatives capable of replication and spread; (ii) RNA replication competent "dead end" derivatives lacking one or more viral components (e.g. the structural proteins) required for viral spread; (iii) mutant derivatives capable of high and low levels of HCV-specific RNA synthesis and accumulation; (iv) mutant derivatives adapted for replication in different human cell types; (v) engineered or selected mutant derivatives capable of prolonged noncytopathic replication in human cells. Vectors competent for RNA replication but not packaging or spread can be introduced either as naked RNA, DNA, or packaged into virus-like particles. Such virus-like particles can be produced as described above and composed of either unmodified or altered HCV virion components designed for targeted transfection of the hepatocytes or other human cell types. Alternatively, HCV RNA vectors can be encapsidated and delivered using heterologous viral packaging machineries or encapsulated into liposomes modified for efficient gene delivery. These packaging strategies, and modifications thereof, can be utilized to efficiently target HCV vector RNAs to specific cell types. Using methods detailed above, similar HCV-derived vector systems, competent for replication and expression in other species, can also be derived.

Various methods, e.g., as set forth supra in connection with transfection of cells and DNA vaccines, can be used to introduce an HCV vector of the invention. Of primary interest is direct injection of functional HCV RNA or virions, e.g., in the liver. Targeted gene delivery is described in International Patent Publication WO 95/28494, published October 1995. Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., Proc. Natl. Acad. Sci. U.S.A. 84:7413-7417 (1987); see Mackey, et al., Proc. Natl. Acad. Sci. U.S.A. 85:8027-8031 (1988); Ulmer et al., Science 259:1745-1748 (1993)]. The use of cationic lipids may promote encapsulation of negatively charged nucleic acids, and also promote fusion with negatively charged cell membranes [Felgner and Ringold, Science 337:387-388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically. Receptor-mediated DNA delivery approaches can also be used [Curiel et al., Hum. Gene Ther. 3:147-154 (1992); Wu and Wu, J. Biol. Chem. 262:4429-4432 (1987)].

Examples of applications for gene therapy include, but are not limited to, (i) expression of enzymes or other molecules to correct inherited or acquired metabolic defects; (ii) expression of molecules to promote wound healing; (iii) expression of immunomodulatory molecules to promote immune-mediated regression or elimination of human cancers; (iv) targeted expression of toxic molecules or enzymes capable of activating cytotoxic drugs in tumors; (v) targeted expression of anti-viral or anti-microbial agents in pathogen-infected cells. Various therapeutic heterologous genes can be inserted in a gene therapy vector of the invention, such as but not limited to adenosine deaminase (ADA) to treat severe combined immunodeficiency (SCID); marker genes or lymphokine genes into tumor infiltrating (TIL) T cells [Kasis et al., Proc. Natl. Acad. Sci. U.S.A. 87:473 (1990); Culver et al., ibid. 88:3155 (1991)]; genes for clonting factors such as Factor VIII and Factor IX for treating hemophilia [Dwarki et al. Proc. Natl. Acad. Sci. USA, 92:1023-1027 (19950); Thompson, Thromb. and Haemostatis, 66:119-122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, omithine transcarbamylase, apolipoproteins, and the like. In general, see U.S. Pat. No. 5,399,346 to Anderson et al.

Examples of applications for genetic vaccination (for protection from pathogens other than HCV) include, but are not limited to, expression of protective antigens from bacterial (e.g., uropathogenic E. coli, Streptoccoci, Staphlococci, Nisseria), parasitic (e.g., Plasmodium, Leishmania, Toxoplama), fungal (e.g., Candida, Histoplasma), and viral (e.g., HIV, HSV, CMV, influenza) human pathogens. Immunogenicity of protective antigens expressed using HCV-derived RNA expression vectors can be enhanced using adjuvants, including co-expression of immunomodulatory molecules, such as cytokines (e.g., IL-2, GM-CSF) to facilitate development of desired Th1 versus Th2 responses. Such adjuvants can be either incorporated and co-expressed by HCV vectors themselves or administered in combination with these vectors using other methods.

Diagnostic Methods for Infectious HCV

Diagnostic cell lines. The invention described herein can also be used to derive cell lines for sensitive diagnosis of infectious HCV in patient samples. In concept, functional HCV components are used to test and create susceptible cell lines (as identified above) in which easily assayed reporter systems are selectively activated upon HCV infection. Examples include, but are not restricted to, (i) defective HCV RNAs lacking replicase components that are incorporated as transgenes and whose replication is upregulated or induced upon HCV infection; and (ii) sensitive heterologous amplifiable reporter systems activated by HCV infection. In the first manifestation, RNA signals required for HCV RNA amplification flank a convenient or a selectable marker (see above).

Expression of such chimeric RNAs is driven by an appropriate nuclear promoter and elements required for proper nuclear processing and transport to the cytoplasm. Upon infection of the engineered cell line with HCV, cytoplasmic replication and amplification of the transgene is induced, triggering higher levels of reporter expression, as an indicator of productive HCV infection.

In the second example, cell lines are designed for more tightly regulated but highly inducible reporter gene amplification and expression upon HCV infection. Although this amplfied system is described in the context of specific components, other equivalent components can be used. In one such system, an engineered alphavirus replicon transgene is created which lacks the alphavirus nsP4 polymerase, an enzyme absolutely required for alphavirus RNA amplification and normally produced by cleavage from the nonstructural polyprotein. Additional features of this defective alphavirus replicon include a subgenomic RNA promoter, driving expression of a luciferase or GFP reporter gene. This promoter element is quiescent in the absence of productive cytoplasmic alphavirus replication. The cell line contains a second transgene for expression of gene fusion consisting of the HCV NS4A protein and the alphavirus nsP4 RDRP. This fused gene is expressed and targeted to the cytoplasmic membrane compartment, but this form of nsP4 would be inactive as a functional component of the alphavirus replication complex because a discrete nsP4 protein, with a precise N terminus is required for nsP4 activity [Lemm et al., *EMBO J.* 13:2925 (1994)]. An optional third transgene expresses a defective alphavirus RNA with cis signals for replication, transcription of subgenomic RNA encoding a ubiquitin-nsP4 fusion, and an alphavirus packaging signal. Upon infection of such a cell line by HCV, the HCV NS3 proteinase is produced, mediating trans cleavage of the NS4A-nsP4 fusion protein, activating the nsP4 polymerase. This active polymerase, which functions in trans and is effective in minute amounts, then forms a functional alphavirus replication complex leading to amplification of the defective alphavirus replicon as well as the defective alphavirus RNA encoding ubiquitin-nsP4. Ubiquitin-nsP4, expressed from its subgenomic RNA, is cleaved efficiently by cellular ubiquitin carboxyterminal hydrolase to product additional nsP4, in case this enzyme is limiting. Once activated, this system would produce extremely high levels of the reporter protein. The time scale of such an HCV infectivity assay is expected to be from hours (for sufficient reporter gene expression).

Antibody diagnostics. In addition to the cell lines described here, HCV variant virus particles (virions) or components thereof, produced by the transfected or infected cell lines, or isolated from an inflected animal, may be used as antigens to detect anti-HCV antibodies in patient blood or blood products. Because the HCV variant virus particles are derived from an authentic HCV genome, particular components such as the coat proteins are likely to have immunogenic properties that more closely resemble or are identical to natural HCV virus than if those components were produced outside of a replicating HCV. Examples of such immunogenic properties include the display of wild-type HCV immunogenic epitopes, and modulation of transcription of genes encoding cellular immune-modulating cytokines. These reagents can be used to establish that a patient is infected with HCV by detecting seroconversion, i.e., generation of a population of HCV-specific antibodies.

Alternatively, antibodies generated to the HCV variant products prepared as described herein can be used to detect the presence of HCV in biological samples from a subject.

Preferred embodiments of the invention are described in the following example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example describes the production and evaluation of replicons comprising a neo selectable marker and a polyprotein coding region encoding subtype 1b nonstructural proteins.

Materials and Methods

Cell lines. The Huh7 cell lines were generously provided by Robert Lanford (Southwest Foundation for Biomedical Research, San Antonio, U.S.A.) and Ralf Bartenschlager (Johannes Gutenberg University Mainz, Mainz, Germany) and maintained in Dulbecco's modified minimal essential media (DMEM; Gibco-BRL) supplemented with 10% fetal calf serum (FCS), and nonessential amino acids.

Assembly of a selectable subtype 1b replicon. An HCV subtype 1b replicon was constructed which is similar to the replicon described in Lohmann et al., *Science* 285:110-113 (1999). For that construction, a step-wise PCR-based assay utilizing KlenTaqLA DNA polymerase (Wayne Barnes, Washington University) was developed. cDNAs spanning 600-750 bases in length were assembled from 10-12 gel-purified oligonucleotides (60-80 nucleotides in length) with unique complementary overlaps of 16 nucleotides. Four or six oligonucleotides representing the 5' portion of the region to be assembled were annealed and extended in a standard PCR. The remaining six oligonucleotides for the synthesis of the 3' half of the intended cDNA were mixed in a parallel PCR reaction. After 12 cycles of PCR, the extended double-stranded DNA products were combined and subjected to an additional 12 cycles. The product of this reaction resolved as a smear on agarose gels which was excised and the DNA isolated from the agarose. One-fifth of the purified double-stranded DNA product was amplified by PCR using an outer primer pair containing unique restriction enzyme sites to facilitate directional cloning into the pGEM3Zf(+) plasmid vector (Promega). PCR products were purified, digested with appropriate restriction enzymes, and ligated into similarly cleaved pGEM3Zf(+). Multiple recombinant clones were sequenced and the correct clones identified. The overlapping cDNA fragments were assembled into the contiguous replicon sequence. In parallel, a replicon carrying the lethal mutation in the NS5B active site (Gly-Asp-Asp [GDD] to Ala-Ala-Gly [AGG]; pol-) was constructed.

RNA transcription and transfection. RNA transcripts were synthesized in a 100 μl reaction mixture containing 40 mM Tris-HCl (pH 7.9), 10 mM NaCl, 12 mM $MgCl_2$, 2 mM spermidine, 3 mM each ATP, CTP, GTP and UTP, 10 mM dithiothreitol, 100 U RNasin (Promega) and 100 U T7 RNA polymerase (Epicentre), and 2 μg Sca I-linearized DNA. The DNA template was rigorously removed by serial digestions with 30 U DNase I (Boehringer). Ten μg of the DNase-digested RNA transcripts were electroporated into $6\times10^6$ Huh7 cells using a model T820 squareporator (BTX), and plated on 150 mm dishes. For selection of replicon-containing cells, medium was changed to complete medium containing geneticin (G418; 1 mg/ml; Gibco-BRL) at 24 hr post-transfection and thereafter the media was changed every 3-4 days.

RNA analysis. Approximately $5 \times 10^5$ cells were preincubated for 1 h in DMEM lacking phosphate supplemented with 5% dialyzed FCS, $\frac{1}{20}^{th}$ the normal concentration of phosphate and actinomycin D (4 µg/ml; Sigma). [$^{32}$P]orthophosphate (200 µCi/ml; ICN) was added and the incubation continued for an additional 12 h. Total cellular RNA was extracted with TRIZOL, precipitated, and resuspended in $H_2O$ (Gibco-BRL). Radiolabeled RNA was analyzed by denaturing agarose gel electrophoresis and visualized by autoradiography.

Protein analysis. For immunoprecipitation, cell monolayers were incubated for either 4, 8 or 12 h in methionine- and cysteine-deficient MEM containing $\frac{1}{40}^{th}$ the normal concentration of methionine, 5% dialyzed FCS and Express $^{35}S^{35}S$ protein labeling mix (100 µCi/ml; NEN). Cells were lysed in 100 mM NaPO4 pH 7.0 containing 1% sodium dodecyl sulfate (SDS) and protease inhibitors, and cellular DNA sheared by repeated passage through a 27.5 gauge needle. Viral proteins were immunoprecipitated essentially as described previously (Grakoui et al, 1993), using patient serum, JHF, recognizing NS3, NS4B and NS5A or rabbit anti-NS5B and Pansorbin cells (Calbiochem). Immunoprecipitates were separated on 10% SDS-PAGE and visualized by autoradiography.

Immunostaining. Cells cultured in 8 well chamber slides (Falcon) were fixed in acetone for 10 min at 4° C. and allowed to air dry. Rehydrated monolayers were incubated at 37° C. with an antibody directed against NS3, followed by incubation with a species-specific fluorescein-conjugated secondary antibody (Pierce), and mounted in 90% glycerol saline containing 50 mM Tris-HCl (pH 8.8).

Reverse transcription (RT)-PCR. RNA was isolated from cells using TRIZOL (Gibco-BRL), precipitated and resuspended in $H_2O$. Levels of HCV RNA were quantitated using competitive RT-PCR assays designed to amplify the 5' and 3' NTR sequences of HCV (Kolykhalov et al, 1996). For RT-PCR designed to amplify long cDNA fragments, about 1000 molecules of HCV RNA was mixed with the HCV-specific primer, and the primer extended at 43.5° C. for 1 h using Superscript II reverse transcriptase (Gibco-BRL). cDNAs were then amplified with KlenTaqLA DNA polymerase using 35 cycles of 95° C. for 30 s, 55-60° C. for 30 s, and 68° C. for 4 min. PCR products were recovered from preparative low melting-point agarose electrophoresis by phenol extraction, and ~40 ng of purified PCR product directly sequenced.

Results

Figure 3:
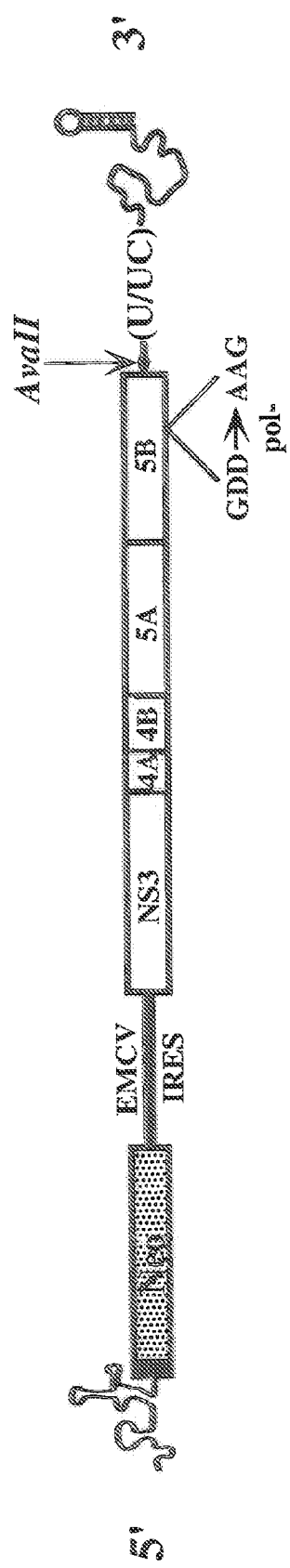
FIG. 3. Structure of HCVrep1bBartMan. Two versions of this infectious replicon were constructed as described in Example 1. The first, HCVrep 1bBartMan/AvaII, has a AvaII restriction site in the variable domain of the 3' NTR that is not present in the 3' NTR of wild-type HCV subtype 1b. The second variant, HCVrep1bBartMan/Δ2U's, has 32, rather than the wild-type 34, U's in the longest stretch of contiguous U's in the polypyrimidine domain of the 3' NTR. The "GDD→AGG" designation shows the inactivating mutation in the non-replicating replicons that were used as polymerase-minus controls in Example 1.

Establishment of G418-resistant colonies. Replicons similar to that described in Lohmann et al, supra, but derived from the H77 infectious clone, failed to confer resistance to G418 in five different hepatoma cell lines. Sequences of subtype 1b were also used to assemble the replicon $I_{377}$/NS3-3' (EMBL accession number AJ242652). Replicon RNAs were composed of the HCV internal ribosome entry site (IRES) driving neomycin phosphotransferase gene (Neo) expression and the IRES from encephalomyocarditis virus (EMCV), directing translation of HCV proteins NS3 to NS5B, followed by the 3' NTR) (FIG. 3). Two derivatives were constructed which either lacked 2 U nucleotides in the poly (U/UC) tract or carried an AvaII restriction enzyme site in the variable region of the 3' NTR, designated HCVrep1bBartMan/Δ2U's and HCVrep1bBartMan/AvaII, respectively. Prior to transfection, translation and correct polyprotein processing was confirmed for each cDNA sequence using the vaccinia-T7 RNA polymerase expression system (data not shown).

DNase-treated replicon RNAs were electroporated into Huh7 cells and after 2-3 weeks in culture G418-resistant colonies were clearly visible. Both replicon derivatives were able to confer G418 resistance, and on average, only 1 in $10^6$ cells became G418 resistant. In contrast, colonies were never observed for Huh7 cells electroporated in parallel with the replicon RNAs containing an inactive NS5B polymerase.

Figure 6:
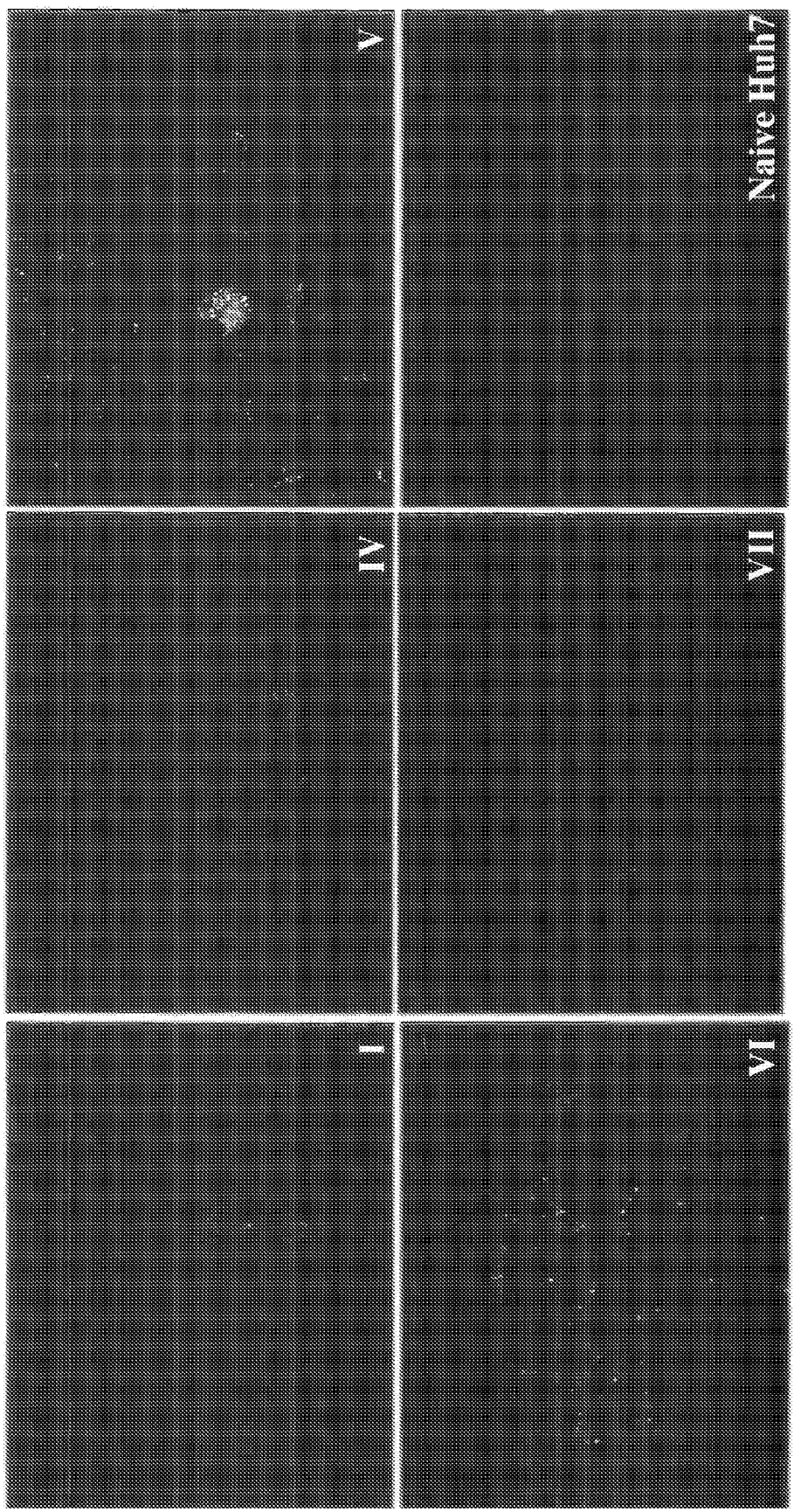
FIG. 6. Detection of NS3 in G418-resistant cell clones. Monolayers of cells transfected with various replicons as indicated were immunostained with an anti-NS3 antibody. Patterns of staining were similar to cells stained from an infected liver.

Verification of autonomous replication. Twenty two independent colonies were isolated, 5 colonies corresponded to Huh7 cells transfected with RNA transcribed from HCVrep1bBartMan/Δ2U's and the remaining 17 colonies were derived from HCVrep1bBartMan/AvaII RNA. A number of assays were performed to verify that G418 resistance was mediated by autonomously replicating HCV. Amplification of sequences within the 5' and 3' NTRs in a quantitative RT-PCR assay revealed copy numbers ranging from 50 to 5000 HCV RNA molecules per cell (FIG. 4). $^{32}$P-labeled, actinomycin D-resistant RNA of the expected size was observed in the four independent G418-resistant cell clones analyzed (FIG. 5A). The HCV proteins, NS3, NS4B, NS5A and NS5B, were immunoprecipitated from radiolabeled cell lysates (FIG. 5B). In addition, immunostaining of cell monolayers revealed a punctate staining pattern for NS3 within the cytoplasm (FIG. 6), similar to HCV protein localization observed in liver sections from HCV-infected patients (Blight and Gowans, 1996). In G418-resistant cell clones the fluorescent signal tended to vary between cells, probably reflecting the different levels of replication per cell.

Figure 7:
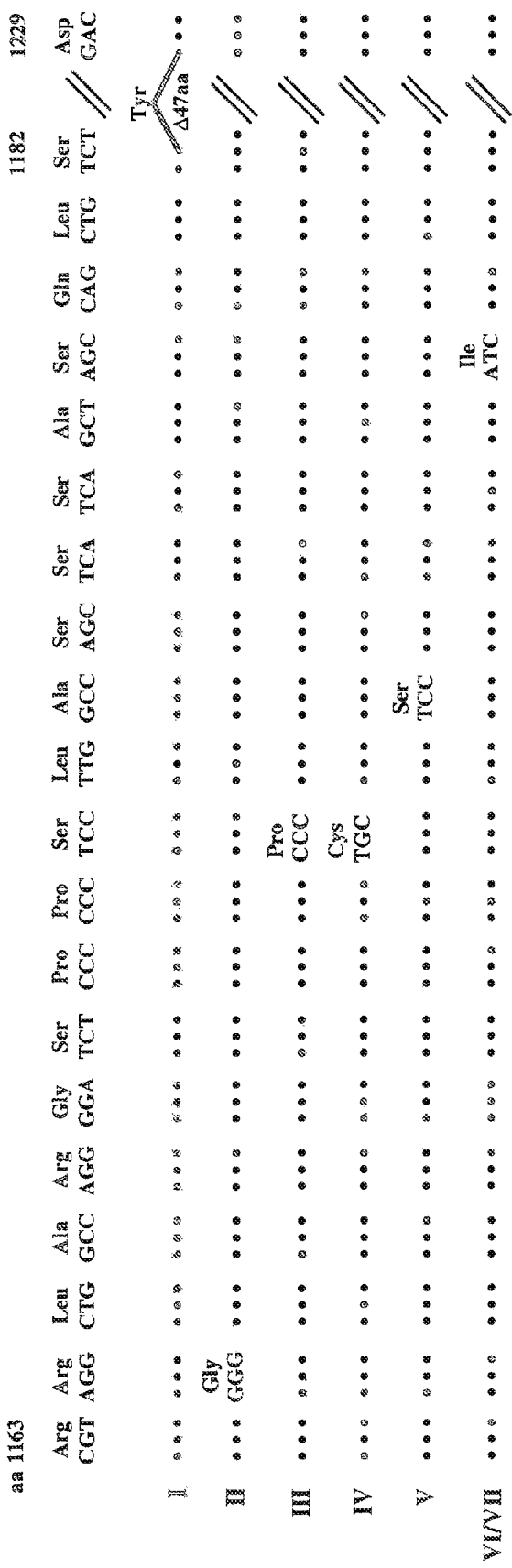
FIG. 7. Nucleotide and amino acid changes in the NS5A coding region of HCV. Nucleotide and amino acid changes in a portion of the NS5A coding region of seven adaptive clones are indicated. In the Figure, the wild type NS5A sequence is from residues 5287 to 5346 (Ser)//5385 (Asp) of SEQ ID NO:6 (nucleotide) and residues 1163 to 1182 (Ser) //1229 (Asp) of SEQ ID NO:4 (amino acid sequence), I (Δ47 Tyr) is from SEQ ID NO: 7 (nucleotide) and SEQ ID NO:14 (NS5A amino acid sequence), II (Arg 1164 Gly) is from SEQ ID NO:9 (nucleotide) and SEQ ID NO:17 (amino acid), III (Ser 1172 Pro) is from SEQ ID NO:12 (nucleotide) and SEQ ID NO: 21 (NS5A amino acid), IV (Ser 1172 Cys) is from SEQ ID NO: 11 (nucleotide) and SEQ ID NO: 20 (NS5A amino acid), V (Ala 1174 Ser) is from SEQ ID NO: 10 (nucleotide) and SEQ ID NO: 19 (NS5A amino acid), and VI/VII (Ser 1179 Ile) is from SEQ ID NO: 8 (nucleotide) and SEQ ID NO: 16 (amino acid).

Identification of mutations in HCV replicons. The low frequency of G418-resistant colonies may be attributed to either a cell factor(s) requirement for replication or adaptive changes within the replicon sequence necessary for the establishment of HCV replication. To address the latter possibility, the entire replicon sequence was amplified from cDNA reverse transcribed from RNA isolated from five independent G418-resistant cell clones. Upon direct sequencing of the purified PCR population, multiple mutations were identified. The striking observation was that each cell clone carried a single nucleotide change within NS5A (SEQ ID NO:4) resulting in a coding change (FIG. 7). In one instance, a deletion of 47 amino acids (I; SEQ ID NO:14; FIG. 7), encompassing the interferon sensitivity determining region (ISDR), was found. Sequence analysis of NS5A from another 8 G418-resistant cell clones revealed similar point mutations, although 2 clones, which have low levels of HCV replication and slow growth rates (e.g., clone E in FIG. 4), were found to contain wild type NS5A (residues 1163 to 1182 and residue 1229 of SEQ ID NO:3). In addition to the identified NS5A mutations, nucleotide substitutions were also noted in NS3 and NS4B; Clone II (SEQ ID NO:9) contains substitutions at nt 3550 (NS3) and nt 4573 (NS4B) (Lys (584) to Glu, and Ser(925) to Gly of SEQ ID NO:3, embodied in SEQ ID NO:17), whereas nt 2060 (NS3) was mutated in Clone VI (FIG. 7, corresponding to Gln (87) to Arg of SEQ ID NO:3, embodied in SEQ ID NO:15).

Figure 8:
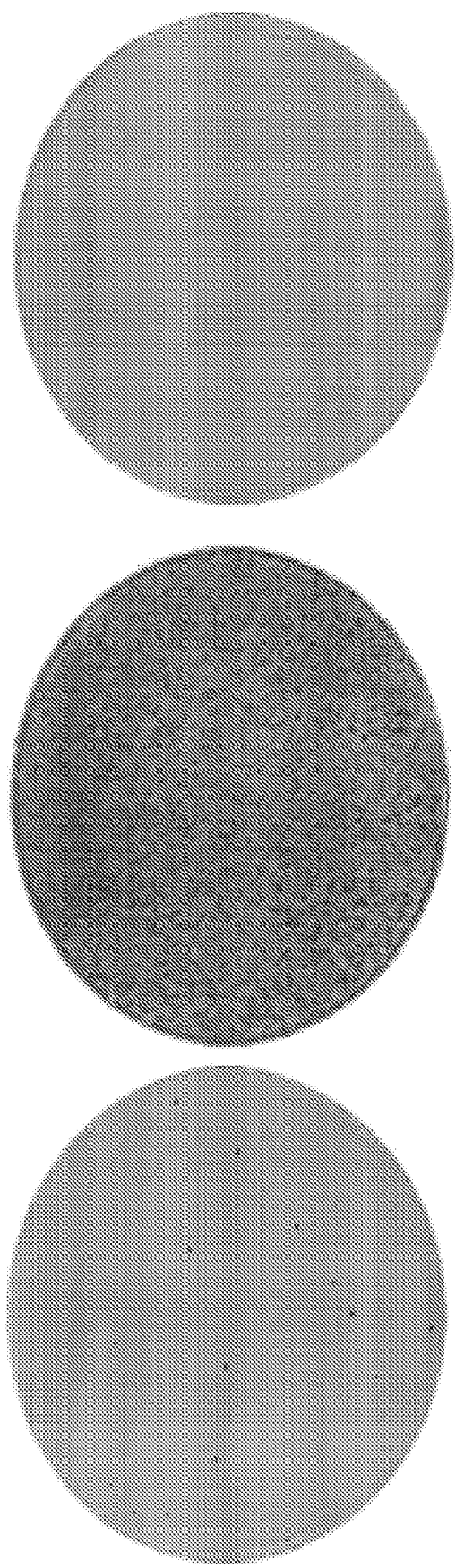
FIG. 8. G418-resistant colonies generated after electroporation of replicon RNAs into Huh7 cells. The ability of an adaptive replicon (Replicon I) to establish colonies after transfection into Huh7 cells (middle) is compared to the original replicon HCVrepBartMan/AvaII (left) and the same adaptive replicon, but with an inactivating mutation in the polymerase gene (right).

Reconstruction of mutant replicons. To determine if the nucleotide changes and the deletion identified in NS5A were adaptive, each mutation, except mutation II, was independently engineered back into the HCVrep1bBartMan/AvaII backbone. RNA transcribed from each reconstructed replicon was electroporated into naive Huh7 cells, and the number of G418-resistant colonies compared to that obtained for the HCVrep1bBartMan/AvaII replicon containing wild type NS5A. The 47 amino acid deletion, as well as the point mutations, were capable of increasing the frequency of G418-resistant colonies to at least 1% of the initial electroporated cell population (FIG. 8), indicating these mutations targeting NS5A are adaptive allowing efficient HCV replication in Huh7 cells. In addition, G418-resistant colonies were observed after transfection of HeLa cells, a human epithelial cell line, with replicon RNA of clone I. Therefore, at least one of the mutations that was adaptive in Huh7 cells also allows the establishment of HCV replication in a non-hepatic cell line.

EXAMPLE 2

This example describes the production of cell lines permissive for HCV replication; a replicon comprising the NS2 coding region; and full-length HCV cDNA clones comprising the Ser to Ile substitution at position 1179 of SEQ ID NO:3.

Generation of cell lines. As shown in the previous example, G418-resistant cell clones harboring persistently replicating HCV RNAs were isolated. Two of these G418-resistant cell clones were treated extensively with the antiviral, interferon-α, to obtain 2 cell lines void of HCV RNA. These are refered to as interferon-treated cell lines I and II.

HCVrep1bBartMan/AvaII, HCV adaptive replicon I or HCV adaptive replicon VII were transfected into the interferon-treated cell lines, I and II. This resulted in a greater G418 transduction efficiency than that observed for the parental Huh-7 cells (see Table 1). Early post-transfection HCV RNA amplification was greatest for the IFN-treated cell line. These results indicate that the cell lines, interferon-treated cell lines I and II, are more permissive for HCV replication than is the parental Huh-7 cell line.

Such cell lines are not only valuable for genetic study of HCV, but also for examining the cellular environments more permissive for HCV replication. For example, microarray technology will allow us to look globally at differences in gene expression profiles between the different cell lines.

Figure 10:
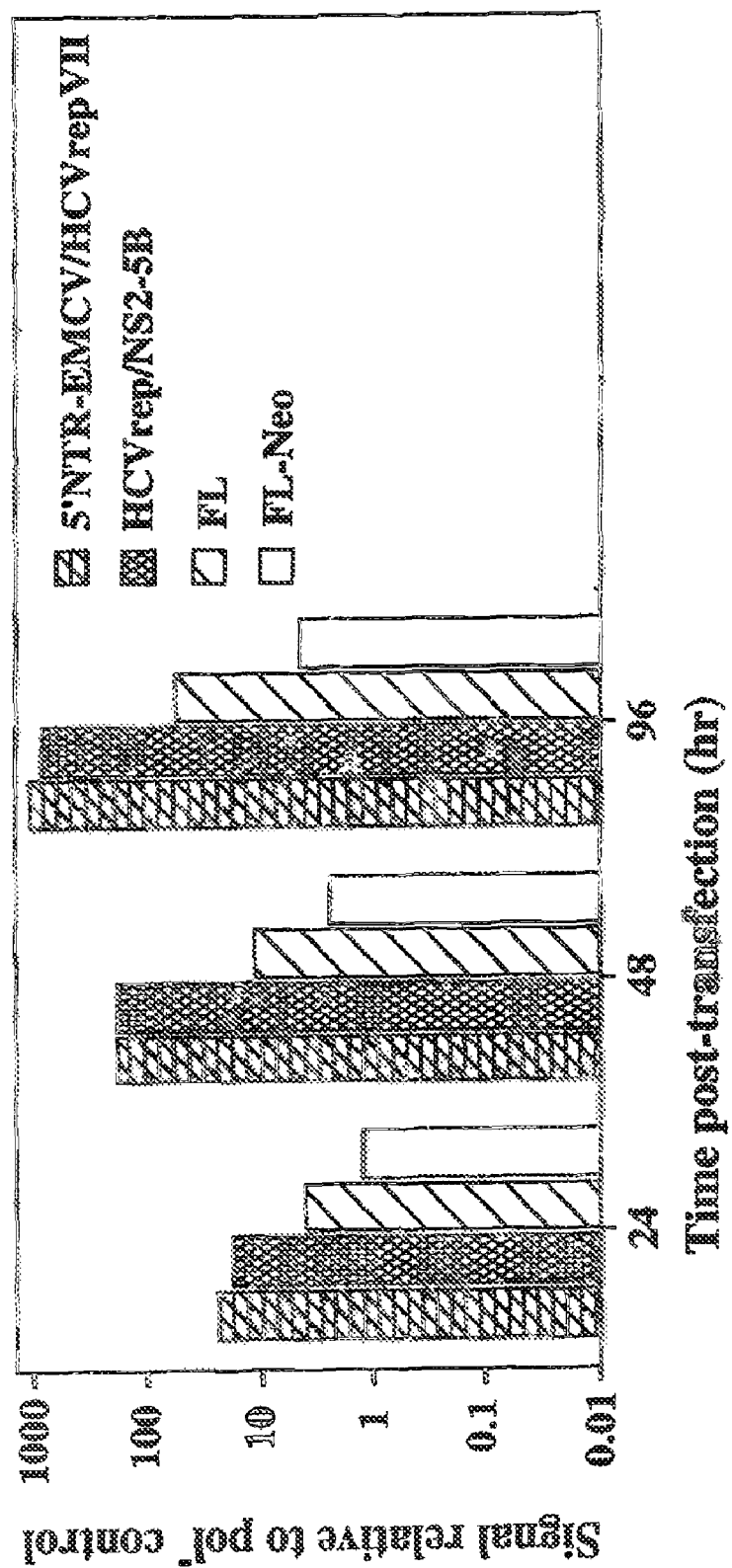
FIG. 10. RNA replication of replicons and full-length HCV RNAs. The HCV replicons and full-length HCV RNAs shown in FIG. 9 are replication competent.

Construction of replicons. A replicon was constructed wherein the 5'NTR of HCV was fused to the IRES of EMCV upstream of NS3, thus creating a replicon lacking the neomycin phosphotransferase gene. This replicon, 5'NTR-EMCV/HCVrepVII (SEQ ID NO:25), replicates to high levels in Huh7 cells, as shown in FIG. 10. Another replicon, HCVrep/NS2-5B (SEQ ID NO:22) was made wherein the non-structural protein, NS2, is upstream of NS3. As shown in FIG. 10, this replicon is also replication-competent in Huh7 cells. This latter replicon can be used advantageously, for example, in testing compounds for inhibiting HCV replication. The addition of the NS2 coding region provides an additional target for such antiviral compounds, as well as providing an additional protein for genetic study.

Figure 9:
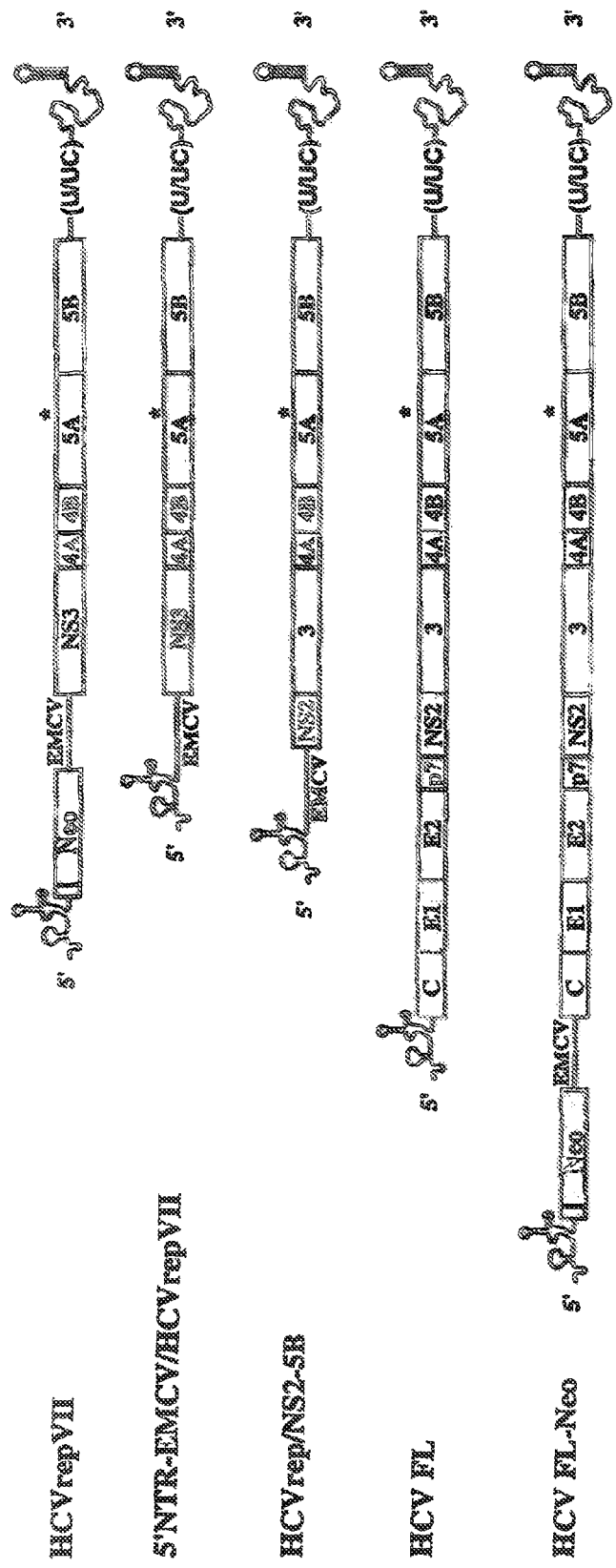
FIG. 9. Structures of HCV replicons and full-length HCV RNAs. The adaptive replicon 5'NTR-EMCV has the 5'NTR fused directly to the EMCV IRES upstream of NS3. Another adaptive replicon, HCVrep/NS2-5B has the non-structural protein, NS2, upstream of NS3. A full-length HCV cDNA clone, HCV FL, was assembled. Also, a bicistronic derivative, HCV FL-neo, was assembled where the 5'NTR is fused to the neomycin phosphotransferase gene and the EMCV IRES is upstream of the HCV open reading frame. In both full-length clones, the open reading frame comprises the structural and non-structural regions, from capsid to NS5B. In addition, all of the replicons and full-length HCV RNAs comprise the mutation coding for Ser to Ile substitution at position 1179 of SEQ ID NO:3, in NS5A.

Full-length HCV RNAs. Two full-length HCV cDNA clones were assembled. The first, HCV FL (SEQ ID NO:24), contains the mutation that encodes a Ser to Ile substitution in NS5A, as shown at position 1179 of SEQ ID NO:3 (see FIG. 9). The second, HCV FL-Neo (SEQ ID NO:23), also encodes the Ser to Ile mutation, and in addition, comprises the neomycin phosphotransferase gene immediately 3' of the 5' NTR and the EMCV IRES immediately 5' to the HCV open reading frame (see FIG. 9). Both of these full-length clones replicate in the interferon-treated cell line I, as shown in FIG. 10. This result indicates that HCV replication is not dependent on the EMCV IRES driving the non-structural proteins of HCV, because the non-structural proteins of the HCV FL clone are driven by the HCV IRES in the full-length clone HCV FL.

In addition, a G418 resistant cell line comprising the HCV FL-Neo clone has been generated from the interferon-treated cell line I described above. This cell line supports high levels of persistently replicating HCV FL-Neo RNA.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings and appendix shall be interpreted as illustrative and not in a limiting sense.

TABLE 1

Relative G418 transduction efficiencies of HCV replicons after transfection into interferon-treated cell clones

| Cell line | Transfected replicon | | |
|---|---|---|---|
| | BartMan | I | VII |
| parental Huh-7 | 0.0005% | 0.15% | 9% |
| IFN-treated I | 0.005% | 5% | 30% |
| IFN-treated II | 0.001% | 1.3% | 11% |

What is claimed is:

1. A method for producing a cell line that is more permissive for HCV replication, said method comprising the steps of:

a. providing a permissive cell line that comprises a replicating HCV RNA;

b. treating said cell line of (a) with an antiviral agent;

c. selecting a cell line of (b) that is void of HCV RNA;

d. growing the selected cell line of (c) to generate a second cell line, and e. comparing the transduction efficiency of said second cell line with the transduction efficiency of a parental cell line used to provide the permissive cell line of (a) with a same HCV RNA, thereby identifying a cell line that is more permissive for HCV replication than the parental cell line used to provide the permissive cell line of (a).

2. The method according to claim 1, wherein said replicating HCV comprises an HCV replicon or a full-length HCV RNA.

3. The method according to claim 1, wherein said antiviral agent is interferon.

4. The method of claim 3, wherein said interferon is interferon-α.

5. The method according to claim 1, wherein said cell line is a human cell line.

6. The method according to claim 5, wherein said human cell line is a hepatocyte cell line.

7. The method of claim 1, wherein the cell line of (a) that comprises a replicating HCV RNA is provided by transfecting a cell line with a HCV replicon or a full-length HCV RNA.

8. The method of claim 1, further comprising a step (f) of transfecting the cell line that is more permissive for HCV RNA replication with an HCV replicon or a full-length HCV RNA.

9. The method of claim 8, wherein said HCV RNA replicon or said full-length HCV RNA that is transfected in step (f) contains an adaptive mutation.

10. The method of claim 9, wherein said adaptive mutation in said HCV RNA replicon or said full-length HCV RNA encodes a Ser 1179 to Ile substitution in NS5A as shown in FIG. 7.

* * * * *

SEQUENCE LISTING

<160> NUMBER OF SEQ ID NOS: 25

<210> SEQ ID NO 1
<211> LENGTH: 21
<212> TYPE: DNA
<213> ORGANISM: Hepatitis C virus

<400> SEQUENCE: 1
ggcgacactc caccatagat c                                      21

<210> SEQ ID NO 2
<211> LENGTH: 99
<212> TYPE: DNA
<213> ORGANISM: Hepatitis C virus

<400> SEQUENCE: 2

-continued

```
tggtggctcc atcttagccc tagtcacggc tagctgtgaa aggtccgtga gccgcatgac      60
tgcagagagt gctgatactg gcctctctgc tgatcatgt                              99
```

<210> SEQ ID NO 3
<211> LENGTH: 1985
<212> TYPE: PRT
<213> ORGANISM: Hepatitis C virus

<400> SEQUENCE: 3

```
Met Ala Pro Ile Thr Ala Tyr Ser Gln Gln Thr Arg Gly Leu Leu Gly
  1               5                  10                  15

Cys Ile Ile Thr Ser Leu Thr Gly Arg Asp Arg Asn Gln Val Glu Gly
             20                  25                  30

Glu Val Gln Val Val Ser Thr Ala Thr Gln Ser Phe Leu Ala Thr Cys
         35                  40                  45

Val Asn Gly Val Cys Trp Thr Val Tyr His Gly Ala Gly Ser Lys Thr
     50                  55                  60

Leu Ala Gly Pro Lys Gly Pro Ile Thr Gln Met Tyr Thr Asn Val Asp
 65                  70                  75                  80

Gln Asp Leu Val Gly Trp Gln Ala Pro Pro Gly Ala Arg Ser Leu Thr
                 85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Ser Thr Gly Glu Ile Pro Phe Tyr Gly
            340                 345                 350
```

-continued

```
Lys Ala Ile Pro Ile Glu Thr Ile Lys Gly Gly Arg His Leu Ile Phe
            355                 360                 365
Cys His Ser Lys Lys Cys Asp Glu Leu Ala Ala Lys Leu Ser Gly
        370                 375                 380
Leu Gly Leu Asn Ala Val Ala Tyr Tyr Arg Gly Leu Asp Val Ser Val
385                 390                 395                 400
Ile Pro Thr Ser Gly Asp Val Ile Val Ala Thr Asp Ala Leu Met
                405                 410                 415
Thr Gly Phe Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
            435                 440                 445
Thr Thr Thr Val Pro Gln Asp Ala Val Ser Arg Ser Gln Arg Arg Gly
        450                 455                 460
Arg Thr Gly Arg Gly Arg Met Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Ser Val
                500                 505                 510
Arg Leu Arg Ala Tyr Leu Asn Thr Pro Gly Leu Pro Val Cys Gln Asp
            515                 520                 525
His Leu Glu Phe Trp Glu Ser Val Phe Thr Gly Leu Thr His Ile Asp
        530                 535                 540
Ala His Phe Leu Ser Gln Thr Lys Gln Ala Gly Asp Asn Phe Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
                580                 585                 590
Leu His Gly Pro Thr Pro Leu Leu Tyr Arg Leu Gly Ala Val Gln Asn
            595                 600                 605
Glu Val Thr Thr Thr His Pro Ile Thr Lys Tyr Ile Met Ala Cys Met
        610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Lys Pro Ala Ile Ile Pro Asp
                660                 665                 670
Arg Glu Val Leu Tyr Arg Glu Phe Asp Glu Met Glu Glu Cys Ala Ser
            675                 680                 685
His Leu Pro Tyr Ile Glu Gln Gly Met Gln Leu Ala Glu Gln Phe Lys
        690                 695                 700
Gln Lys Ala Ile Gly Leu Leu Gln Thr Ala Thr Lys Gln Ala Glu Ala
705                 710                 715                 720
Ala Ala Pro Val Val Glu Ser Lys Trp Arg Thr Leu Glu Ala Phe Trp
                725                 730                 735
Ala Lys His Met Trp Asn Phe Ile Ser Gly Ile Gln Tyr Leu Ala Gly
                740                 745                 750
Leu Ser Thr Leu Pro Gly Asn Pro Ala Ile Ala Ser Leu Met Ala Phe
            755                 760                 765
Thr Ala Ser Ile Thr Ser Pro Leu Thr Thr Gln His Thr Leu Leu Phe
```

-continued

```
            770                 775                 780
Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
                820                 825                 830

Gly Val Ala Gly Ala Leu Val Ala Phe Lys Val Met Ser Gly Glu Met
                835                 840                 845

Pro Ser Thr Glu Asp Leu Val Asn Leu Leu Pro Ala Ile Leu Ser Pro
850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
                900                 905                 910

Ser Asp Ala Ala Ala Arg Val Thr Gln Ile Leu Ser Ser Leu Thr Ile
                915                 920                 925

Thr Gln Leu Leu Lys Arg Leu His Gln Trp Ile Asn Glu Asp Cys Ser
                930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
                965                 970                 975

Arg Leu Pro Gly Val Pro Phe Phe Ser Cys Gln Arg Gly Tyr Lys Gly
                980                 985                 990

Val Trp Arg Gly Asp Gly Ile Met Gln Thr Thr Cys Pro Cys Gly Ala
                995                 1000                1005

Gln Ile Thr Gly His Val Lys Asn Gly Ser Met Arg Ile Val Gly Pro
    1010                1015                1020

Arg Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
                1045                1050                1055

Leu Trp Arg Val Ala Ala Glu Glu Tyr Val Glu Val Thr Arg Val Gly
                1060                1065                1070

Asp Phe His Tyr Val Thr Gly Met Thr Thr Asp Asn Val Lys Cys Pro
    1075                1080                1085

Cys Gln Val Pro Ala Pro Glu Phe Phe Thr Glu Val Asp Gly Val Arg
    1090                1095                1100

Leu His Arg Tyr Ala Pro Ala Cys Lys Pro Leu Leu Arg Glu Glu Val
1105                1110                1115                1120

Thr Phe Leu Val Gly Leu Asn Gln Tyr Leu Val Gly Ser Gln Leu Pro
                1125                1130                1135

Cys Glu Pro Glu Pro Asp Val Ala Val Leu Thr Ser Met Leu Thr Asp
                1140                1145                1150

Pro Ser His Ile Thr Ala Glu Thr Ala Lys Arg Arg Leu Ala Arg Gly
    1155                1160                1165

Ser Pro Pro Ser Leu Ala Ser Ser Ser Ala Ser Gln Leu Ser Ala Pro
    1170                1175                1180

Ser Leu Lys Ala Thr Cys Thr Thr Arg His Asp Ser Pro Asp Ala Asp
1185                1190                1195                1200
```

```
Leu Ile Glu Ala Asn Leu Leu Trp Arg Gln Glu Met Gly Gly Asn Ile
                1205                1210                1215

Thr Arg Val Glu Ser Glu Asn Lys Val Val Ile Leu Asp Ser Phe Glu
                1220                1225                1230

Pro Leu Gln Ala Glu Glu Asp Glu Arg Glu Val Ser Val Pro Ala Glu
                1235                1240                1245

Ile Leu Arg Arg Ser Arg Lys Phe Pro Arg Ala Met Pro Ile Trp Ala
    1250                1255                1260

Arg Pro Asp Tyr Asn Pro Pro Leu Leu Glu Ser Trp Lys Asp Pro Asp
1265                1270                1275                1280

Tyr Val Pro Pro Val Val His Gly Cys Pro Leu Pro Pro Ala Lys Ala
                1285                1290                1295

Pro Pro Ile Pro Pro Arg Arg Lys Arg Thr Val Val Leu Ser Glu
                1300                1305                1310

Ser Thr Val Ser Ser Ala Leu Ala Glu Leu Ala Thr Lys Thr Phe Gly
            1315                1320                1325

Ser Ser Glu Ser Ser Ala Val Asp Ser Gly Thr Ala Thr Ala Ser Pro
    1330                1335                1340

Asp Gln Pro Ser Asp Asp Gly Asp Ala Gly Ser Asp Val Glu Ser Tyr
1345                1350                1355                1360

Ser Ser Met Pro Pro Leu Glu Gly Glu Pro Gly Asp Pro Asp Leu Ser
            1365                1370                1375

Asp Gly Ser Trp Ser Thr Val Ser Glu Glu Ala Ser Glu Asp Val Val
        1380                1385                1390

Cys Cys Ser Met Ser Tyr Thr Trp Thr Gly Ala Leu Ile Thr Pro Cys
    1395                1400                1405

Ala Ala Glu Glu Thr Lys Leu Pro Ile Asn Ala Leu Ser Asn Ser Leu
    1410                1415                1420

Leu Arg His His Asn Leu Val Tyr Ala Thr Thr Ser Arg Ser Ala Ser
1425                1430                1435                1440

Leu Arg Gln Lys Lys Val Thr Phe Asp Arg Leu Gln Val Leu Asp Asp
            1445                1450                1455

His Tyr Arg Asp Val Leu Lys Glu Met Lys Ala Lys Ala Ser Thr Val
                1460                1465                1470

Lys Ala Lys Leu Leu Ser Val Glu Glu Ala Cys Lys Leu Thr Pro Pro
    1475                1480                1485

His Ser Ala Arg Ser Lys Phe Gly Tyr Gly Ala Lys Asp Val Arg Asn
    1490                1495                1500

Leu Ser Ser Lys Ala Val Asn His Ile Arg Ser Val Trp Lys Asp Leu
1505                1510                1515                1520

Leu Glu Asp Thr Glu Thr Pro Ile Asp Thr Thr Ile Met Ala Lys Asn
                1525                1530                1535

Glu Val Phe Cys Val Gln Pro Glu Lys Gly Gly Arg Lys Pro Ala Arg
                1540                1545                1550

Leu Ile Val Phe Pro Asp Leu Gly Val Arg Val Cys Glu Lys Met Ala
            1555                1560                1565

Leu Tyr Asp Val Val Ser Thr Leu Pro Gln Ala Val Met Gly Ser Ser
    1570                1575                1580

Tyr Gly Phe Gln Tyr Ser Pro Gly Gln Arg Val Glu Phe Leu Val Asn
1585                1590                1595                1600

Ala Trp Lys Ala Lys Lys Cys Pro Met Gly Phe Ala Tyr Asp Thr Arg
                1605                1610                1615
```

-continued

Cys Phe Asp Ser Thr Val Thr Glu Asn Asp Ile Arg Val Glu Glu Ser
         1620                1625                1630

Ile Tyr Gln Cys Cys Asp Leu Ala Pro Glu Ala Arg Gln Ala Ile Arg
         1635                1640                1645

Ser Leu Thr Glu Arg Leu Tyr Ile Gly Gly Pro Leu Thr Asn Ser Lys
         1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ala Ala Ala
              1685                1690                1695

Cys Arg Ala Ala Lys Leu Gln Asp Cys Thr Met Leu Val Cys Gly Asp
              1700                1705                1710

Asp Leu Val Val Ile Cys Glu Ser Ala Gly Thr Gln Glu Asp Glu Ala
         1715                1720                1725

Ser Leu Arg Ala Phe Thr Glu Ala Met Thr Arg Tyr Ser Ala Pro Pro
         1730                1735                1740

Gly Asp Pro Pro Lys Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
              1765                1770                1775

Tyr Leu Thr Arg Asp Pro Thr Thr Pro Leu Ala Arg Ala Ala Trp Glu
              1780                1785                1790

Thr Ala Arg His Thr Pro Val Asn Ser Trp Leu Gly Asn Ile Ile Met
         1795                1800                1805

Tyr Ala Pro Thr Leu Trp Ala Arg Met Ile Leu Met Thr His Phe Phe
         1810                1815                1820

Ser Ile Leu Leu Ala Gln Glu Gln Leu Glu Lys Ala Leu Asp Cys Gln
1825                1830                1835                1840

Ile Tyr Gly Ala Cys Tyr Ser Ile Glu Pro Leu Asp Leu Pro Gln Ile
              1845                1850                1855

Ile Gln Arg Leu His Gly Leu Ser Ala Phe Ser Leu His Ser Tyr Ser
              1860                1865                1870

Pro Gly Glu Ile Asn Arg Val Ala Ser Cys Leu Arg Lys Leu Gly Val
         1875                1880                1885

Pro Pro Leu Arg Val Trp Arg His Arg Ala Arg Ser Val Arg Ala Arg
         1890                1895                1900

Leu Leu Ser Gln Gly Gly Arg Ala Ala Thr Cys Gly Lys Tyr Leu Phe
1905                1910                1915                1920

Asn Trp Ala Val Arg Thr Lys Leu Lys Leu Thr Pro Ile Pro Ala Ala
              1925                1930                1935

Ser Gln Leu Asp Leu Ser Ser Trp Phe Val Ala Gly Tyr Ser Gly Gly
              1940                1945                1950

Asp Ile Tyr His Ser Leu Ser Arg Ala Arg Pro Arg Trp Phe Met Trp
         1955                1960                1965

Cys Leu Leu Leu Leu Ser Val Gly Val Gly Ile Tyr Leu Leu Pro Asn
    1970                1975                1980

Arg
1985

<210> SEQ ID NO 4
<211> LENGTH: 447
<212> TYPE: PRT
<213> ORGANISM: Hepatitis C virus

<400> SEQUENCE: 4

```
Ser Gly Ser Trp Leu Arg Asp Val Trp Asp Trp Ile Cys Thr Val Leu
 1               5                  10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
            35                  40                  45

Gly Asp Gly Ile Met Gln Thr Thr Cys Pro Cys Gly Ala Gln Ile Thr
        50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
            115                 120                 125

Tyr Val Thr Gly Met Thr Thr Asp Asn Val Lys Cys Pro Cys Gln Val
        130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
            195                 200                 205

Ile Thr Ala Glu Thr Ala Lys Arg Arg Leu Ala Arg Gly Ser Pro Pro
        210                 215                 220

Ser Leu Ala Ser Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
            275                 280                 285

Ala Glu Glu Asp Glu Arg Glu Val Ser Val Pro Ala Glu Ile Leu Arg
        290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350

Pro Pro Pro Arg Arg Lys Arg Thr Val Val Leu Ser Glu Ser Thr Val
        355                 360                 365

Ser Ser Ala Leu Ala Glu Leu Ala Thr Lys Thr Phe Gly Ser Ser Glu
370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415
```

```
Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
            435                 440                 445

<210> SEQ ID NO 5
<211> LENGTH: 7987
<212> TYPE: DNA
<213> ORGANISM: Hepatitis C virus

<400> SEQUENCE: 5
```

| | | | | | |
|---|---|---|---|---|---|
| gccagccccc | gattgggggc | gacactccac | catagatcac | tccctgtga | ggaactactg | 60 |
| tcttcacgca | gaaagcgtct | agccatggcg | ttagtatgag | tgtcgtgcag | cctccaggac | 120 |
| ccccctccc | gggagagcca | tagtggtctg | cggaaccggt | gagtacaccg | gaattgccag | 180 |
| gacgaccggg | tccttcttg | gatcaacccg | ctcaatgcct | ggagatttgg | gcgtgccccc | 240 |
| gcgagactgc | tagccgagta | gtgttgggtc | gcgaaaggcc | ttgtggtact | gcctgatagg | 300 |
| gtgcttgcga | gtgccccggg | aggtctcgta | gaccgtgcac | catgagcacg | aatcctaaac | 360 |
| ctcaaagaaa | aaccaaaggg | cgcgccatga | ttgaacaaga | tggattgcac | gcaggttctc | 420 |
| cggccgcttg | ggtggagagg | ctattcggct | atgactgggc | acaacagaca | atcggctgct | 480 |
| ctgatgccgc | cgtgttccgg | ctgtcagcgc | aggggcgccc | ggttcttttt | gtcaagaccg | 540 |
| acctgtccgg | tgccctgaat | gaactgcagg | acgaggcagc | gcggctatcg | tggctggcca | 600 |
| cgacgggcgt | tccttgcgca | gctgtgctcg | acgttgtcac | tgaagcggga | agggactggc | 660 |
| tgctattggg | cgaagtgccg | gggcaggatc | tcctgtcatc | tcaccttgct | cctgccgaga | 720 |
| aagtatccat | catggctgat | gcaatgcggc | ggctgcatac | gcttgatccg | gctacctgcc | 780 |
| cattcgacca | ccaagcgaaa | catcgcatcg | agcgagcacg | tactcggatg | aagccggtc | 840 |
| ttgtcgatca | ggatgatctg | gacgaagagc | atcaggggct | cgcgccagcc | gaactgttcg | 900 |
| ccaggctcaa | ggcgcgcatg | cccgacggcg | aggatctcgt | cgtgacccat | ggcgatgcct | 960 |
| gcttgccgaa | tatcatggtg | gaaaatggcc | gcttttctgg | attcatcgac | tgtggccggc | 1020 |
| tgggtgtggc | ggaccgctat | caggacatag | cgttggctac | ccgtgatatt | gctgaagagc | 1080 |
| ttggcggcga | atgggctgac | cgcttcctcg | tgctttacgg | tatcgccgct | cccgattcgc | 1140 |
| agcgcatcgc | cttctatcgc | cttcttgacg | agttcttctg | agtttaaaca | gaccacaacg | 1200 |
| gtttccctct | agcgggatca | attccgcccc | tctccctccc | ccccccctaa | cgttactggc | 1260 |
| cgaagccgct | tggaataagg | ccggtgtgcg | tttgtctata | tgttattttc | caccatattg | 1320 |
| ccgtcttttg | gcaatgtgag | ggcccggaaa | cctggccctg | tcttcttgac | gagcattcct | 1380 |
| aggggtcttt | cccctctcgc | caaggaatg | caaggtctgt | tgaatgtcgt | gaaggaagca | 1440 |
| gttcctctgg | aagcttcttg | aagacaaaca | acgtctgtag | cgaccctttg | caggcagcgg | 1500 |
| aaccccccac | ctggcgacag | tgcctctgc | ggccaaaagc | cacgtgtata | agatacacct | 1560 |
| gcaaaggcgg | cacaacccca | gtgccacgtt | gtgagttgga | tagttgtgga | aagagtcaaa | 1620 |
| tggctctcct | caagcgtatt | caacaagggg | ctgaaggatg | cccagaaggt | accccattgt | 1680 |
| atgggatctg | atctggggcc | tcggtgcaca | tgctttacat | gtgtttagtc | gaggttaaaa | 1740 |
| aacgtctagg | cccccgaac | cacggggacg | tggttttcct | ttgaaaaaca | cgataatacc | 1800 |
| atgcgcccta | ttacggccta | ctcccaacag | acgcgaggcc | tacttggctg | catcatcact | 1860 |
| agcctcacag | gccgggacag | gaaccaggtc | gagggggagg | tccaagtggt | ctccaccgca | 1920 |
| acacaatctt | tcctggcgac | ctgcgtcaat | ggcgtgtgtt | ggactgtcta | tcatggtgcc | 1980 |

```
ggctcaaaga cccttgccgg cccaaagggc ccaatcaccc aaatgtacac caatgtggac    2040
caggacctcg tcggctggca agcgccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340 cggtccccg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc    2640 tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggggcagg atgggcattt acaggtttgt gactccagga    3240
gaacggccct cggcatgtt cgattcctcg gttctgtgcg agtgctatga cgcgggctgt    3300
gcttggtacg agctcacgcc cgccgagacc tcagttaggt tgcgggctta cctaaacaca    3360 ccaggggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca cgtggtcat tgtgggcagg    3780 atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960 gctgctccg tggtggaatc caagtggcgg accctcgaag ccttctgggc gaagcatatg    4020
tggaatttca tcagcgggat acaatattta gcaggcttgt ccactctgcc tggcaaccc    4080 gcgatagcat cactgatggc attcacagcc tctatcacca gccgctcac cacccaacat    4140 accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
```

-continued

```
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggaggggc tgtgcagtgg atgaaccggc tgatagcgtt cgcttcgcgg      4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tgctaagag atgtttggga ttggatatgc     4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtggggatt tccactacgt gacgggcatg     5040
accactgaca acgtaaagtg cccgtgtcag gttccggccc ccgaattctt cacagaagtg    5100
gatgggtgc ggttgcacag gtacgctcca gcgtgcaaac ccctcctacg ggaggaggtc     5160
acattcctgg tcgggctcaa tcaatacctg gttgggtcac agctcccatg cgagcccgaa    5220
ccggacgtag cagtgctcac ttccatgctc accgaccct cccacattac ggcggagacg     5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag     5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagaccttc cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc ccccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgccat caatgcactg     6060
agcaactctt tgctccgtca ccacaacttg gtctatgcta caacatctcg cagcgcaagc    6120
ctgcggcaga agaaggtcac cttttgacaga ctgcaggtcc tggacgacca ctaccgggac   6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg     6360
ctggaagaca ctgagacacc aattgacacc accatcatga caaaaatga ggttttctgc    6420
gtccaaccag agaagggggg ccgcaagcca gctcgcctta tcgtattccc agatttgggg   6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
```

-continued

```
cccgaagcca gacaggccat aaggtcgctc acagagcggc tttacatcgg gggccccctg    6780
actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctggggaccc gcccaaacca gaatacgact tggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccagggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt    7680
gcccgacccc gctggttcat gtggtgccta ctcctacttt ctgtagggt aggcatctat     7740 ctactcccca accgatgaac ggggagctaa acactccagg ccaataggcc atcctgtttt    7800 tttcccttt tttttttctt ttttttttt ttttttttt tttttttttt ctccttttt        7860 tttcctcttt ttttccttt ctttccttg gtggctccat cttagcccta gtcacggcta     7920
gctgtgaaag gtccgtgagc cgcttgactg cagagagtgc tgatactggc ctctctgcag    7980
atcaagt                                                              7987
```

<210> SEQ ID NO 6
<211> LENGTH: 7989
<212> TYPE: DNA
<213> ORGANISM: Hepatitis C virus

<400> SEQUENCE: 6

```
gccagccccc gattgggggc gacactccac catagatcac tcccctgtga ggaactactg     60
tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta tgttgggtc gcgaaaggcc ttgtggtact gcctgatagg    300
gtgcttgcga gtccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc agggggcgcc cggttctttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
```

-continued

```
cattcgacca ccaagcgaaa catcgcatcg agcgagcacg tactcggatg gaagccggtc        840
ttgtcgatca ggatgatctg gacgaagagc atcaggggct cgcgccagcc gaactgttcg        900
ccaggctcaa ggcgcgcatg cccgacggcg aggatctcgt cgtgacccat ggcgatgcct        960
gcttgccgaa tatcatggtg gaaaatggcc gcttttctgg attcatcgac tgtggccggc       1020
tgggtgtggc ggaccgctat caggacatag cgttggctac ccgtgatatt gctgaagagc       1080
ttggcggcga atgggctgac cgcttcctcg tgctttacgg tatcgccgct cccgattcgc       1140
agcgcatcgc cttctatcgc cttcttgacg agttcttctg agtttaaaca gaccacaacg       1200
gtttccctct agcgggatca attccgcccc tctccctccc cccccctaa cgttactggc        1260
cgaagccgct tggaataagg ccggtgtgcg tttgtctata tgttattttc caccatattg       1320
ccgtcttttg gcaatgtgag ggcccggaaa cctggccctg tcttcttgac gagcattcct       1380
aggggtcttt cccctctcgc caaggaatg  caaggtctgt tgaatgtcgt gaaggaagca       1440
gttcctctgg aagcttcttg aagacaaaca acgtctgtag cgacccttttg caggcagcgg      1500
aaccccccac ctgcgacag  gtgcctctgc ggccaaaagc cacgtgtata agatacacct       1560
gcaaaggcgg cacaacccca gtgccacgtt gtgagttgga tagttgtgga aagagtcaaa       1620
tggctctcct caagcgtatt caacaagggg ctgaaggatg cccagaaggt accccattgt       1680
atgggatctg atctggggcc tcggtgcaca tgctttacat gtgtttagtc gaggttaaaa       1740
aacgtctagg cccccccgaac cacggggacg tggttttcct ttgaaaaaca cgataatacc      1800
atggcgccta ttacggccta ctcccaacag acgcgaggcc tacttggctg catcatcact       1860
agcctcacag gccgggacag gaaccaggtc gaggggagg  tccaagtggt ctccaccgca       1920
acacaatctt tcctggcgac ctgcgtcaat ggcgtgtgtt ggactgtcta tcatggtgcc       1980
ggctcaaaga cccttgccgg cccaaagggc ccaatcaccc aaatgtacac caatgtggac       2040
caggacctcg tcggctggca agcgcccccc ggggcgcgtt ccttgacacc atgcacctgc       2100
ggcagctcgg accttttactt ggtcacgagg catgccgatg tcattccggt gcgccggcgg      2160
ggcgacagca gggggagcct actctccccc aggcccgtct cctacttgaa gggctcttcg       2220
ggcggtccac tgctctgccc ctcggggcac gctgtgggca tctttcgggc tgccgtgtgc       2280
acccgagggg ttgcgaaggc ggtggacttt gtaccccgtcg agtctatgga aaccactatg      2340
cggtccccgg tcttcacgga caactcgtcc cctccggccg taccgcagac attccaggtg       2400
gcccatctac acgcccctac tggtagcggc aagagcacta aggtgccggc tgcgtatgca       2460
gcccaagggt ataaggtgct tgtcctgaac ccgtccgtcg ccgccaccct aggtttcggg       2520
gcgtatatgt ctaaggcaca tggtatcgac cctaacatca gaaccggggt aaggaccatc       2580
accacgggtg cccccatcac gtactccacc tatggcaagt tccttgccga cggtggttgc       2640
tctgggggcg cctatgacat cataatatgt gatgagtgcc actcaactga ctcgaccact       2700
atcctgggca tcggcacagt cctggaccaa gcggagacgc tggagcgcg  actcgtcgtg       2760
ctcgccaccg ctacgcctcc gggatcggtc accgtgccac atccaaacat cgaggaggtg       2820
gctctgtcca gcactggaga aatccccttt tatggcaaag ccatccccat cgagaccatc       2880
aagggggga  ggcacctcat tttctgccat tccaagaaga aatgtgatga gctcgccgcg       2940
aagctgtccg gcctcggact caatgctgta gcatattacc ggggccttga tgtatccgtc       3000
ataccaacta gcggagacgt cattgtcgta gcaacggacg ctctaatgac gggctttacc       3060
ggcgatttcg actcagtgat cgactgcaat acatgtgtca cccagacagt cgacttcagc       3120
ctggacccga ccttcaccat tgagacgacg accgtgccac aagacgcggt gtcacgctcg       3180
```

```
cagcggcgag gcaggactgg tagggcagg atgggcattt acaggtttgt gactccagga     3240
gaacggccct cgggcatgtt cgattcctcg gttctgtgcg agtgctatga cgcgggctgt     3300
gcttggtacg agctcacgcc cgccgagacc tcagttaggt tgcgggctta cctaaacaca     3360
ccagggttgc ccgtctgcca ggaccatctg gagttctggg agagcgtctt tacaggcctc     3420
acccacatag acgcccattt cttgtcccag actaagcagg caggagacaa cttcccctac     3480
ctggtagcat accaggctac ggtgtgcgcc agggctcagg ctccacctcc atcgtgggac     3540
caaatgtgga agtgtctcat acggctaaag cctacgctgc acgggccaac gccctgctg      3600
tataggctgg gagccgttca aaacgaggtt actaccacac accccataac caaatacatc     3660
atggcatgca tgtcggctga cctggaggtc gtcacgagca cctgggtgct ggtaggcgga     3720
gtcctagcag ctctggccgc gtattgcctg acaacaggca gcgtggtcat tgtgggcagg     3780
atcatcttgt ccggaaagcc ggccatcatt cccgacaggg aagtccttta ccgggagttc     3840
gatgagatgg aagagtgcgc ctcacacctc ccttacatcg aacagggaat gcagctcgcc     3900
gaacaattca acagaaggc aatcggggttg ctgcaaacag ccaccaagca agcggaggct     3960
gctgctcccg tggtggaatc caagtggcgg accctcgaag ccttctgggc gaagcatatg     4020
tggaatttca tcagcgggat acaatattta gcaggcttgt ccactctgcc tggcaacccc     4080
gcgatagcat cactgatggc attcacagcc tctatcacca gcccgctcac cacccaacat     4140
accctcctgt ttaacatcct ggggggatgg gtggccgccc aacttgctcc tcccagcgct     4200
gcttctgctt tcgtaggcgc cggcatcgct ggagcggctg ttggcagcat aggccttggg     4260
aaggtgcttg tggatatttt ggcaggttat ggagcagggg tggcaggcgc gctcgtggcc     4320
tttaaggtca tgagcggcga gatgccctcc accgaggacc tggttaacct actccctgct     4380
atcctctccc ctggcgccct agtcgtcggg gtcgtgtgcg cagcgatact gcgtcggcac     4440
gtgggcccag gggagggggc tgtgcagtgg atgaaccggc tgatagcgtt cgcttcgcgg     4500
ggtaaccacg tctccccac gcactatgtg cctgagagcg acgctgcagc acgtgtcact     4560
cagatcctct ctagtcttac catcactcag ctgctgaaga ggcttcacca gtggatcaac     4620
gaggactgct ccacgccatg ctccggctcg tggctaagag atgtttggga ttggatatgc     4680
acggtgttga ctgatttcaa gacctggctc cagtccaagc cctgccgcg attgccggga     4740
gtccccttct tctcatgtca acgtgggtac aagggagtct ggcggggcga cggcatcatg     4800
caaaccacct gccatgtgg agcacagatc accggacatg tgaaaaacgg ttccatgagg     4860
atcgtgggc ctaggacctg tagtaacacg tggcatggaa cattccccat taacgcgtac     4920
accacgggcc cctgcacgcc ctcccgggcg ccaaattatt ctaggcgct gtggcgggtg     4980
gctgctgagg agtacgtgga ggttacgcgg gtgggggatt tccactacgt gacgggcatg     5040
accactgaca cgtaaagtg cccgtgtcag gttccggccc ccgaattctt cacagaagtg     5100
gatggggtgc ggttgcacag gtacgctcca gcgtgcaaac ccctcctacg ggaggaggtc     5160
acattcctgg tcgggctcaa tcaatacctg gttgggtcac agctcccatg cgagcccgaa     5220
ccggacgtag cagtgctcac ttccatgctc accgaccct cccacattac ggcggagacg     5280
gctaagcgta ggctggccag gggatctccc cctccttgg ccagctcatc agctagccag     5340
ctgtctgcgc cttccttgaa ggcaacatgc actacccgtc atgactcccc ggacgctgac     5400
ctcatcgagg ccaacctcct gtggcggcag gagatgggcg gaacatcac ccgcgtggag     5460
tcagaaaata aggtagtaat tttggactct ttcgagccgc tccaagcgga ggaggatgag     5520
```

```
agggaagtat ccgttccggc ggagatcctg cggaggtcca ggaaattccc tcgagcgatg   5580
cccatatggg cacgcccgga ttacaaccct ccactgttag agtcctggaa ggacccggac   5640
tacgtccctc cagtggtaca cgggtgtcca ttgccgcctg ccaaggcccc tccgatacca   5700
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc ccccccttga gggggagccg ggggatcccg atctcagcga cgggtcttgg   5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tggggcaaag   6300
gacgtccgga acctatccag caaggccgtt aaccacatcc gctccgtgtg gaaggacttg   6360
ctggaagaca ctgagacacc aattgacacc accatcatgg caaaaaatga ggttttctgc   6420
gtccaaccag agaaggggg ccgcaagcca gctcgcctta tcgtattccc agatttgggg   6480
gttcgtgtgt gcgagaaaat ggcccttttac gatgtggtct ccaccctccc tcaggccgtg   6540
atgggctctt catacggatt ccaatactct cctggacagc gggtcgagtt cctggtgaat   6600
gcctggaaag cgaagaaatg ccctatgggc ttcgcatatg acacccgctg ttttgactca   6660
acggtcactg agaatgacat ccgtgttgag gagtcaatct accaatgttg tgacttggcc   6720
cccgaagcca gacaggccat aaggtcgctc acagagcggc tttacatcgg gggcccctg   6780 actaattcta aagggcagaa ctgccggcta tcgccggtgc cgcgcgagcgg tgtactgacg   6840 accagctgcg gtaatacccct cacatgttac ttgaaggccg ctgcggcctg tcgagctgcg   6900
aagctccagg actgcacgat gctcgtatgc ggagacgacc ttgtcgttat ctgtgaaagc   6960
gcggggaccc aagaggacga ggcgagccta cgggccttca cggaggctat gactagatac   7020 tctgccccc ctggggaccc gcccaaacca gaatacgact tggagttgat aacatcatgc   7080
tcctccaatg tgtcagtcgc gcacgatgca tctggcaaaa gggtgtacta tctcacccgt   7140
gaccccacca ccccccttgc gcgggctgcg tgggagacag ctagacacac tccagtcaat   7200
tcctggctag gcaacatcat catgtatgcg cccaccttgt gggcaaggat gatcctgatg   7260
actcatttct tctccatcct tctagctcag gaacaacttg aaaaagccct agattgtcag   7320
atctacgggg cctgttactc cattgagcca cttgacctac tcagatcat tcaacgactc   7380 catggcctta gcgcattttc actccatagt tactctccag gtgagatcaa tagggtggct   7440
tcatgcctca ggaaacttgg ggtaccgccc ttgcgagtct ggacacatcg ggccagaagt   7500
gtccgcgcta ggctactgtc ccagggggg agggctgcca cttgtggcaa gtacctcttc   7560
aactgggcag taaggaccaa gctcaaactc actccaatcc cggctgcgtc ccagttggat   7620
ttatccagct ggttcgttgc tggttacagc ggggagaca tatatcacag cctgtctcgt   7680
gcccgacccc gctggttcat gtggtgccta ctcctacttt ctgtagggg aggcatctat   7740 ctactcccca accgatgaac ggggacctaa acactccagg ccaataggcc atcctgtttt   7800
tttccctttt ttttttcctt tttttttttt tttttttttt tctcctttt   7860 tttttcctct tttttccctt tcctttcctt tggtggctcc atcttagccc tagtcacggc   7920
```

```
tagctgtgaa aggtccgtga gccgcttgac tgcagagagt gctgatactg gcctctctgc    7980
agatcaagt                                                              7989

<210> SEQ ID NO 7
<211> LENGTH: 7848
<212> TYPE: DNA
<213> ORGANISM: Hepatitis C virus

<400> SEQUENCE: 7
gccagccccc gattgggggc gacactccac catagatcac tccctgtga ggaactactg      60 tcttcacgca gaaagcgtct agccatggcg ttagtatgag tgtcgtgcag cctccaggac    120 ccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg aagccggtc    840 ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc   1260 cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgacccttg caggcagcgg   1500 aaccccccac ctggcgacag tgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt acccccattgt   1680 atgggatctg atctggggcc tcggtgcaca tgctttacat gtgtttagtc gaggttaaaa   1740
aacgtctagg ccccccgaac cacggggacg tggttttcct ttgaaaaaca cgataatacc   1800
atggcgccta ttacggccta ctcccaacag acgcgaggc tacttggctg catcatcact   1860
agcctcacag gccggacag gaaccaggtc gaggggagg tccaagtggt ctccaccgca   1920
acacaatctt tcctggcgac ctgcgtcaat ggcgtgtgtt ggactgtcta tcatggtgcc   1980
```

```
ggctcaaaga cccttgccgg cccaaagggc ccaatcaccc aaatgtacac caatgtggac    2040
caggacctcg tcggctggca agcgccccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt tcttgccga cggtggttgc     2640 tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880
aaggggggga ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct    4380
```

```
atcctctccc ctggcgccct agtcgtcggg gtcgtgtgcg cagcgatact gcgtcggcac   4440
gtgggcccag ggaggggc tgtgcagtgg atgaaccggc tgatagcgtt cgcttcgcgg    4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtcccctct tctcatgtca acgtgggtac aagggagtct ggcggggcga cggcatcatg    4800
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtggggatt tccactacgt gacgggcatg    5040
accactgaca acgtaaagtg cccgtgtcag gttccggccc ccgaattctt cacagaagtg   5100
gatggggtgc ggttgcacag gtacgctcca gcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgaccct cccacattac ggcggagacg    5280
gctaagcgta ggctggccag gggatctccc ccctccttgg ccagctcatc agctagccag   5340
ctgtactctt tcgagccgct ccaagcggag gaggatgaga gggaagtatc cgttccggcg   5400
gagatcctgc ggaggtccag gaaattccct cgagcgatgc ccatatgggc acgcccggat   5460
tacaaccctc cactgttaga gtcctggaag gacccggact acgtccctcc agtggtacac   5520
gggtgtccat tgccgcctgc caaggccct ccgataccac ctccacgag gaagaggacg     5580
gttgtcctgt cagaatctac cgtgtcttct gccttggcgg agctcgccac aaagaccttc   5640
ggcagctccg aatcgtcggc cgtcgacagc ggcacggcaa cggcctctcc tgaccagccc   5700
tccgacgacg gcgacgcggg atccgacgtt gagtcgtact cctccatgcc cccccttgag   5760
ggggagccgg gggatcccga tctcagcgac gggtcttggt ctaccgtaag cgaggaggct   5820
agtgaggacg tcgtctgctg ctcgatgtcc tacacatgga caggcgccct gatcacgcca   5880
tgcgctgcgg aggaaaccaa gctgcccatc aatgcactga gcaactcttt gctccgtcac   5940
cacaacttgg tctatgctac aacatctcgc agcgcaagcc tgcggcagaa gaaggtcacc   6000
tttgacagac tgcaggtcct ggacgaccac taccgggacg tgctcaagga gatgaaggcg   6060
aaggcgtcca cagttaaggc taaacttcta tccgtggagg aagcctgtaa gctgacgccc   6120
ccacattcgg ccagatctaa atttggctat ggggcaaagg acgtccggaa cctatccagc   6180
aaggccgtta accacatccg ctccgtgtgg aaggacttgc tggaagacac tgagacacca   6240
attgacacca ccatcatggc aaaaaatgag gttttctgcg tccaaccaga aagggggggc   6300
cgcaagccag ctcgccttat cgtattccca gatttggggg ttcgtgtgtg cgagaaaatg   6360
gcccttacg atgtggtctc caccctccct caggccgtga tgggctcttc atacggattc   6420
caatactctc ctggacagcg ggtcgagttc ctggtgaatg cctggaaagc gaagaaatgc   6480
cctatgggct tcgcatatga cacccgctgt tttgactcaa cggtcactga gaatgacatc   6540
cgtgttgagg agtcaatcta ccaatgttgt gacttggccc ccgaagccag acaggccata   6600
aggtcgctca cagagcggct ttacatcggg ggccccctga ctaattctaa agggcagaac   6660
tgcggctatc gccggtgccg cgcgagcggt gtactgacga ccagctgcgg taataccctc   6720
```

```
acatgttact tgaaggccgc tgcggcctgt cgagctgcga agctccagga ctgcacgatg    6780
ctcgtatgcg gagacgacct tgtcgttatc tgtgaaagcg cggggaccca agaggacgag    6840
gcgagcctac gggccttcac ggaggctatg actagatact ctgccccccc tgggacccg     6900 cccaaaccag aatacgactt ggagttgata acatcatgct cctccaatgt gtcagtcgcg    6960
cacgatgcat ctggcaaaag ggtgtactat ctcacccgtg accccaccac cccccttgcg    7020
cgggctgcgt gggagacagc tagacacact ccagtcaatt cctggctagg caacatcatc    7080
atgtatgcgc ccaccttgtg ggcaaggatg atcctgatga ctcatttctt ctccatcctt    7140
ctagctcagg aacaacttga aaaagcccta gattgtcaga tctacggggc tgttactcc     7200 attgagccac ttgacctacc tcagatcatt caacgactcc atggccttag cgcattttca    7260
ctccatagtt actctccagg tgagatcaat agggtggctt catgcctcag gaaacttggg    7320
gtaccgccct gcgagtctg gagacatcgg ccagaagtg tccgcgctag gctactgtcc       7380
caggggggga gggctgccac ttgtggcaag tacctcttca actgggcagt aaggaccaag    7440
ctcaaactca ctccaatccc ggctgcgtcc cagttggatt tatccagctg gttcgttgct    7500
ggttacagcg gggagacat atatcacagc ctgtctcgtg cccgaccccg ctggttcatg     7560
tggtgcctac tcctactttc tgtaggggta ggcatctatc tactccccaa ccgatgaacg    7620
gggacctaaa cactccaggc caataggcca tcctgttttt ttccctttt tttttttcttt    7680 tttttttttt tttttttttt tttttttttt tctcctttt tttcctctt tttttccttt       7740 tctttccttt ggtggctcca tcttagccct agtcacggct agctgtgaaa ggtccgtgag    7800
ccgcttgact gcagagagtg ctgatactgg cctctctgca gatcaagt               7848

<210> SEQ ID NO 8
<211> LENGTH: 7987
<212> TYPE: DNA
<213> ORGANISM: Hepatitis C virus

<400> SEQUENCE: 8
gccagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaaggg cgcgccatga ttgaacaaga tggattgcac gcaggttctc    420
cggccgcttg ggtggagagg ctattcggct atgactggga caacagaca atcggctgct    480 ctgatgccgc cgtgttccgg ctgtcagcgc agggggcgccc ggttcttttt gtcaagaccg    540
acctgtccgg tgccctgaat gaactgcagg acgaggcagc gcggctatcg tggctggcca    600
cgacgggcgt tccttgcgca gctgtgctcg acgttgtcac tgaagcggga agggactggc    660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg gaagccggtc    840
ttgtcgatca ggatgatctg gacgaagagc atcaggggct cgcgccagcc gaactgttcg    900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc    1020
```

```
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc    1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaggaatg caaggtctgt tgaatgtcgt gaaggaagca    1440
gttcctctgg aagcttcttg aagacaaaca acgtctgtag cgacccttg caggcagcgg    1500
aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc   1800
atggcgccta ttacggccta ctcccaacag acgcgaggcc tacttggctg catcatcact   1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggcg agcgcccccc ggggcgcgtt ccttgacacc atgcacctgc   2100
ggcagctcgg accttactt ggtcacgagg catgccgatg tcattccggt gcgccggcgg    2160
ggcgacagca gggggagcct actctccccc aggcccgtct cctacttgaa gggctcttcg   2220
ggcggtccac tgctctgccc ctcggggcac gctgtgggca tctttcgggc tgccgtgtgc   2280
acccgagggg ttgcgaaggc ggtggactt gtacccgtcg agtctatgga aaccactatg    2340
cggtcccgg tcttcacgga caactcgtcc cctccggccg taccgcagac attccaggtg    2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacggtg ccccatcac gtactccacc tatggcaagt ttcttgccga cggtggttgc    2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatcccctt tatggcaaag ccatccccat cgagaccatc    2880
aagggggga ggcacctcat tttctgccat tccaagaaga aatgtgatga gctcgccgcg    2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg tagggcagg atgggcattt acaggtttgt gactccagga   3240
gaacggccct cggcatgtt cgattcctcg gttctgtgcg agtgctatga cgcgggctgt   3300
gcttggtacg agctcacgcc cgccgagacc tcagttaggt tgcgggctta cctaaacaca   3360
```

```
ccagggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtgga agtgtctcat acggctaaag cctacgctgc acgggccaac gcccctgctg   3600
tataggctgg gagccgttca aaacgaggtt actaccacac accccataac caaatacatc   3660
atggcatgca tgtcggctga cctggaggtc gtcacgagcc cctgggtgct ggtaggcgga   3720
gtcctagcag ctctggccgc gtattgcctg acaacaggca gcgtggtcat tgtgggcagg   3780
atcatcttgt ccggaaagcc ggccatcatt cccgacaggg aagtcctttca ccgggagttc   3840 gatgagatgg aagagtgcgc ctcacacctc ccttacatcg aacagggaat gcagctcgcc   3900
gaacaattca aacagaaggc aatcggggttg ctgcaaacag ccaccaagca agcggaggct   3960
gctgctcccg tggtggaatc caagtggcgg accctcgaag ccttctgggc gaagcatatg   4020 tggaattca tcagcgggat acaatattta gcaggcttgt ccactctgcc tggcaaccc   4080 gcgatagcat cactgatggc attcacagcc tctatcacca gcccgctcac cacccaacat   4140
accctcctgt ttaacatcct gggggatgg gtggccgccc aacttgctcc tcccagcgct   4200
gcttctgctt tcgtaggcgc cggcatcgct ggagcggctg ttggcagcat aggccttggg   4260
aaggtgcttg tggatattt ggcaggttat ggagcagggg tggcaggcgc gctcgtggcc   4320
tttaaggtca tgagcggcga gatgcctcc accgaggacc tggttaacct actccctgct   4380
atcctctccc ctggcgccct agtcgtcggg gtcgtgtgcg cagcgatact gcgtcggcac   4440
gtgggcccag gggaggggc tgtgcagtgg atgaaccggc tgatagcgtt cgcttcgcgg   4500
ggtaaccacg tctcccccac gcactatgtg cctgagagcg acgctgcagc acgtgtcact   4560
cagatcctct ctagtcttac catcactcag ctgctgaaga ggcttcacca gtggatcaac   4620
gaggactgct ccacgccatg ctccggctcg tggctaagag atgtttggga ttggatatgc   4680
acggtgttga ctgatttcaa gacctggctc cagtccaagc tcctgccgcg attgccggga   4740
gtccccttct tctcatgtca acgtgggtac aagggagtct ggcggggcga cggcatcatg   4800
caaaccacct gcccatgtgg agcacagatc accggacatg tgaaaaacgg ttccatgagg   4860
atcgtggggc ctaggacctg tagtaacacg tggcatggaa cattccccat taacgcgtac   4920
accacgggcc cctgcacgcc ctccccggcg ccaaattatt ctagggcgct gtggcgggtg   4980
gctgctgagg agtacgtgga ggttacgcgg gtggggatt tccactacgt gacgggcatg   5040
accactgaca acgtaaagtg cccgtgtcag gttccggccc ccgaattctt cacagaagtg   5100
gatggggtgc ggttgcacag gtacgctcca cgcgtgcaaac ccctcctacg ggaggaggtc   5160
acattcctgg tcgggctcaa tcaatacctg gttgggtcac agctcccatg cgagcccgaa   5220
ccggacgtag cagtgctcac ttccatgctc accgacccct cccacattac ggcggagacg   5280
gctaagcgta ggctggccag gggatctccc cctccttgg ccagctcatc agctatccag   5340
ctgtctgcgc cttccttgaa ggcaacatgc actacccgtc atgactcccc ggacgctgac   5400
ctcatcgagg ccaacctcct gtggcggcag gagatgggcg gaacatcac ccgcgtggag   5460 tcagaaaata aggtagtaat tttggactct ttcgagccgc tccaagcgga ggaggatgag   5520
agggaagtat ccgttccggc ggagatcctg cggaggtcca ggaaattccc tcgagcgatg   5580
cccatatggg cacgcccgga ttacaaccct ccactgttag agtcctggaa ggaccccgac   5640
tacgtccctc cagtggtaca cggggtgtcca ttgccgcctg ccaaggcccc tccgatacca   5700
cctccacgga ggaagaggac ggttgtcctg tcagaatcta ccgtgtcttc tgccttggcg   5760
```

```
gagctcgcca caaagacctt cggcagctcc gaatcgtcgg ccgtcgacag cggcacggca      5820
acggcctctc ctgaccagcc ctccgacgac ggcgacgcgg gatccgacgt tgagtcgtac      5880
tcctccatgc ccccccttga gggggagccg ggggatcccg atctcagcga cgggtcttgg      5940
tctaccgtaa gcgaggaggc tagtgaggac gtcgtctgct gctcgatgtc ctacacatgg      6000
acaggcgccc tgatcacgcc atgcgctgcg gaggaaacca agctgcccat caatgcactg      6060
agcaactctt tgctccgtca ccacaacttg gtctatgcta caacatctcg cagcgcaagc      6120
ctgcggcaga agaaggtcac ctttgacaga ctgcaggtcc tggacgacca ctaccgggac      6180
gtgctcaagg agatgaaggc gaaggcgtcc acagttaagg ctaaacttct atccgtggag      6240
gaagcctgta agctgacgcc cccacattcg gccagatcta aatttggcta tgggggcaaag      6300
gacgtccgga acctatccag caaggccgtt aaccacatcc gctccgtgtg aaggacttg       6360
ctggaagaca ctgagacacc aattgacacc accatcatgg caaaaaatga gttttctgc       6420
gtccaaccag agaaggggg ccgcaagcca gctcgcctta tcgtattccc agatttgggg       6480
gttcgtgtgt gcgagaaaat ggcccttttac gatgtggtct ccaccctccc tcaggccgtg     6540
atgggctctt catacggatt ccaatactct cctggacagc gggtcgagtt cctggtgaat      6600
gcctggaaag cgaagaaatg ccctatgggc ttcgcatatg acacccgctg ttttgactca      6660
acggtcactg agaatgacat ccgtgttgag gagtcaatct accaatgttg tgacttggcc      6720
cccgaagcca gacaggccat aaggtcgctc acagagcggc tttacatcgg gggcccctg      6780
actaattcta aagggcagaa ctgcggctat cgccggtgcc gcgcgagcgg tgtactgacg      6840
accagctgcg gtaataccct cacatgttac ttgaaggccg ctgcggcctg tcgagctgcg      6900
aagctccagg actgcacgat gctcgtatgc ggagacgacc ttgtcgttat ctgtgaaagc      6960
gcggggaccc aagaggacga ggcgagccta cgggccttca cggaggctat gactagatac      7020
tctgccccc ctggggaccc gcccaaacca gaatacgact tggagttgat aacatcatgc       7080
tcctccaatg tgtcagtcgc gcacgatgca tctggcaaaa gggtgtacta tctcacccgt      7140
gaccccacca ccccccttgc gcgggctgcg tgggagacag ctagacacac tccagtcaat      7200
tcctggctag caacatcat catgtatgcg cccaccttgt gggcaaggat gatcctgatg       7260
actcatttct tctccatcct tctagctcag gaacaacttg aaaaagccct agattgtcag      7320
atctacgggg cctgttactc cattgagcca cttgacctac ctcagatcat tcaacgactc      7380
catgccctta gcgcattttc actccatagt tactctccag gtgagatcaa tagggtggct      7440
tcatgcctca ggaaacttgg ggtaccgccc ttgcgagtct ggagacatcg ggccagaagt      7500
gtccgcgcta ggctactgtc ccaggggggg agggctgcca cttgtggcaa gtacctcttc      7560
aactgggcag taaggaccaa gctcaaactc actccaatcc cggctgcgtc ccagttggat      7620
ttatccagct ggttcgttgc tggttacagc ggggagaca tatatcacag cctgtctcgt      7680
gcccgacccc gctggttcat gtggtgccta ctcctacttt ctgtaggggt aggcatctat      7740
ctactcccca accgatgaac ggggagctaa acactccagg ccaataggcc atcctgtttt      7800
tttcccttt ttttttttctt ttttttttt tttttttttt ttttttttt ctcctttttt         7860
tttcctcttt ttttccttt ctttccttg gtggctccat cttagcccta gtcacggcta         7920
gctgtgaaag gtccgtgagc cgcttgactg cagagagtgc tgatactggc ctctctgcag      7980
atcaagt                                                                 7987
```

<210> SEQ ID NO 9

<211> LENGTH: 7989
<212> TYPE: DNA
<213> ORGANISM: Hepatitis C virus

<400> SEQUENCE: 9

```
gccagccccc gattgggggc gacactccac catagatcac tccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg aagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc    1260
cgaagccgct tggaataagg ccggtgtgcg tttgtctata tgttatttc caccatattg    1320
ccgtcttttg gcaatgtgag ggcccggaaa cctggccctg tcttcttgac gagcattcct    1380
aggggtcttt cccctctcgc caaggaatg caaggtctgt tgaatgtcgt gaaggaagca    1440
gttcctctgg aagcttcttg aagacaaaca acgtctgtag cgacccttg caggcagcgg    1500
aaccccccac ctggcgacag tgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt acccattgt    1680
atgggatctg atctggggcc tcggtgcaca tgctttacat gtgtttagtc gaggttaaaa    1740
aacgtctagg cccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggaggg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgccccc ggggcgcgtt ccttgacacc atgcacctgc    2100
ggcagctcgg acctttactt ggtcacgagg catgccgatg tcattccggt gcgcggcgg    2160
ggcgacagca gggggagcct actctccccc aggccccgtct cctacttgaa gggctcttcg    2220
```

```
ggcggtccac tgctctgccc ctcggggcac gctgtgggca tctttcgggc tgccgtgtgc   2280
acccgagggg ttgcgaaggc ggtggacttt gtacccgtcg agtctatgga aaccactatg   2340
cggtccccgg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatggcaagt tcttgccga cggtggttgc   2640 tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatccccttt tatggcaaag ccatccccat cgagaccatc   2880 aagggggggga ggcacctcat tttctgccat tccaagaaga aatgtgatga gctcgccgcg   2940
aagctgtccg gcctcggact caatgctgta gcatattacc ggggccttga tgtatccgtc   3000
ataccaacta gcggagacgt cattgtcgta gcaacggacg ctctaatgac gggctttacc   3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag caggactgg tagggggcagg atgggcattt acaggtttgt gactccagga   3240
gaacggccct cgggcatgtt cgattcctcg gttctgtgcg agtgctatga cgcgggctgt   3300
gcttggtacg agctcacgcc cgccgagacc tcagttaggt tgcgggctta cctaaacaca   3360 ccaggggttgc ccgtctgcca ggaccatctg gagttctggg agagcgtctt tacaggcctc   3420
acccacatag acgcccattt cttgtcccag actaagcagg caggagacaa cttcccctac   3480
ctggtagcat accaggctac ggtgtgcgcc agggctcagg ctccacctcc atcgtgggac   3540
caaatgtggg agtgtctcat acggctaaag cctacgctgc acgggccaac gcccctgctg   3600
tataggctgg gagccgttca aaacgaggtt actaccacac accccataac caaatacatc   3660
atggcatgca tgtcggctga cctggaggtc gtcacgagca cctgggtgct ggtaggcgga   3720
gtcctagcag ctctggccgc gtattgcctg acaacaggca cgtggtcat tgtgggcagg   3780 atcatcttgt ccggaaagcc ggccatcatt cccgacaggg aagtccttta ccgggagttc   3840
gatgagatgt aagagtgcgc ctcacacctc ccttacatcg aacagggaat gcagctcgcc   3900
gaacaattca acagaaggc aatcgggttg ctgcaaacag ccaccaagca agcggaggct   3960
gctgctcccg tggtggaatc caagtggcgg accctcgaag ccttctgggc gaagcatatg   4020
tggaatttca tcagcgggat acaatatttta gcaggcttgt ccactctgcc tggcaacccc   4080
gcgatagcat cactgatggc attcacagcc tctatcacca gcccgctcac cacccaacat   4140
accctcctgt ttaacatcct ggggggatgg gtggccgccc aacttgctcc tcccagcgct   4200
gcttctgctt tcgtaggcgc cggcatcgct ggagcggctg ttggcagcat aggccttggg   4260
aaggtgcttg tggatatttt ggcaggttat ggagcagggg tggcaggcgc gctcgtggcc   4320
tttaaggtca tgagcggcga gatgcccctcc accgaggacc tggttaacct actccctgct   4380
atcctctccc ctggcgccct agtcgtcggg gtcgtgtgcg cagcgatact gcgtcggcac   4440
gtgggcccag ggggagggggc tgtgcagtgg atgaaccgcc tgatagcgtt cgcttcgcgg   4500
ggtaaccacg tctcccccac gcactatgtg cctgagagcg acgctgcagc acgtgtcact   4560
```

```
cagatcctct ctggtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtgggggatt ccactacgt gacgggcatg    5040 accactgaca acgtaaagtg cccgtgtcag gttccggccc ccgaattctt cacagaagtg    5100 gatgggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgaccct cccacattac ggcggagacg    5280
gctaagcgtg ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460 tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga ggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac cttttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatg caaaaaatga ggttttctgc    6420
gtccaaccag agaaggggg ccgcaagcca gctcgcctta tcgtattccc agatttgggg    6480
gttcgtgtgt gcgagaaaat ggcccttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg    6780 actaattcta aagggcagaa ctgcggctat cgccggtgcc gcgcgagcgg tgtactgacg    6840
accagctgcg gtaatacct cacatgttac ttgaaggccg ctgcggcctg tcgagctgcg    6900
aagctccagg actgcacgat gctcgtatgc ggagacgacc ttgtcgttat ctgtgaaagc    6960
```

-continued

| | |
|---|---|
| gcggggaccc aagaggacga ggcgagccta cgggccttca cggaggctat gactagatac | 7020 |
| tctgccccc ctggggaccc gcccaaacca gaatacgact tggagttgat aacatcatgc | 7080 |
| tcctccaatg tgtcagtcgc gcacgatgca tctggcaaaa gggtgtacta tctcacccgt | 7140 |
| gaccccacca ccccccttgc gcgggctgcg tgggagacag ctagacacac tccagtcaat | 7200 |
| tcctggctag gcaacatcat catgtatgcg cccaccttgt gggcaaggat gatcctgatg | 7260 |
| actcatttct tctccatcct tctagctcag gaacaacttg aaaaagccct agattgtcag | 7320 |
| atctacgggg cctgttactc cattgagcca cttgacctac ctcagatcat tcaacgactc | 7380 |
| catggcctta gcgcattttc actccatagt tactctccag gtgagatcaa tagggtggct | 7440 |
| tcatgcctca ggaaacttgg ggtaccgccc ttgcgagtct ggagacatcg ggccagaagt | 7500 |
| gtccgcgcta ggctactgtc ccaggggggg agggctgcca cttgtggcaa gtacctcttc | 7560 |
| aactgggcag taaggaccaa gctcaaactc actccaatcc cggctgcgtc ccagttggat | 7620 |
| ttatccagct ggttcgttgc tggttacagc ggggagaca tatatcacag cctgtctcgt | 7680 |
| gcccgacccc gctggttcat gtggtgccta ctcctacttt ctgtaggggt aggcatctat | 7740 |
| ctactcccca accgatgaac ggggacctaa acactccagg ccaataggcc atcctgtttt | 7800 |
| tttccctttt ttttttttctt tttttttttt tttttttttt tttttttttt ttctcctttt | 7860 |
| tttttcctct tttttttcctt ttctttcctt tggtggctcc atcttagccc tagtcacggc | 7920 |
| tagctgtgaa aggtccgtga gccgcttgac tgcagagagt gctgatactg gcctctctgc | 7980 |
| agatcaagt | 7989 |

<210> SEQ ID NO 10
<211> LENGTH: 7989
<212> TYPE: DNA
<213> ORGANISM: Hepatitis C virus

<400> SEQUENCE: 10

| | |
|---|---|
| gccagccccc gattggggc gacactccac catagatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tccttttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc agggggcgcc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcagggct cgcgccagcc gaactgttcg | 900 |
| ccaggctcaa ggcgcgcatg cccgacgcg aggatctcgt cgtgacccat ggcgatgcct | 960 |
| gcttgccgaa tatcatggtg gaaaatggcc gcttttctgg attcatcgac tgtggccggc | 1020 |

-continued

```
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc ccccccctaa cgttactggc    1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgacccttttg caggcagcgg    1500 aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc    1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtaccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
ctcgccaccg ctacgcctcc gggatcggtc accgtgccac atccaaacat cgaggaggtg    2820
gctctgtcca gcactggaga aatccccttt tatggcaaag ccatccccat cgagaccatc    2880 aagggggggaa ggcacctcat tttctgccat tccaagaaga aatgtgatga gctcgccgcg    2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg tagggggcagg atgggcattt acaggtttgt gactccagga    3240
gaacggccct cggcatgttt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
```

-continued

```
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcggggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatggg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcccctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctcccggcg ccaaattatt ctagggcgct gtggcgggtg    4980
gctgctgagg agtacgtgga ggttacgcgg gtgggggatt ccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaataccctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgt ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
```

```
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga ggggagccg ggggatcccg atctcagcga cgggtcttgg     5940
tctaccgtaa gcgaggaggc tagtgaggac gtcgtctgct gctcgatgtc ctacacatgg    6000
acaggcgccc tgatcacgcc atgcgctgcg aggaaacca agctgcccat caatgcactg     6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaaggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg gggccccctg    6780
actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020
tctgcccccc ctggggaccc gcccaaacca gaatacgact tggagttgat aacatcatgc    7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagcct agattgtcag    7320
atctacgggg cctgttactc cattgagcca cttgacctac tcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccagggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc gggggagaca tatatcacag cctgtctcgt    7680
gcccgaccc gctggttcat gtggtgccta ctcctacttt ctgtagggt aggcatctat    7740
ctactcccca accgatgaac ggggacctaa acactccagg ccaataggcc atcctgtttt    7800
tttcccttt tttttttctt ttttttttt ttttttttt tttttttttt ttctcctttt    7860
tttttcctct ttttttcctt ttctttcctt tggtggctcc atcttagccc tagtcacggc    7920
tagctgtgaa aggtccgtga gccgcttgac tgcagagagt gctgatactg gcctctctgc    7980
agatcaagt                                                           7989
```

```
<210> SEQ ID NO 11
<211> LENGTH: 1341
```

<212> TYPE: DNA
<213> ORGANISM: Hepatitis C virus

<400> SEQUENCE: 11

```
tccggctcgt ggctaagaga tgtttgggat tggatatgca cggtgttgac tgatttcaag      60
acctggctcc agtccaagct cctgccgcga ttgccgggag tccccttctt ctcatgtcaa     120
cgtgggtaca agggagtctg gcggggcgac ggcatcatgc aaaccacctg cccatgtgga     180
gcacagatca ccggacatgt gaaaaacggt tccatgagga tcgtggggcc taggacctgt     240
agtaacacgt ggcatggaac attccccatt aacgcgtaca ccacgggccc ctgcacgccc     300
tccccggcgc caaattattc tagggcgctg tggcggtgg ctgctgagga gtacgtggag      360
gttacgcggg tgggggattt ccactacgtg acgggcatga ccactgacaa cgtaaagtgc     420
ccgtgtcagg ttccggcccc cgaattcttc acagaagtgg atggggtgcg gttgcacagg     480
tacgctccag cgtgcaaacc cctcctacgg gaggaggtca cattcctggt cgggctcaat     540
caatacctgg ttgggtcaca gctcccatgc gagcccgaac cggacgtagc agtgctcact     600
tccatgctca ccgacccctc ccacattacg gcggagacgg ctaagcgtag gctggccagg     660
ggatctcccc cctgcttggc cagctcatca gctagccagc tgtctgcgcc ttccttgaag     720
gcaacatgca ctacccgtca tgactccccg gacgctgacc tcatcgaggc caacctcctg     780
tggcggcagg agatgggcgg gaacatcacc cgcgtggagt cagaaaataa ggtagtaatt     840
ttggactctt tcgagccgct ccaagcggag gaggatgaga ggaagtatc cgttccggcg      900
gagatcctgc ggaggtccag gaaattccct cgagcgatgc ccatatgggc acgcccggat     960
tacaaccctc cactgttaga gtcctggaag gacccggact acgtccctcc agtggtacac    1020
gggtgtccat gccgcctgc caaggcccct ccgataccac ctccacgag aagaggacg      1080
gttgtcctgt cagaatctac cgtgtcttct gccttggcgg agctcgccac aaagaccttc    1140
ggcagctccg aatcgtcggc cgtcgacagc ggcacggcaa cggcctctcc tgaccagccc    1200
tccgacgacg gcgacgcggg atccgacgtt gagtcgtact cctccatgcc ccccttgag     1260
ggggagccgg gggatcccga tctcagcgac gggtcttggt ctaccgtaag cgaggaggct    1320
agtgaggacg tcgtctgctg c                                              1341
```

<210> SEQ ID NO 12
<211> LENGTH: 1341
<212> TYPE: DNA
<213> ORGANISM: Hepatitis C virus

<400> SEQUENCE: 12

```
tccggctcgt ggctaagaga tgtttgggat tggatatgca cggtgttgac tgatttcaag      60
acctggctcc agtccaagct cctgccgcga ttgccgggag tccccttctt ctcatgtcaa     120
cgtgggtaca agggagtctg gcggggcgac ggcatcatgc aaaccacctg cccatgtgga     180
gcacagatca ccggacatgt gaaaaacggt tccatgagga tcgtggggcc taggacctgt     240
agtaacacgt ggcatggaac attccccatt aacgcgtaca ccacgggccc ctgcacgccc     300
tccccggcgc caaattattc tagggcgctg tggcggtgg ctgctgagga gtacgtggag      360
gttacgcggg tgggggattt ccactacgtg acgggcatga ccactgacaa cgtaaagtgc     420
ccgtgtcagg ttccggcccc cgaattcttc acagaagtgg atggggtgcg gttgcacagg     480
tacgctccag cgtgcaaacc cctcctacgg gaggaggtca cattcctggt cgggctcaat     540
caatacctgg ttgggtcaca gctcccatgc gagcccgaac cggacgtagc agtgctcact     600
```

| | |
|---|---:|
| tccatgctca ccgacccctc ccacattacg gcggagacgg ctaagcgtag gctggccagg | 660 |
| ggatctcccc cccccttggc cagctcatca gctagccagc tgtctgcgcc ttccttgaag | 720 |
| gcaacatgca ctacccgtca tgactccccg gacgctgacc tcatcgaggc caacctcctg | 780 |
| tggcggcagg agatgggcgg gaacatcacc cgcgtggagt cagaaaataa ggtagtaatt | 840 |
| ttggactctt tcgagccgct ccaagcggag gaggatgaga gggaagtatc cgttccggcg | 900 |
| gagatcctgc ggaggtccag gaaattccct cgagcgatgc ccatatgggc acgcccggat | 960 |
| tacaaccctc cactgttaga gtcctggaag gacccggact acgtccctcc agtggtacac | 1020 |
| gggtgtccat tgccgcctgc caaggcccct ccgataccac ctccacggag gaagaggacg | 1080 |
| gttgtcctgt cagaatctac cgtgtcttct gccttggcgg agctcgccac aaagaccttc | 1140 |
| ggcagctccg aatcgtcggc cgtcgacagc ggcacggcaa cggcctctcc tgaccagccc | 1200 |
| tccgacgacg gcgacgcggg atccgacgtt gagtcgtact cctccatgcc cccccttgag | 1260 |
| ggggagccgg gggatcccga tctcagcgac gggtcttggt ctaccgtaag cgaggaggct | 1320 |
| agtgaggacg tcgtctgctg c | 1341 |

<210> SEQ ID NO 13
<211> LENGTH: 7987
<212> TYPE: DNA
<213> ORGANISM: Hepatitis C virus

<400> SEQUENCE: 13

| | |
|---|---:|
| gccagccccc gattgggggc gacactccac catagatcac tcccctgtga ggaactactg | 60 |
| tcttcacgca gaaagcgtct agccatggcg ttagtatgag tgtcgtgcag cctccaggac | 120 |
| cccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc aggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agtttaaaca gaccacaacg | 1200 |
| gtttccctct agcgggatca attccgcccc tctcctcccc cccccctaa cgttactggc | 1260 |
| cgaagccgct tggaataagg ccggtgtgcg tttgtctata tgttattttc caccatattg | 1320 |
| ccgtcttttg gcaatgtgag ggcccggaaa cctggccctg tcttcttgac gagcattcct | 1380 |

```
aggggtctttcccctctcgcccaaaggaatgcaaggtctgttgaatgtcgtgaaggaagca      1440
gttcctctggaagcttcttgaagacaaacaacgtctgtagcgacccttgcaggcagcgg       1500
aaccccccacctggcgacaggtgcctctgcggccaaaagccacgtgtataagatacacct      1560
gcaaaggcggcacaaccccagtgccacgttgtgagttggatagttgtggaaagagtcaaa      1620
tggctctcctcaagcgtattcaacaaggggctgaaggatgcccagaaggtaccccattgt      1680
atgggatctgatctggggcctcggtgcacatgctttacatgtgtttagtcgaggttaaaa      1740
aacgtctaggcccccgaaccacggggacgtggttttccttgaaaaacacgataataacc      1800
atggcgcctattacggcctactcccaacagacgcgaggcctacttggctgcatcatcact      1860
agcctcacaggccgggacaggaaccaggtcgagggggaggtccaagtggtctccaccgca      1920
acacaatcttttcctggcgacctgcgtcaatggcgtgtgttggactgtctatcatggtgcc    1980
ggctcaaagacccttgccggcccaaagggccaatcacccaaatgtacaccaatgtggac      2040
caggacctcgtcggctggcaagcgcccccggggcgcgttccttgacaccatgcacctgc      2100
ggcagctcggaccttactttggtcacgaggcatgccgatgtcattccggtgcgccggcgg     2160
ggcgacagcagggggagcctactctccccaggcccgtctcctacttgaagggctcttcg      2220
ggcggtccactgctctgccctcggggcacgctgtgggcatctttcgggctgccgtgtgc      2280
acccgaggggttgcgaaggcggtggactttgtacccgtcgagtctatggaaaccactatg     2340
cggtccccggtcttcacggacaactcgtcccctccggccgtaccgcagacattccaggtg     2400
gcccatctacacgcccctactggtagcggcaagagcactaaggtgccggctgcgtatgca    2460
gcccaagggtataaggtgcttgtcctgaaccgtccgtcgccgccaccctaggtttcggg     2520
gcgtatatgtctaaggcacatggtatcgaccctaacatcagaaccggggtaaggaccatc     2580
accacgggtgcccccatcacgtactccacctatggcaagtttcttgccgacggtggttgc     2640
tctgggggcgcctatgacatcataaatatgtgatgagtgccactcaactgactcgaccact    2700
atcctgggcatcggcacagtcctggaccaagcggagacggctggagcgcgactcgtcgtg    2760
ctcgccaccgctacgcctccgggatcggtcaccgtgccacatccaaacatcgaggaggtg     2820
gctctgtccagcactggagaaatccccttttatggcaaagccatccccatcgagaccatc     2880
aagggggggaggcacctcattttctgccattccaagaagaaatgtgatgagctcgccgcg     2940
aagctgtccggcctcggactcaatgctgtagcatattaccggggccttgatgtatccgtc     3000
ataccaactagcggagacgtcattgtcgtagcaacggacgctctaatgacgggctttacc     3060
ggcgatttcgactcagtgatcgactgcaatacatgtgtcacccagacagtcgacttcagc     3120
ctggacccgaccttcaccattgagacgacgaccgtgccacaagacgcggtgtcacgctcg     3180
cagcggcgaggcaggactggtaggggcaggatgggcattttacaggtttgtgactccagga    3240
gaacggcccttcgggcatgttcgattcctcggttctgtgcgagtgctatgacgcgggctgt    3300
gcttggtacgagctcacgccgcgagacctcagttaggttgcgggcttaactaaacaca      3360
ccagggttgccccgtctgccaggaccatctggagttctgggagagcgtcttttacaggcctc   3420
acccacatagacgcccatttcttgtcccagactaagcaggcaggagacaacttcccctac     3480
ctggtagcataccaggctacggtgtgcgccagggctcaggctccacctccatcgtgggac     3540
caaatgtggaagtgtctcatacggctaaagcctacgctgcacgggccaacgcccctgctg     3600
tataggctgggagccgttcaaaacgaggttactaccacacacccccataacccaaatacatc    3660
atggcatgcatgtcggctgacctggaggtcgtcacgagcacctgggtgctggtaggcgga     3720
```

```
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcggggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggagggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aaggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctccccggcg ccaaattatt ctagggcgct gtggcgggtg    4980
gctgctgagg agtacgtgga ggttacgcgg gtggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctatccag    5340
ctgtctgcgc cttccttgaa ggcaacatgc actacccgtc atgactcccc ggacgctgac    5400
ctcatcgagg ccaacctcct gtggcggcag gagatgggcg gaacatcac ccgcgtggag    5460 tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cggggtgtcca ttgccgcctg ccaaggcccc tcgataccca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga gggggagccg ggggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgccat caatgcactg    6060 agcaactctt tgctccgtca ccacaacttg gtctatgcta caacatctcg cagcgcaagc    6120
```

```
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg gccagatcta aatttggcta tggggcaaag    6300
gacgtccgga acctatccag caaggccgtt aaccacatcc gctccgtgtg aaggacttg     6360 ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg acacccgctg ttttgactca    6660
acggtcactg agaatgacat ccgtgttgag gagtcaatct accaatgttg tgacttggcc    6720
cccgaagcca gacaggccat aaggtcgctc acagagcggc tttacatcgg ggcccctg     6780 actaattcta aagggcagaa ctgcggctat cgccggtgcc gcgcgagcgg tgtactgacg    6840
accagctgcg gtaataccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctggggaccc gcccaaacca gaatacgact tggagttgat aacatcatgc     7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag caacatcat catgtatgcg cccaccttgt gggcaaggat gatcctgatg      7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
gtccgcgcta ggctactgtc ccaggggggg agggctgcca cttgtggcaa gtacctcttc    7560
aactgggcag taaggaccaa gctcaaactc actccaatcc cggctgcgtc ccagttggat    7620
ttatccagct ggttcgttgc tggttacagc ggggagaca tatatcacag cctgtctcgt      7680
gcccgacccc gctggttcat gtggtgccta ctcctacttt ctgtaggggt aggcatctat    7740
ctactcccca accgatgaac ggggagctaa acactccagg ccaataggcc atcctgtttt    7800 tttcccttt tttttttctt tttttttttt tttttttttt tttttttttt ctccttttt      7860 tttcctcttt ttttcctttt ctttcctttg gtggctccat cttagcccta gtcacggcta    7920
gctgtgaaag gtccgtgagc cgcttgactg cagagagtgc tgatactggc ctctctgcag    7980
atcaagt                                                              7987
```

<210> SEQ ID NO 14
<211> LENGTH: 400
<212> TYPE: PRT
<213> ORGANISM: Hepatitis C virus

<400> SEQUENCE: 14

Ser Gly Ser Trp Leu Arg Asp Val Trp Asp Trp Ile Cys Thr Val Leu
 1               5                  10                  15

Thr Asp Phe Lys Thr Trp Leu Gln Ser Lys Leu Leu Pro Arg Leu Pro
            20                  25                  30

```
Gly Val Pro Phe Phe Ser Cys Gln Arg Gly Tyr Lys Gly Val Trp Arg
         35                  40                  45

Gly Asp Gly Ile Met Gln Thr Thr Cys Pro Cys Gly Ala Gln Ile Thr
 50                  55                  60

Gly His Val Lys Asn Gly Ser Met Arg Ile Val Gly Pro Arg Thr Cys
 65                  70                  75                  80

Ser Asn Thr Trp His Gly Thr Phe Pro Ile Asn Ala Tyr Thr Thr Gly
                 85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
            115                 120                 125

Tyr Val Thr Gly Met Thr Thr Asp Asn Val Lys Cys Pro Cys Gln Val
        130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Ser Leu Ala Ser Ser Ser Ala Ser Gln Leu Tyr Ser Phe Glu Pro Leu
225                 230                 235                 240

Gln Ala Glu Glu Asp Glu Arg Glu Val Ser Val Pro Ala Glu Ile Leu
                245                 250                 255

Arg Arg Ser Arg Lys Phe Pro Arg Ala Met Pro Ile Trp Ala Arg Pro
            260                 265                 270

Asp Tyr Asn Pro Pro Leu Leu Glu Ser Trp Lys Asp Pro Asp Tyr Val
        275                 280                 285

Pro Pro Val Val His Gly Cys Pro Leu Pro Pro Ala Lys Ala Pro Pro
    290                 295                 300

Ile Pro Pro Pro Arg Arg Lys Arg Thr Val Val Leu Ser Glu Ser Thr
305                 310                 315                 320

Val Ser Ser Ala Leu Ala Glu Leu Ala Thr Lys Thr Phe Gly Ser Ser
                325                 330                 335

Glu Ser Ser Ala Val Asp Ser Gly Thr Ala Thr Ala Ser Pro Asp Gln
            340                 345                 350

Pro Ser Asp Asp Gly Asp Ala Gly Ser Asp Val Glu Ser Tyr Ser Ser
        355                 360                 365

Met Pro Pro Leu Glu Gly Glu Pro Gly Asp Pro Asp Leu Ser Asp Gly
370                 375                 380

Ser Trp Ser Thr Val Ser Glu Glu Ala Ser Glu Asp Val Val Cys Cys
385                 390                 395                 400

<210> SEQ ID NO 15
<211> LENGTH: 1985
<212> TYPE: PRT
<213> ORGANISM: Hepatitis C virus

<400> SEQUENCE: 15

Met Ala Pro Ile Thr Ala Tyr Ser Gln Gln Thr Arg Gly Leu Leu Gly
 1               5                  10                  15
```

```
Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Arg Ala Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Gly Asp Ser Arg Gly Ser Leu Leu
            115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
            165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
            195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
            245                 250                 255

Val Arg Thr Ile Thr Thr Gly Ala Pro Ile Thr Tyr Ser Thr Tyr Gly
            260                 265                 270

Lys Phe Leu Ala Asp Gly Gly Cys Ser Gly Gly Ala Tyr Asp Ile Ile
            275                 280                 285

Ile Cys Asp Glu Cys His Ser Thr Asp Ser Thr Thr Ile Leu Gly Ile
            290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
            325                 330                 335

Ile Glu Glu Val Ala Leu Ser Ser Thr Gly Glu Ile Pro Phe Tyr Gly
            340                 345                 350

Lys Ala Ile Pro Ile Glu Thr Ile Lys Gly Gly Arg His Leu Ile Phe
            355                 360                 365

Cys His Ser Lys Lys Lys Cys Asp Glu Leu Ala Ala Lys Leu Ser Gly
            370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Ala Thr Asp Ala Leu Met
            405                 410                 415

Thr Gly Phe Thr Gly Asp Phe Asp Ser Val Ile Asp Cys Asn Thr Cys
            420                 425                 430
```

-continued

```
Val Thr Gln Thr Val Asp Phe Ser Leu Asp Pro Thr Phe Thr Ile Glu
        435                 440                 445
Thr Thr Thr Val Pro Gln Asp Ala Val Ser Arg Ser Gln Arg Arg Gly
    450                 455                 460
Arg Thr Gly Arg Gly Arg Met Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Ser Val
            500                 505                 510
Arg Leu Arg Ala Tyr Leu Asn Thr Pro Gly Leu Pro Val Cys Gln Asp
        515                 520                 525
His Leu Glu Phe Trp Glu Ser Val Phe Thr Gly Leu Thr His Ile Asp
    530                 535                 540
Ala His Phe Leu Ser Gln Thr Lys Gln Ala Gly Asp Asn Phe Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
        595                 600                 605
Glu Val Thr Thr Thr His Pro Ile Thr Lys Tyr Ile Met Ala Cys Met
    610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Lys Pro Ala Ile Ile Pro Asp
            660                 665                 670
Arg Glu Val Leu Tyr Arg Glu Phe Asp Glu Met Glu Glu Cys Ala Ser
        675                 680                 685
His Leu Pro Tyr Ile Glu Gln Gly Met Gln Leu Ala Glu Gln Phe Lys
    690                 695                 700
Gln Lys Ala Ile Gly Leu Leu Gln Thr Ala Thr Lys Gln Ala Glu Ala
705                 710                 715                 720
Ala Ala Pro Val Val Glu Ser Lys Trp Arg Thr Leu Glu Ala Phe Trp
                725                 730                 735
Ala Lys His Met Trp Asn Phe Ile Ser Gly Ile Gln Tyr Leu Ala Gly
            740                 745                 750
Leu Ser Thr Leu Pro Gly Asn Pro Ala Ile Ala Ser Leu Met Ala Phe
        755                 760                 765
Thr Ala Ser Ile Thr Ser Pro Leu Thr Thr Gln His Thr Leu Leu Phe
    770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
            820                 825                 830
Gly Val Ala Gly Ala Leu Val Ala Phe Lys Val Met Ser Gly Glu Met
        835                 840                 845
Pro Ser Thr Glu Asp Leu Val Asn Leu Leu Pro Ala Ile Leu Ser Pro
```

```
                850              855              860
Gly Ala Leu Val Val Gly Val Val Cys Ala Ala Ile Leu Arg Arg His
865                  870                  875                  880

Val Gly Pro Gly Glu Gly Ala Val Gln Trp Met Asn Arg Leu Ile Ala
                885                  890                  895

Phe Ala Ser Arg Gly Asn His Val Ser Pro Thr His Tyr Val Pro Glu
            900                  905                  910

Ser Asp Ala Ala Ala Arg Val Thr Gln Ile Leu Ser Ser Leu Thr Ile
        915                  920                  925

Thr Gln Leu Leu Lys Arg Leu His Gln Trp Ile Asn Glu Asp Cys Ser
    930                  935                  940

Thr Pro Cys Ser Gly Ser Trp Leu Arg Asp Val Trp Asp Trp Ile Cys
945                  950                  955                  960

Thr Val Leu Thr Asp Phe Lys Thr Trp Leu Gln Ser Lys Leu Leu Pro
                965                  970                  975

Arg Leu Pro Gly Val Pro Phe Phe Ser Cys Gln Arg Gly Tyr Lys Gly
            980                  985                  990

Val Trp Arg Gly Asp Gly Ile Met Gln Thr Thr Cys Pro Cys Gly Ala
        995                  1000                 1005

Gln Ile Thr Gly His Val Lys Asn Gly Ser Met Arg Ile Val Gly Pro
    1010                 1015                 1020

Arg Thr Cys Ser Asn Thr Trp His Gly Thr Phe Pro Ile Asn Ala Tyr
1025                 1030                 1035                 1040

Thr Thr Gly Pro Cys Thr Pro Ser Pro Ala Pro Asn Tyr Ser Arg Ala
                1045                 1050                 1055

Leu Trp Arg Val Ala Ala Glu Glu Tyr Val Glu Val Thr Arg Val Gly
            1060                 1065                 1070

Asp Phe His Tyr Val Thr Gly Met Thr Thr Asp Asn Val Lys Cys Pro
        1075                 1080                 1085

Cys Gln Val Pro Ala Pro Glu Phe Phe Thr Glu Val Asp Gly Val Arg
    1090                 1095                 1100

Leu His Arg Tyr Ala Pro Ala Cys Lys Pro Leu Leu Arg Glu Glu Val
1105                 1110                 1115                 1120

Thr Phe Leu Val Gly Leu Asn Gln Tyr Leu Val Gly Ser Gln Leu Pro
                1125                 1130                 1135

Cys Glu Pro Glu Pro Asp Val Ala Val Leu Thr Ser Met Leu Thr Asp
            1140                 1145                 1150

Pro Ser His Ile Thr Ala Glu Thr Ala Lys Arg Arg Leu Ala Arg Gly
        1155                 1160                 1165

Ser Pro Pro Ser Leu Ala Ser Ser Ser Ala Ile Gln Leu Ser Ala Pro
    1170                 1175                 1180

Ser Leu Lys Ala Thr Cys Thr Thr Arg His Asp Ser Pro Asp Ala Asp
1185                 1190                 1195                 1200

Leu Ile Glu Ala Asn Leu Leu Trp Arg Gln Glu Met Gly Gly Asn Ile
                1205                 1210                 1215

Thr Arg Val Glu Ser Glu Asn Lys Val Val Ile Leu Asp Ser Phe Glu
            1220                 1225                 1230

Pro Leu Gln Ala Glu Glu Asp Glu Arg Glu Val Ser Val Pro Ala Glu
        1235                 1240                 1245

Ile Leu Arg Arg Ser Arg Lys Phe Pro Arg Ala Met Pro Ile Trp Ala
    1250                 1255                 1260

Arg Pro Asp Tyr Asn Pro Pro Leu Leu Glu Ser Trp Lys Asp Pro Asp
1265                 1270                 1275                 1280
```

-continued

```
Tyr Val Pro Pro Val His Gly Cys Pro Leu Pro Ala Lys Ala
            1285                1290                1295
Pro Pro Ile Pro Pro Arg Arg Lys Arg Thr Val Val Leu Ser Glu
        1300                1305                1310
Ser Thr Val Ser Ser Ala Leu Ala Glu Leu Ala Thr Lys Thr Phe Gly
        1315                1320                1325
Ser Ser Glu Ser Ser Ala Val Asp Ser Gly Thr Ala Thr Ala Ser Pro
        1330                1335                1340
Asp Gln Pro Ser Asp Asp Gly Asp Ala Gly Ser Asp Val Glu Ser Tyr
1345                1350                1355                1360
Ser Ser Met Pro Pro Leu Glu Gly Glu Pro Gly Asp Pro Asp Leu Ser
            1365                1370                1375
Asp Gly Ser Trp Ser Thr Val Ser Glu Glu Ala Ser Glu Asp Val Val
            1380                1385                1390
Cys Cys Ser Met Ser Tyr Thr Trp Thr Gly Ala Leu Ile Thr Pro Cys
            1395                1400                1405
Ala Ala Glu Glu Thr Lys Leu Pro Ile Asn Ala Leu Ser Asn Ser Leu
    1410                1415                1420
Leu Arg His His Asn Leu Val Tyr Ala Thr Thr Ser Arg Ser Ala Ser
1425                1430                1435                1440
Leu Arg Gln Lys Lys Val Thr Phe Asp Arg Leu Gln Val Leu Asp Asp
        1445                1450                1455
His Tyr Arg Asp Val Leu Lys Glu Met Lys Ala Lys Ala Ser Thr Val
            1460                1465                1470
Lys Ala Lys Leu Leu Ser Val Glu Glu Ala Cys Lys Leu Thr Pro Pro
    1475                1480                1485
His Ser Ala Arg Ser Lys Phe Gly Tyr Gly Ala Lys Asp Val Arg Asn
    1490                1495                1500
Leu Ser Ser Lys Ala Val Asn His Ile Arg Ser Val Trp Lys Asp Leu
1505                1510                1515                1520
Leu Glu Asp Thr Glu Thr Pro Ile Asp Thr Thr Ile Met Ala Lys Asn
            1525                1530                1535
Glu Val Phe Cys Val Gln Pro Glu Lys Gly Gly Arg Lys Pro Ala Arg
            1540                1545                1550
Leu Ile Val Phe Pro Asp Leu Gly Val Arg Val Cys Glu Lys Met Ala
        1555                1560                1565
Leu Tyr Asp Val Val Ser Thr Leu Pro Gln Ala Val Met Gly Ser Ser
    1570                1575                1580
Tyr Gly Phe Gln Tyr Ser Pro Gly Gln Arg Val Glu Phe Leu Val Asn
1585                1590                1595                1600
Ala Trp Lys Ala Lys Lys Cys Pro Met Gly Phe Ala Tyr Asp Thr Arg
            1605                1610                1615
Cys Phe Asp Ser Thr Val Thr Glu Asn Asp Ile Arg Val Glu Glu Ser
            1620                1625                1630
Ile Tyr Gln Cys Cys Asp Leu Ala Pro Glu Ala Arg Gln Ala Ile Arg
        1635                1640                1645
Ser Leu Thr Glu Arg Leu Tyr Ile Gly Gly Pro Leu Thr Asn Ser Lys
    1650                1655                1660
Gly Gln Asn Cys Gly Tyr Arg Arg Cys Arg Ala Ser Gly Val Leu Thr
1665                1670                1675                1680
Thr Ser Cys Gly Asn Thr Leu Thr Cys Tyr Leu Lys Ala Ala Ala Ala
            1685                1690                1695
```

```
Cys Arg Ala Ala Lys Leu Gln Asp Cys Thr Met Leu Val Cys Gly Asp
            1700                1705                1710

Asp Leu Val Val Ile Cys Glu Ser Ala Gly Thr Gln Glu Asp Glu Ala
        1715                1720                1725

Ser Leu Arg Ala Phe Thr Glu Ala Met Thr Arg Tyr Ser Ala Pro Pro
    1730                1735                1740

Gly Asp Pro Pro Lys Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
    1795                1800                1805

Tyr Ala Pro Thr Leu Trp Ala Arg Met Ile Leu Met Thr His Phe Phe
1810                1815                1820

Ser Ile Leu Leu Ala Gln Glu Gln Leu Glu Lys Ala Leu Asp Cys Gln
            1825                1830                1835                1840

Ile Tyr Gly Ala Cys Tyr Ser Ile Glu Pro Leu Asp Leu Pro Gln Ile
        1845                1850                1855

Ile Gln Arg Leu His Gly Leu Ser Ala Phe Ser Leu His Ser Tyr Ser
    1860                1865                1870

Pro Gly Glu Ile Asn Arg Val Ala Ser Cys Leu Arg Lys Leu Gly Val
1875                1880                1885

Pro Pro Leu Arg Val Trp Arg His Arg Ala Arg Ser Val Arg Ala Arg
        1890                1895                1900

Leu Leu Ser Gln Gly Gly Arg Ala Ala Thr Cys Gly Lys Tyr Leu Phe
1905                1910                1915                1920

Asn Trp Ala Val Arg Thr Lys Leu Lys Leu Thr Pro Ile Pro Ala Ala
            1925                1930                1935

Ser Gln Leu Asp Leu Ser Ser Trp Phe Val Ala Gly Tyr Ser Gly Gly
        1940                1945                1950

Asp Ile Tyr His Ser Leu Ser Arg Ala Arg Pro Arg Trp Phe Met Trp
    1955                1960                1965

Cys Leu Leu Leu Leu Ser Val Gly Val Gly Ile Tyr Leu Leu Pro Asn
1970                1975                1980

Arg
1985

<210> SEQ ID NO 16
<211> LENGTH: 447
<212> TYPE: PRT
<213> ORGANISM: Hepatitis C virus

<400> SEQUENCE: 16

Ser Gly Ser Trp Leu Arg Asp Val Trp Asp Trp Ile Cys Thr Val Leu
 1               5                  10                  15

Thr Asp Phe Lys Thr Trp Leu Gln Ser Lys Leu Leu Pro Arg Leu Pro
             20                  25                  30

Gly Val Pro Phe Phe Ser Cys Gln Arg Gly Tyr Lys Gly Val Trp Arg
         35                  40                  45

Gly Asp Gly Ile Met Gln Thr Thr Cys Pro Cys Gly Ala Gln Ile Thr
     50                  55                  60

Gly His Val Lys Asn Gly Ser Met Arg Ile Val Gly Pro Arg Thr Cys
 65                  70                  75                  80
```

Ser Asn Thr Trp His Gly Thr Phe Pro Ile Asn Ala Tyr Thr Thr Gly
                        85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
            115                 120                 125

Tyr Val Thr Gly Met Thr Thr Asp Asn Val Lys Cys Pro Cys Gln Val
        130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Ser Leu Ala Ser Ser Ser Ala Ile Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
        275                 280                 285

Ala Glu Glu Asp Glu Arg Glu Val Ser Val Pro Ala Glu Ile Leu Arg
    290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350

Pro Pro Pro Arg Arg Lys Arg Thr Val Val Leu Ser Glu Ser Thr Val
        355                 360                 365

Ser Ser Ala Leu Ala Glu Leu Ala Thr Lys Thr Phe Gly Ser Ser Glu
    370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
        435                 440                 445

<210> SEQ ID NO 17
<211> LENGTH: 1985
<212> TYPE: PRT
<213> ORGANISM: Hepatitis C virus

<400> SEQUENCE: 17

Met Ala Pro Ile Thr Ala Tyr Ser Gln Gln Thr Arg Gly Leu Leu Gly

-continued

```
  1               5                  10                 15
Cys Ile Ile Thr Ser Leu Thr Gly Arg Asp Arg Asn Gln Val Glu Gly
                 20                 25                 30

Glu Val Gln Val Val Ser Thr Ala Thr Gln Ser Phe Leu Ala Thr Cys
                 35                 40                 45

Val Asn Gly Val Cys Trp Thr Val Tyr His Gly Ala Gly Ser Lys Thr
                 50                 55                 60

Leu Ala Gly Pro Lys Gly Pro Ile Thr Gln Met Tyr Thr Asn Val Asp
 65              70                 75                         80

Gln Asp Leu Val Gly Trp Gln Ala Pro Gly Ala Arg Ser Leu Thr
                 85                 90                 95

Pro Cys Thr Cys Gly Ser Ser Asp Leu Tyr Leu Val Thr Arg His Ala
                 100                105                110

Asp Val Ile Pro Val Arg Arg Gly Asp Ser Arg Gly Ser Leu Leu
                 115                120                125

Ser Pro Arg Pro Val Ser Tyr Leu Lys Gly Ser Ser Gly Gly Pro Leu
                 130                135                140

Leu Cys Pro Ser Gly His Ala Val Gly Ile Phe Arg Ala Ala Val Cys
145              150                155                160

Thr Arg Gly Val Ala Lys Ala Val Asp Phe Val Pro Val Glu Ser Met
                 165                170                175

Glu Thr Thr Met Arg Ser Pro Val Phe Thr Asp Asn Ser Ser Pro Pro
                 180                185                190

Ala Val Pro Gln Thr Phe Gln Val Ala His Leu His Ala Pro Thr Gly
                 195                200                205

Ser Gly Lys Ser Thr Lys Val Pro Ala Ala Tyr Ala Ala Gln Gly Tyr
                 210                215                220

Lys Val Leu Val Leu Asn Pro Ser Val Ala Ala Thr Leu Gly Phe Gly
225              230                235                240

Ala Tyr Met Ser Lys Ala His Gly Ile Asp Pro Asn Ile Arg Thr Gly
                 245                250                255

Val Arg Thr Ile Thr Thr Gly Ala Pro Ile Thr Tyr Ser Thr Tyr Gly
                 260                265                270

Lys Phe Leu Ala Asp Gly Gly Cys Ser Gly Gly Ala Tyr Asp Ile Ile
                 275                280                285

Ile Cys Asp Glu Cys His Ser Thr Asp Ser Thr Thr Ile Leu Gly Ile
                 290                295                300

Gly Thr Val Leu Asp Gln Ala Glu Thr Ala Gly Ala Arg Leu Val Val
305              310                315                320

Leu Ala Thr Ala Thr Pro Pro Gly Ser Val Thr Val Pro His Pro Asn
                 325                330                335

Ile Glu Glu Val Ala Leu Ser Ser Thr Gly Glu Ile Pro Phe Tyr Gly
                 340                345                350

Lys Ala Ile Pro Ile Glu Thr Ile Lys Gly Gly Arg His Leu Ile Phe
                 355                360                365

Cys His Ser Lys Lys Lys Cys Asp Glu Leu Ala Ala Lys Leu Ser Gly
                 370                375                380

Leu Gly Leu Asn Ala Val Ala Tyr Tyr Arg Gly Leu Asp Val Ser Val
385              390                395                400

Ile Pro Thr Ser Gly Asp Val Ile Val Ala Thr Asp Ala Leu Met
                 405                410                415

Thr Gly Phe Thr Gly Asp Phe Asp Ser Val Ile Asp Cys Asn Thr Cys
                 420                425                430
```

```
Val Thr Gln Thr Val Asp Phe Ser Leu Asp Pro Thr Phe Thr Ile Glu
            435                 440                 445

Thr Thr Thr Val Pro Gln Asp Ala Val Ser Arg Ser Gln Arg Arg Gly
        450                 455                 460

Arg Thr Gly Arg Gly Arg Met Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Glu Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Thr Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Lys Pro Ala Ile Ile Pro Asp
            660                 665                 670

Arg Glu Val Leu Tyr Arg Glu Phe Asp Glu Met Glu Glu Cys Ala Ser
        675                 680                 685

His Leu Pro Tyr Ile Glu Gln Gly Met Gln Leu Ala Glu Gln Phe Lys
    690                 695                 700

Gln Lys Ala Ile Gly Leu Leu Gln Thr Ala Thr Lys Gln Ala Glu Ala
705                 710                 715                 720

Ala Ala Pro Val Val Glu Ser Lys Trp Arg Thr Leu Glu Ala Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765

Thr Ala Ser Ile Thr Ser Pro Leu Thr Thr Gln His Thr Leu Leu Phe
    770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
        835                 840                 845
```

```
Pro Ser Thr Glu Asp Leu Val Asn Leu Leu Pro Ala Ile Leu Ser Pro
    850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Gly Leu Thr Ile
        915                 920                 925

Thr Gln Leu Leu Lys Arg Leu His Gln Trp Ile Asn Glu Asp Cys Ser
    930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
                965                 970                 975

Arg Leu Pro Gly Val Pro Phe Phe Ser Cys Gln Arg Gly Tyr Lys Gly
            980                 985                 990

Val Trp Arg Gly Asp Gly Ile Met Gln Thr Thr Cys Pro Cys Gly Ala
        995                 1000                1005

Gln Ile Thr Gly His Val Lys Asn Gly Ser Met Arg Ile Val Gly Pro
    1010                1015                1020

Arg Thr Cys Ser Asn Thr Trp His Gly Thr Phe Pro Ile Asn Ala Tyr
1025                1030                1035                1040

Thr Thr Gly Pro Cys Thr Pro Ser Pro Ala Pro Asn Tyr Ser Arg Ala
                1045                1050                1055

Leu Trp Arg Val Ala Ala Glu Glu Tyr Val Glu Val Thr Arg Val Gly
            1060                1065                1070

Asp Phe His Tyr Val Thr Gly Met Thr Thr Asp Asn Val Lys Cys Pro
        1075                1080                1085

Cys Gln Val Pro Ala Pro Glu Phe Phe Thr Glu Val Asp Gly Val Arg
    1090                1095                1100

Leu His Arg Tyr Ala Pro Ala Cys Lys Pro Leu Leu Arg Glu Glu Val
1105                1110                1115                1120

Thr Phe Leu Val Gly Leu Asn Gln Tyr Leu Val Gly Ser Gln Leu Pro
                1125                1130                1135

Cys Glu Pro Glu Pro Asp Val Ala Val Leu Thr Ser Met Leu Thr Asp
            1140                1145                1150

Pro Ser His Ile Thr Ala Glu Thr Ala Lys Arg Gly Leu Ala Arg Gly
        1155                1160                1165

Ser Pro Pro Ser Leu Ala Ser Ser Ser Ala Ser Gln Leu Ser Ala Pro
    1170                1175                1180

Ser Leu Lys Ala Thr Cys Thr Thr Arg His Asp Ser Pro Asp Ala Asp
1185                1190                1195                1200

Leu Ile Glu Ala Asn Leu Leu Trp Arg Gln Glu Met Gly Gly Asn Ile
                1205                1210                1215

Thr Arg Val Glu Ser Glu Asn Lys Val Val Ile Leu Asp Ser Phe Glu
            1220                1225                1230

Pro Leu Gln Ala Glu Glu Asp Glu Arg Glu Val Ser Val Pro Ala Glu
        1235                1240                1245

Ile Leu Arg Arg Ser Arg Lys Phe Pro Arg Ala Met Pro Ile Trp Ala
    1250                1255                1260

Arg Pro Asp Tyr Asn Pro Pro Leu Leu Glu Ser Trp Lys Asp Pro Asp
```

-continued

```
            1265                1270                1275                1280
Tyr Val Pro Pro Val His Gly Cys Pro Leu Pro Pro Ala Lys Ala
                    1285                1290                1295

Pro Pro Ile Pro Pro Pro Arg Arg Lys Arg Thr Val Val Leu Ser Glu
        1300                1305                1310

Ser Thr Val Ser Ser Ala Leu Ala Glu Leu Ala Thr Lys Thr Phe Gly
            1315                1320                1325

Ser Ser Glu Ser Ser Ala Val Asp Ser Gly Thr Ala Thr Ala Ser Pro
        1330                1335                1340

Asp Gln Pro Ser Asp Asp Gly Asp Ala Gly Ser Asp Val Glu Ser Tyr
1345                1350                1355                1360

Ser Ser Met Pro Pro Leu Glu Gly Glu Pro Gly Asp Pro Asp Leu Ser
            1365                1370                1375

Asp Gly Ser Trp Ser Thr Val Ser Glu Glu Ala Ser Glu Asp Val Val
        1380                1385                1390

Cys Cys Ser Met Ser Tyr Thr Trp Thr Gly Ala Leu Ile Thr Pro Cys
            1395                1400                1405

Ala Ala Glu Glu Thr Lys Leu Pro Ile Asn Ala Leu Ser Asn Ser Leu
        1410                1415                1420

Leu Arg His His Asn Leu Val Tyr Ala Thr Thr Ser Arg Ser Ala Ser
1425                1430                1435                1440

Leu Arg Gln Lys Lys Val Thr Phe Asp Arg Leu Gln Val Leu Asp Asp
            1445                1450                1455

His Tyr Arg Asp Val Leu Lys Glu Met Lys Ala Lys Ala Ser Thr Val
        1460                1465                1470

Lys Ala Lys Leu Leu Ser Val Glu Glu Ala Cys Lys Leu Thr Pro Pro
        1475                1480                1485

His Ser Ala Arg Ser Lys Phe Gly Tyr Gly Ala Lys Asp Val Arg Asn
        1490                1495                1500

Leu Ser Ser Lys Ala Val Asn His Ile Arg Ser Val Trp Lys Asp Leu
1505                1510                1515                1520

Leu Glu Asp Thr Glu Thr Pro Ile Asp Thr Thr Ile Met Ala Lys Asn
            1525                1530                1535

Glu Val Phe Cys Val Gln Pro Glu Lys Gly Gly Arg Lys Pro Ala Arg
        1540                1545                1550

Leu Ile Val Phe Pro Asp Leu Gly Val Arg Val Cys Glu Lys Met Ala
            1555                1560                1565

Leu Tyr Asp Val Val Ser Thr Leu Pro Gln Ala Val Met Gly Ser Ser
        1570                1575                1580

Tyr Gly Phe Gln Tyr Ser Pro Gly Gln Arg Val Glu Phe Leu Val Asn
1585                1590                1595                1600

Ala Trp Lys Ala Lys Lys Cys Pro Met Gly Phe Ala Tyr Asp Thr Arg
            1605                1610                1615

Cys Phe Asp Ser Thr Val Thr Glu Asn Asp Ile Arg Val Glu Glu Ser
        1620                1625                1630

Ile Tyr Gln Cys Cys Asp Leu Ala Pro Glu Ala Arg Gln Ala Ile Arg
        1635                1640                1645

Ser Leu Thr Glu Arg Leu Tyr Ile Gly Gly Pro Leu Thr Asn Ser Lys
        1650                1655                1660

Gly Gln Asn Cys Gly Tyr Arg Arg Cys Arg Ala Ser Gly Val Leu Thr
1665                1670                1675                1680

Thr Ser Cys Gly Asn Thr Leu Thr Cys Tyr Leu Lys Ala Ala Ala Ala
            1685                1690                1695
```

Cys Arg Ala Ala Lys Leu Gln Asp Cys Thr Met Leu Val Cys Gly Asp
            1700                1705                1710

Asp Leu Val Val Ile Cys Glu Ser Ala Gly Thr Gln Glu Asp Glu Ala
        1715                1720                1725

Ser Leu Arg Ala Phe Thr Glu Ala Met Thr Arg Tyr Ser Ala Pro Pro
    1730                1735                1740

Gly Asp Pro Pro Lys Pro Glu Tyr Asp Leu Glu Leu Ile Thr Ser Cys
1745                1750                1755                1760

Ser Ser Asn Val Ser Val Ala His Asp Ala Ser Gly Lys Arg Val Tyr
            1765                1770                1775

Tyr Leu Thr Arg Asp Pro Thr Thr Pro Leu Ala Arg Ala Ala Trp Glu
        1780                1785                1790

Thr Ala Arg His Thr Pro Val Asn Ser Trp Leu Gly Asn Ile Ile Met
    1795                1800                1805

Tyr Ala Pro Thr Leu Trp Ala Arg Met Ile Leu Met Thr His Phe Phe
1810                1815                1820

Ser Ile Leu Leu Ala Gln Glu Gln Leu Glu Lys Ala Leu Asp Cys Gln
            1825                1830                1835                1840

Ile Tyr Gly Ala Cys Tyr Ser Ile Glu Pro Leu Asp Leu Pro Gln Ile
        1845                1850                1855

Ile Gln Arg Leu His Gly Leu Ser Ala Phe Ser Leu His Ser Tyr Ser
            1860                1865                1870

Pro Gly Glu Ile Asn Arg Val Ala Ser Cys Leu Arg Lys Leu Gly Val
        1875                1880                1885

Pro Pro Leu Arg Val Trp Arg His Arg Ala Arg Ser Val Arg Ala Arg
    1890                1895                1900

Leu Leu Ser Gln Gly Gly Arg Ala Ala Thr Cys Gly Lys Tyr Leu Phe
1905                1910                1915                1920

Asn Trp Ala Val Arg Thr Lys Leu Lys Leu Thr Pro Ile Pro Ala Ala
            1925                1930                1935

Ser Gln Leu Asp Leu Ser Ser Trp Phe Val Ala Gly Tyr Ser Gly Gly
        1940                1945                1950

Asp Ile Tyr His Ser Leu Ser Arg Ala Arg Pro Arg Trp Phe Met Trp
        1955                1960                1965

Cys Leu Leu Leu Leu Ser Val Gly Val Gly Ile Tyr Leu Leu Pro Asn
    1970                1975                1980

Arg
1985

<210> SEQ ID NO 18
<211> LENGTH: 447
<212> TYPE: PRT
<213> ORGANISM: Hepatitis C virus

<400> SEQUENCE: 18

Ser Gly Ser Trp Leu Arg Asp Val Trp Asp Trp Ile Cys Thr Val Leu
  1               5                  10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
        35                  40                  45

Gly Asp Gly Ile Met Gln Thr Thr Cys Pro Cys Gly Ala Gln Ile Thr
    50                  55                  60

Gly His Val Lys Asn Gly Ser Met Arg Ile Val Gly Pro Arg Thr Cys

```
            65                  70                  75                  80
Ser Asn Thr Trp His Gly Thr Phe Pro Ile Asn Ala Tyr Thr Thr Gly
                        85                  90                  95
Pro Cys Thr Pro Ser Pro Ala Pro Asn Tyr Ser Arg Ala Leu Trp Arg
                    100                 105                 110
Val Ala Ala Glu Glu Tyr Val Glu Val Thr Arg Val Gly Asp Phe His
                115                 120                 125
Tyr Val Thr Gly Met Thr Thr Asp Asn Val Lys Cys Pro Cys Gln Val
            130                 135                 140
Pro Ala Pro Glu Phe Phe Thr Glu Val Asp Gly Val Arg Leu His Arg
145                 150                 155                 160
Tyr Ala Pro Ala Cys Lys Pro Leu Leu Arg Glu Glu Val Thr Phe Leu
                165                 170                 175
Val Gly Leu Asn Gln Tyr Leu Val Gly Ser Gln Leu Pro Cys Glu Pro
            180                 185                 190
Glu Pro Asp Val Ala Val Leu Thr Ser Met Leu Thr Asp Pro Ser His
        195                 200                 205
Ile Thr Ala Glu Thr Ala Lys Arg Gly Leu Ala Arg Gly Ser Pro Pro
    210                 215                 220
Ser Leu Ala Ser Ser Ala Ser Gln Leu Ser Ala Pro Ser Leu Lys
225                 230                 235                 240
Ala Thr Cys Thr Thr Arg His Asp Ser Pro Asp Ala Asp Leu Ile Glu
                245                 250                 255
Ala Asn Leu Leu Trp Arg Gln Glu Met Gly Gly Asn Ile Thr Arg Val
            260                 265                 270
Glu Ser Glu Asn Lys Val Val Ile Leu Asp Ser Phe Glu Pro Leu Gln
        275                 280                 285
Ala Glu Glu Asp Glu Arg Glu Val Ser Val Pro Ala Glu Ile Leu Arg
    290                 295                 300
Arg Ser Arg Lys Phe Pro Arg Ala Met Pro Ile Trp Ala Arg Pro Asp
305                 310                 315                 320
Tyr Asn Pro Pro Leu Leu Glu Ser Trp Lys Asp Pro Asp Tyr Val Pro
                325                 330                 335
Pro Val Val His Gly Cys Pro Leu Pro Pro Ala Lys Ala Pro Pro Ile
            340                 345                 350
Pro Pro Pro Arg Arg Lys Arg Thr Val Val Leu Ser Glu Ser Thr Val
        355                 360                 365
Ser Ser Ala Leu Ala Glu Leu Ala Thr Lys Thr Phe Gly Ser Ser Glu
    370                 375                 380
Ser Ser Ala Val Asp Ser Gly Thr Ala Thr Ala Ser Pro Asp Gln Pro
385                 390                 395                 400
Ser Asp Asp Gly Asp Ala Gly Ser Asp Val Glu Ser Tyr Ser Ser Met
                405                 410                 415
Pro Pro Leu Glu Gly Glu Pro Gly Asp Pro Asp Leu Ser Asp Gly Ser
            420                 425                 430
Trp Ser Thr Val Ser Glu Glu Ala Ser Glu Asp Val Val Cys Cys
        435                 440                 445

<210> SEQ ID NO 19
<211> LENGTH: 447
<212> TYPE: PRT
<213> ORGANISM: Hepatitis C virus

<400> SEQUENCE: 19
```

-continued

```
Ser Gly Ser Trp Leu Arg Asp Val Trp Asp Trp Ile Cys Thr Val Leu
  1               5                  10                  15

Thr Asp Phe Lys Thr Trp Leu Gln Ser Lys Leu Leu Pro Arg Leu Pro
                 20                  25                  30

Gly Val Pro Phe Phe Ser Cys Gln Arg Gly Tyr Lys Gly Val Trp Arg
                 35                  40                  45

Gly Asp Gly Ile Met Gln Thr Thr Cys Pro Cys Gly Ala Gln Ile Thr
             50                  55                  60

Gly His Val Lys Asn Gly Ser Met Arg Ile Val Gly Pro Arg Thr Cys
 65                  70                  75                  80

Ser Asn Thr Trp His Gly Thr Phe Pro Ile Asn Ala Tyr Thr Thr Gly
                 85                  90                  95

Pro Cys Thr Pro Ser Pro Ala Pro Asn Tyr Ser Arg Ala Leu Trp Arg
                100                 105                 110

Val Ala Ala Glu Glu Tyr Val Glu Val Thr Arg Val Gly Asp Phe His
                115                 120                 125

Tyr Val Thr Gly Met Thr Thr Asp Asn Val Lys Cys Pro Cys Gln Val
            130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
                180                 185                 190

Glu Pro Asp Val Ala Val Leu Thr Ser Met Leu Thr Asp Pro Ser His
            195                 200                 205

Ile Thr Ala Glu Thr Ala Lys Arg Arg Leu Ala Arg Gly Ser Pro Pro
210                 215                 220

Ser Leu Ser Ser Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
                260                 265                 270

Glu Ser Glu Asn Lys Val Val Ile Leu Asp Ser Phe Glu Pro Leu Gln
            275                 280                 285

Ala Glu Glu Asp Glu Arg Glu Val Ser Val Pro Ala Glu Ile Leu Arg
            290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
                340                 345                 350

Pro Pro Pro Arg Arg Lys Arg Thr Val Val Leu Ser Glu Ser Thr Val
            355                 360                 365

Ser Ser Ala Leu Ala Glu Leu Ala Thr Lys Thr Phe Gly Ser Ser Glu
370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
```

```
                    420                 425                 430
Trp Ser Thr Val Ser Glu Glu Ala Ser Glu Asp Val Val Cys Cys
        435                 440                 445

<210> SEQ ID NO 20
<211> LENGTH: 447
<212> TYPE: PRT
<213> ORGANISM: Hepatitis C virus

<400> SEQUENCE: 20

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
        35                  40                  45

Gly Asp Gly Ile Met Gln Thr Thr Cys Pro Cys Gly Ala Gln Ile Thr
    50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Cys Leu Ala Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
        275                 280                 285

Ala Glu Glu Asp Glu Arg Glu Val Ser Val Pro Ala Glu Ile Leu Arg
    290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
            340                 345                 350
```

```
Pro Pro Pro Arg Arg Lys Arg Thr Val Val Leu Ser Glu Ser Thr Val
            355                 360                 365

Ser Ser Ala Leu Ala Glu Leu Ala Thr Lys Thr Phe Gly Ser Ser Glu
    370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
            420                 425                 430

Trp Ser Thr Val Ser Glu Glu Ala Ser Glu Asp Val Val Cys Cys
            435                 440                 445

<210> SEQ ID NO 21
<211> LENGTH: 447
<212> TYPE: PRT
<213> ORGANISM: Hepatitis C virus

<400> SEQUENCE: 21

Ser Gly Ser Trp Leu Arg Asp Val Trp Asp Trp Ile Cys Thr Val Leu
1               5                   10                  15

Thr Asp Phe Lys Thr Trp Leu Gln Ser Lys Leu Leu Pro Arg Leu Pro
            20                  25                  30

Gly Val Pro Phe Phe Ser Cys Gln Arg Gly Tyr Lys Gly Val Trp Arg
        35                  40                  45

Gly Asp Gly Ile Met Gln Thr Thr Cys Pro Cys Gly Ala Gln Ile Thr
    50                  55                  60

Gly His Val Lys Asn Gly Ser Met Arg Ile Val Gly Pro Arg Thr Cys
65                  70                  75                  80

Ser Asn Thr Trp His Gly Thr Phe Pro Ile Asn Ala Tyr Thr Thr Gly
                85                  90                  95

Pro Cys Thr Pro Ser Pro Ala Pro Asn Tyr Ser Arg Ala Leu Trp Arg
            100                 105                 110

Val Ala Ala Glu Glu Tyr Val Glu Val Thr Arg Val Gly Asp Phe His
        115                 120                 125

Tyr Val Thr Gly Met Thr Thr Asp Asn Val Lys Cys Pro Cys Gln Val
    130                 135                 140

Pro Ala Pro Glu Phe Phe Thr Glu Val Asp Gly Val Arg Leu His Arg
145                 150                 155                 160

Tyr Ala Pro Ala Cys Lys Pro Leu Leu Arg Glu Glu Val Thr Phe Leu
                165                 170                 175

Val Gly Leu Asn Gln Tyr Leu Val Gly Ser Gln Leu Pro Cys Glu Pro
            180                 185                 190

Glu Pro Asp Val Ala Val Leu Thr Ser Met Leu Thr Asp Pro Ser His
        195                 200                 205

Ile Thr Ala Glu Thr Ala Lys Arg Arg Leu Ala Arg Gly Ser Pro Pro
    210                 215                 220

Pro Leu Ala Ser Ser Ala Ser Gln Leu Ser Ala Pro Ser Leu Lys
225                 230                 235                 240

Ala Thr Cys Thr Thr Arg His Asp Ser Pro Asp Ala Asp Leu Ile Glu
                245                 250                 255

Ala Asn Leu Leu Trp Arg Gln Glu Met Gly Gly Asn Ile Thr Arg Val
            260                 265                 270

Glu Ser Glu Asn Lys Val Val Ile Leu Asp Ser Phe Glu Pro Leu Gln
        275                 280                 285
```

```
Ala Glu Glu Asp Glu Arg Glu Val Ser Val Pro Ala Glu Ile Leu Arg
    290                 295                 300

Arg Ser Arg Lys Phe Pro Arg Ala Met Pro Ile Trp Ala Arg Pro Asp
305                 310                 315                 320

Tyr Asn Pro Pro Leu Leu Glu Ser Trp Lys Asp Pro Asp Tyr Val Pro
                325                 330                 335

Pro Val Val His Gly Cys Pro Leu Pro Pro Ala Lys Ala Pro Pro Ile
                340                 345                 350

Pro Pro Pro Arg Arg Lys Arg Thr Val Val Leu Ser Glu Ser Thr Val
                355                 360                 365

Ser Ser Ala Leu Ala Glu Leu Ala Thr Lys Thr Phe Gly Ser Ser Glu
    370                 375                 380

Ser Ser Ala Val Asp Ser Gly Thr Ala Thr Ala Ser Pro Asp Gln Pro
385                 390                 395                 400

Ser Asp Asp Gly Asp Ala Gly Ser Asp Val Glu Ser Tyr Ser Ser Met
                405                 410                 415

Pro Pro Leu Glu Gly Glu Pro Gly Asp Pro Asp Leu Ser Asp Gly Ser
                420                 425                 430

Trp Ser Thr Val Ser Glu Glu Ala Ser Glu Asp Val Val Cys Cys
                435                 440                 445

<210> SEQ ID NO 22
<211> LENGTH: 7789
<212> TYPE: DNA
<213> ORGANISM: Hepatitis C virus

<400> SEQUENCE: 22
gccagccccc gattgggggc gacactccac catagatcac tccctgtga ggaactactg      60 tcttcacgca gaaagcgtct agccatggcg ttagtatgag tgtcgtgcag cctccaggac    120
cccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
gtgcttgcga gtgccccggg aggtctcgta ccgtgcacac agaccacaa cggtttccct    360 ctagcgggat caattccgcc cctctccctc cccccccct aacgttactg ccgaagccg     420 cttggaataa ggccggtgtg cgtttgtcta tatgttattt tccaccatat tgccgtcttt    480
tggcaatgtg agggcccgga aacctggccc tgtcttcttg acgagcattc ctaggggtct    540
ttcccctctc gccaaaggaa tgcaaggtct gttgaatgtc gtgaaggaag cagttcctct    600
ggaagcttct tgaagacaaa caacgtctgt agcgaccctt gcaggcagc ggaaccccc     660 acctggcgac aggtgcctct gcggccaaaa gccacgtgta taagatacac ctgcaaaggc    720
ggcacaaccc cagtgccacg ttgtgagttg atagttgtg gaaagagtca atggctctc     780 ctcaagcgta ttcaacaagg ggctgaagga tgcccagaag gtaccccatt gtatgggatc    840
tgatctgggg cctcggtgca catgctttac atgtgtttag tcgaggttaa aaaacgtcta    900 ggcccccccga accacgggga cgtggttttc ctttgaaaaa cacgataata ccatggaccg    960
ggagatggca gcatcgtgcg gaggcgcggt tttcgtaggt ctgatactct tgaccttgtc    1020
accgcactat aagctgttcc tcgctaggct catatggtgg ttacaatatt ttatcaccag    1080
ggccgaggca cacttgcaag tgtggatccc ccctcaac gttcgggggg gccgcgatgc     1140
cgtcatcctc ctcacgtgcg cgatccaccc agagctaatc tttaccatca ccaaaatctt    1200
```

```
gctcgccata ctcggtccac tcatggtgct ccaggctggt ataaccaaag tgccgtactt    1260
cgtgcgcgca cacgggctca ttcgtgcatg catgctggtg cggaaggttg ctgggggtca    1320
ttatgtccaa atggctctca tgaagttggc cgcactgaca ggtacgtacg tttatgacca    1380
tctcacccca ctgcgggact gggcccacgc gggcctacga gaccttgcgg tggcagttga    1440
gcccgtcgtc ttctctgata tggagaccaa ggttatcacc tgggggggcag acaccgcggc    1500 gtgtggggac atcatcttgg gcctgcccgt ctccgcccgc aggggagggg agatacatct    1560
gggaccggca gacagccttg aagggcaggg gtggcgactc ctcgcgccta ttacggccta    1620
ctcccaacag acgcgaggcc tacttggctg catcatcact agcctcacag gccgggacag    1680
gaaccaggtc gaggggggagg tccaagtggt ctccaccgca acacaatctt tcctggcgac    1740
ctgcgtcaat ggcgtgtgtt ggactgtcta tcatggtgcc ggctcaaaga cccttgccgg    1800
cccaaagggc ccaatcaccc aaatgtacac caatgtggac caggacctcg tcggctggca    1860
agcgcccccc ggggcgcgtt ccttgacacc atgcacctgc ggcagctcgg acctttactt    1920
ggtcacgagg catgccgatg tcattccggt gcgccggcgg ggcgacagca gggggagcct    1980
actctccccc aggcccgtct cctacttgaa gggctcttcg ggcggtccac tgctctgccc    2040
ctcggggcac gctgtgggca tctttcgggc tgccgtgtgc acccgagggg ttgcgaaggc    2100
ggtggacttt gtaccgtcg agtctatgga aaccactatg cggtcccgg tcttcacgga    2160 caactcgtcc cctccggccg taccgcagac attccaggtg cccatctac acgcccctac    2220 tggtagcggc aagagcacta aggtgccggc tgcgtatgca gcccaagggt ataaggtgct    2280
tgtcctgaac ccgtccgtcg ccgccaccct aggtttcggg gcgtatatgt ctaaggcaca    2340
tggtatcgac cctaacatca gaaccggggt aaggaccatc accacgggtg cccccatcac    2400
gtactccacc tatggcaagt tccttgccga cggtggttgc tctgggggcg cctatgacat    2460
cataatatgt gatgagtgcc actcaactga ctcgaccact atcctgggca tcggcacagt    2520
cctggaccaa gcggagacgg ctggagcgcg actcgtcgtg ctcgccaccg ctacgcctcc    2580
gggatcggtc accgtgccac atccaaacat cgaggaggtg gctctgtcca gcactgagga    2640
aatccccttt tatggcaaag ccatcccccat cgagaccatc aagggggga ggcacctcat    2700 tttctgccat tccaagaaga aatgtgatga gctcgccgcg aagctgtccg gcctcggact    2760
caatgctgta gcatattacc ggggccttga tgtatccgtc ataccaacta gcggagacgt    2820
cattgtcgta gcaacggacg ctctaatgac gggctttacc ggcgatttcg actcagtgat    2880
cgactgcaat acatgtgtca cccagacagt cgacttcagc ctggaccga ccttcaccat    2940 tgagacgacg accgtgccac aagacgcggt gtcacgctcg cagcggcgag gcaggactgg    3000 tagggggcagg atgggcattt acaggtttgt gactccagga gaacgccct cgggcatgtt    3060 cgattcctcg gttctgtgcg agtgctatga cgcgggctgt gcttggtacg agctcacgcc    3120
cgccgagacc tcagttaggt tgcgggctta cctaaacaca ccagggttgc ccgtctgcca    3180
ggaccatctg gagttctggg agagcgtctt tacaggcctc acccacatag acgcccattt    3240
cttgtcccag actaagcagg caggagacaa cttcccctac ctggtagcat accaggctac    3300
ggtgtgcgcc agggctcagg ctccacctcc atcgtgggac caaatgtgga agtgtctcat    3360
acggctaaag cctacgctgc acgggccaac gcccctgctg tataggctgg gagccgttca    3420
aaacgaggtt actaccacac accccataac caaatacatc atggcatgca tgtcggctga    3480
cctggaggtc gtcacgagca cctgggtgct ggtaggcgga gtcctagcag ctctggccgc    3540
gtattgcctg acaacaggca cgtggtcat tgtgggcagg atcatcttgt ccggaaagcc    3600
```

```
ggccatcatt cccgacaggg aagtccttta ccgggagttc gatgagatgg aagagtgcgc   3660
ctcacacctc ccttacatcg aacagggaat gcagctcgcc gaacaattca acagaaggc    3720 aatcgggttg ctgcaaacag ccaccaagca agcggaggc gctgctcccg tggtggaatc    3780
caagtggcgg accctcgaag ccttctgggc gaagcatatg tggaatttca tcagcgggat   3840
acaatattta gcaggcttgt ccactctgcc tggcaacccc gcgatagcat cactgatggc   3900
attcacagcc tctatcacca gcccgctcac cacccaacat accctcctgt taacatcct    3960 gggggatgg gtggccgccc aacttgctcc tcccagcgct gcttctgctt tcgtaggcgc    4020
cggcatcgct ggagcggctg ttggcagcat aggccttggg aaggtgcttg tggatatttt   4080
ggcaggttat ggagcagggg tggcaggcgc gctcgtggcc tttaaggtca tgagcggcga   4140
gatgccctcc accgaggacc tggttaacct actccctgct atcctctccc ctggcgccct   4200
agtcgtcggg gtcgtgtgcg cagcgatact gcgtcggcac gtgggcccag ggagggggc    4260 tgtgcagtgg atgaaccggc tgatagcgtt cgcttcgcgg ggtaaccacg tctcccccac   4320
gcactatgtg cctgagagcg acgctgcagc acgtgtcact cagatcctct ctagtcttac   4380
catcactcag ctgctgaaga ggcttcacca gtggatcaac gaggactgct ccacgccatg   4440
ctccggctcg tggctaagag atgtttggga ttggatatgc acggtgttga ctgatttcaa   4500
gacctggctc cagtccaagc tcctgccgcg attgccggga gtccccttct tctcatgtca   4560
acgtgggtac aagggagtct ggcggggcga cggcatcatg caaaccacct gcccatgtgg   4620
agcacagatc accggacatg tgaaaaacgg ttccatgagg atcgtggggc ctaggacctg   4680
tagtaacacg tggcatggaa cattccccat taacgcgtac accacgggcc cctgcacgcc   4740
ctccccggcg ccaaattatt ctagggcgct gtggcgggtg gctgctgagg agtacgtgga   4800
ggttacgcgg gtgggggatt tccactacgt gacgggcatg accactgaca acgtaaagtg   4860
cccgtgtcag gttccggccc ccgaattctt cacagaagtg gatggggtgc ggttgcacag   4920
gtacgctcca gcgtgcaaac ccctcctacg ggaggaggtc acattcctgg tcgggctcaa   4980
tcaatacctg gttgggtcac agctcccatg cgagcccgaa ccggacgtag cagtgctcac   5040
ttccatgctc accgacccct cccacattac ggcggagacg gctaagcgta ggctggccag   5100
gggatctccc ccctccttgg ccagctcatc agctatccag ctgtctgcgc cttccttgaa   5160
ggcaacatgc actacccgtc atgactcccc ggacgctgac ctcatcgagg ccaacctcct   5220
gtggcggcag gagatgggcg ggaacatcac ccgcgtggag tcagaaaata aggtagtaat   5280
tttggactct ttcgagccgc tccaagcgga ggaggatgag agggaagtat ccgttccggc   5340
ggagatcctg cggaggtcca ggaaattccc tcgagcgatg cccatatggg cacgcccgga   5400
ttacaaccct ccactgttag agtcctggaa ggacccggac tacgtccctc cagtggtaca   5460
cgggtgtcca ttgccgcctg ccaaggcccc tccgatacca cctccacgga ggaagaggac   5520
ggttgtcctg tcagaatcta ccgtgtcttc tgccttggcg gagctcgcca caaagacctt   5580
cggcagctcc gaatcgtcgg ccgtcgacag cggcacggca acggcctctc ctgaccagcc   5640
ctccgacgac ggcgacgcgg gatccgacgt tgagtcgtac tcctccatgc ccccccttga   5700
gggggagccg ggggatcccg atctcagcga cgggtcttgg tctaccgtaa gcaggaggc    5760 tagtgaggac gtcgtctgct gctcgatgtc ctacacatgg acaggcgccc tgatcacgcc   5820
atgcgctgcg gaggaaacca agctgccat caatgcactg agcaactctt tgctccgtca    5880
ccacaacttg gtctatgcta caacatctcg cagcgcaagc ctgcggcaga agaaggtcac   5940
```

```
ctttgacaga ctgcaggtcc tggacgacca ctaccgggac gtgctcaagg agatgaaggc    6000
gaaggcgtcc acagttaagg ctaaacttct atccgtggag gaagcctgta agctgacgcc    6060
cccacattcg gccagatcta aatttggcta tggggcaaag gacgtccgga acctatccag    6120
caaggccgtt aaccacatcc gctccgtgtg gaaggacttg ctggaagaca ctgagacacc    6180
aattgacacc accatcatgg caaaaaatga ggttttctgc gtccaaccag agaaggggg    6240 ccgcaagcca gctcgcctta tcgtattccc agatttgggg gttcgtgtgt gcgagaaaat    6300 ggcccttac gatgtggtct ccaccctccc tcaggccgtg atgggctctt catacggatt    6360
ccaatactct cctggacagc gggtcgagtt cctggtgaat gcctggaaag cgaagaaatg    6420
ccctatgggc ttcgcatatg acacccgctg ttttgactca acggtcactg agaatgacat    6480
ccgtgttgag gagtcaatct accaatgttg tgacttggcc cccgaagcca gacaggccat    6540
aaggtcgctc acagagcggc tttacatcgg ggcccoctg actaattcta aagggcagaa    6600
ctgcggctat cgccggtgcc gcgcgagcgg tgtactgacg accagctgcg gtaatacct    6660 cacatgttac ttgaaggccg ctgcggcctg tcgagctgcg aagctccagg actgcacgat    6720
gctcgtatgc ggagacgacc ttgtcgttat ctgtgaaagc gcggggaccc aagaggacga    6780
ggcgagccta cgggccttca cggaggctat gactagatac tctgccccc ctggggaccc    6840 gcccaaacca gaatacgact ggagttgat aacatcatgc cctccaatg tgtcagtcgc    6900 gcacgatgca tctggcaaaa gggtgtacta tctcacccgt gaccccacca ccccccttgc    6960
gcgggctgcg tggagacag ctagacacac tccagtcaat tcctggctag caacatcat    7020 catgtatgcg cccaccttgt gggcaaggat gatcctgatg actcatttct tctccatcct    7080
tctagctcag gaacaacttg aaaaagccct agattgtcag atctacgggg cctgttactc    7140
cattgagcca cttgacctac ctcagatcat tcaacgactc catggcctta gcgcatttc    7200 actccatagt tactctccag gtgagatcaa tagggtggct tcatgcctca ggaaacttgg    7260
ggtaccgccc ttgcgagtct ggagacatcg gccagaagt gtccgcgcta ggctactgtc    7320 ccagggggg agggctgcca cttgtggcaa gtacctcttc aactgggcag taaggaccaa    7380
gctcaaactc actccaatcc cggctgcgtc ccagttggat ttatccagct ggttcgttgc    7440
tggttacagc gggggagaca tatatcacag cctgtctcgt gcccgacccc gctggttcat    7500
gtggtgccta ctcctacttt ctgtaggggt aggcatctat ctactcccca accgatgaac    7560
ggggacctaa acactccagg ccaataggcc atcctgtttt tttccctttt tttttttctt    7620
tttttttttt tttttttttt tttttttttt ttctcctttt ttttcctct tttttcctt    7680 ttctttcctt tggtggctcc atcttagccc tagtcacggc tagctgtgaa aggtccgtga    7740
gccgcttgac tgcagagagt gctgatactg gcctctctgc agatcaagt               7789
```

<210> SEQ ID NO 23
<211> LENGTH: 11062
<212> TYPE: DNA
<213> ORGANISM: Hepatitis C virus

<400> SEQUENCE: 23

```
gccagccccc gattggggc gacactccac catagatcac tccctgtga ggaactactg      60 tcttcacgca gaaagcgtct agccatgcg ttagtatgaa tgtcgtgcag cctccaggac    120
cccccctccc gggagagcca tagtggtctg cggaaccggt gagtacaccg gaattgccag    180
gacgaccggg tcctttcttg gatcaacccg ctcaatgcct ggagatttgg gcgtgccccc    240
gcgagactgc tagccgagta gtgttgggtc gcgaaaggcc ttgtggtact gcctgatagg    300
```

```
gtgcttgcga gtgccccggg aggtctcgta gaccgtgcac catgagcacg aatcctaaac      360
ctcaaagaaa aaccaaaggg cgcgccatga ttgaacaaga tggattgcac gcaggttctc      420
cggccgcttg ggtggagagg ctattcggct atgactgggc acaacagaca atcggctgct      480
ctgatgccgc cgtgttccgg ctgtcagcgc agggcgcgcc ggttcttttt gtcaagaccg      540
acctgtccgg tgccctgaat gaactgcagg acgaggcagc cgcggctatcg tggctggcca      600 cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg gaagccggtc      840
ttgtcgatca ggatgatctg gacgaagagc atcaggggct cgcgccagcc gaactgttcg      900
ccaggctcaa ggcgcgcatg cccgacgcg aggatctcgt cgtgacccat ggcgatgcct       960
gcttgccgaa tatcatggtg gaaaatggcc gcttttctgg attcatcgac tgtggccggc      1020
tgggtgtggc ggaccgctat caggacatag cgttggctac ccgtgatatt gctgaagagc      1080
ttggcggcga atgggctgac cgcttcctcg tgctttacgg tatcgccgct cccgattcgc      1140
agcgcatcgc cttctatcgc cttcttgacg agttcttctg agtttaaaca gaccacaacg      1200
gtttccctct agcgggatca attccgcccc tctccctccc cccccctaa cgttactggc       1260 cgaagccgct tggaataagg ccggtgtgcg tttgtctata tgttattttc caccatattg      1320
ccgtcttttg gcaatgtgag ggcccggaaa cctggccctg tcttcttgac gagcattcct      1380
aggggtcttt ccctctcgc caaaggaatg caaggtctgt tgaatgtcgt gaaggaagca       1440
gttcctctgg aagcttcttg aagacaaaca acgtctgtag cgacccttg caggcagcgg       1500 aaccccccac ctggcgacag gtgcctctgc ggccaaaagc cacgtgtata agatacacct      1560
gcaaaggcgg cacaacccca gtgccacgtt gtgagttgga tagttgtgga aagagtcaaa      1620
tggctctcct caagcgtatt caacaagggg ctgaaggatg cccagaaggt accccattgt      1680
atgggatctg atctggggcc tcggtgcaca tgctttacat gtgtttagtc gaggttaaaa      1740
aacgtctagg ccccccgaac cacggggacg tggttttcct ttgaaaaaca cgataataat      1800
gagcacgaat cctaaacctc aaagaaaaac caaacgtaac accaaccgcc gcccacagga      1860
cgtcaagttc ccgggcggtg gtcagatcgt cggtggagtt tacctgttgc cgcgcagggg      1920
ccccaggttc ggtgtgcgcg cgactaggaa gacttccgag cggtcgcaac ctcgtggaag      1980
gcgacaacct atccccaagg ctcgccagcc cgagggtagg gcctgggctc agcccgggta      2040
cccctggccc ctctatggca atgagggctt gggtgggca ggatggctcc tgtcaccccg       2100
tggctctcgg cctagttggg gccccacgga ccccggcgt aggtcgcgca atttgggtaa       2160
ggtcatcgat accctcacgt gcggcttcgc cgatctcatg gggtacattc cgctcgtcgg      2220
cgccccccta gggggcgctg ccagggccct ggcgcatggc gtccgggttc tggaggacgg      2280
cgtgaactat gcaacaggga atctgcccgg ttgctccttt tctatcttcc ttttggcttt      2340
gctgtcctgt ttgaccatcc cagcttccgc ttatgaagtg cgcaacgtat ccggagtgta      2400
ccatgtcacg aacgactgct ccaacgcaag cattgtgtat gaggcagcgg acatgatcat      2460 gcatacccc gggtgcgtgc cctgcgttcg ggagaacaac tcctcccgct gctgggtagc       2520
gctcactccc acgctcgcgg ccaggaacgc tagcgtcccc actacgacga tacgacgcca      2580
tgtcgatttg ctcgttgggg cggctgctct ctgctccgct atgtacgtgg gagatctctg      2640
```

```
cggatctgtt ttcctcgtcg cccagctgtt caccttctcg cctcgccggc acgagacagt   2700
acaggactgc aattgctcaa tatatcccgg ccacgtgaca ggtcaccgta tggcttggga   2760
tatgatgatg aactggtcac ctacagcagc cctagtggta tcgcagttac tccggatccc   2820
acaagctgtc gtggatatgg tggcgggggc ccattgggga gtcctagcgg gccttgccta   2880
ctattccatg gtggggaact gggctaaggt tctgattgtg atgctactct ttgccggcgt   2940
tgacggggga acctatgtga caggggggac gatggccaaa acaccctcg ggattacgtc    3000
cctcttttca cccgggtcat cccagaaaat ccagcttgta acaccaacg gcagctggca    3060
catcaacagg actgccctga actgcaatga ctccctcaac actgggttcc ttgctgcgct   3120
gttctacgtg cacaagttca actcatctgg atgcccagag cgcatggcca gctgcagccc   3180
catcgacgcg ttcgctcagg ggtggggggcc catcacttac aatgagtcac acagctcgga  3240
ccagaggcct tattgttggc actacgcacc ccggccgtgc ggtatcgtac ccgcggcgca   3300
ggtgtgtggt ccagtgtact gcttcacccc aagccctgtc gtggtgggga cgaccgaccg   3360
gttcggcgtc cctacgtaca gttgggggga gaatgagacg gacgtgctgc ttcttaacaa   3420
cacgcggccg ccgcaaggca actggttttgg ctgtacatgg atgaatagca ctgggttcac  3480
caagacgtgc gggggccccc cgtgtaacat cgggggggatc ggcaataaaa ccttgacctg  3540
ccccacggac tgcttccgga agcaccccga ggccacttac accaagtgtg ttcggggcc    3600
ttggttgaca cccagatgct tggtccacta cccatacagg ctttggcact acccctgcac   3660
tgtcaacttt accatcttca aggttaggat gtacgtgggg ggagtggagc acaggctcga   3720
agccgcatgc aattggactc gaggagagcg ttgtaacctg gaggacaggg acagatcaga   3780
gcttagcccg ctgctgctgt ctacaacgga gtggcaggta ttgccctgtt ccttcaccac   3840
cctaccggct ctgtccactg gtttgatcca tctccatcag aacgtcgtgg acgtacaata   3900
cctgtacggt atagggtcgg cggttgtctc ctttgcaatc aaatgggagt atgtcctgtt   3960
gctcttcctt cttctggcgg acgcgcgcgt ctgtgcctgc ttgtggatga tgctgctgat   4020
agctcaagct gaggccgccc tagagaacct ggtggtcctc aacgcggcat ccgtggccgg   4080
ggcgcatggc attctctcct tcctcgtgtt cttctgtgct gcctggtaca tcaagggcag   4140
gctggtccct ggggcggcat atgccctcta cggcgtatgg ccgctactcc tgctcctgct   4200
ggcgttacca ccacgagcat acgccatgga ccgggagatg gcagcatcgt gcggaggcgc   4260
ggttttcgta ggtctgatac tcttgacctt gtcaccgcac tataagctgt tcctcgctag   4320
gctcatatgg tggttacaat attttatcac cagggccgag gcacacttgc aagtgtggat   4380
cccccccctc aacgttcggg ggggccgcga tgccgtcatc ctcctcacgt gcgcgatcca   4440
cccagagcta atctttacca tcaccaaaat cttgctcgcc atactcggtc cactcatggt   4500
gctccaggct ggtataacca aagtgccgta cttcgtgcgc gcacacgggc tcattcgtgc   4560
atgcatgctg gtgcggaagg ttgctggggg tcattatgtc caaatggctc tcatgaagtt   4620
ggccgcactg acaggtacgt acgtttatga ccatctcacc ccactgcggg actgggccca   4680
cgcgggccta cgagaccttg cggtggcagt tgagcccgtc gtcttctctg atatggagac   4740
caaggttatc acctgggggg cagacaccgc ggcgtgtggg gacatcatct tgggcctgcc   4800
cgtctccgcc gcaggggga gggagataca tctgggaccg gcagacagcc ttgaagggca   4860
ggggtggcga ctcctcgcgc ctattacggc ctactcccaa cagacgcgag gcctacttgg   4920
ctgcatcatc actagcctca caggccggga caggaaccag gtcgagggg aggtccaagt    4980
ggtctccacc gcaacacaat cttttcctggc gacctgcgtc aatggcgtgt gttggactgt   5040
```

```
ctatcatggt gccggctcaa agacccttgc cggcccaaag ggcccaatca cccaaatgta    5100
caccaatgtg gaccaggacc tcgtcggctg gcaagcgccc cccggggcgc gttccttgac    5160
accatgcacc tgcggcagct cggaccttta cttggtcacg aggcatgccg atgtcattcc    5220
ggtgcgccgg cggggcgaca gcaggggag cctactctcc cccaggcccg tctcctactt    5280
gaagggctct tcgggcggtc cactgctctg cccctcgggg cacgctgtgg gcatctttcg    5340
ggctgccgtg tgcacccgag gggttgcgaa ggcggtggac tttgtacccg tcgagtctat    5400
ggaaaccact atgcggtccc cggtcttcac ggacaactcg tccctccgg ccgtaccgca    5460 gacattccag gtggcccatc tacacgcccc tactggtagc ggcaagagca ctaaggtgcc    5520
ggctgcgtat gcagcccaag ggtataaggt gcttgtcctg aacccgtccg tcgccgccac    5580
cctaggtttc ggggcgtata tgtctaaggc acatggtatc gaccctaaca tcagaaccgg    5640
ggtaaggacc atcaccacgg gtgcccccat cacgtactcc acctatggca agtttcttgc    5700
cgacggtggt tgctctgggg gcgcctatga catcataata tgtgatgagt gccactcaac    5760
tgactcgacc actatcctgg gcatcggcac agtcctggac caagcggaga cggctggagc    5820
gcgactcgtc gtgctcgcca ccgctacgcc tccgggatcg gtcaccgtgc cacatccaaa    5880
catcgaggag gtggctctgt ccagcactgg agaaatcccc ttttatggca aagccatccc    5940
catcgagacc atcaagggg ggaggcacct cattttctgc cattccaaga gaaatgtga    6000 tgagctcgcc gcgaagctgt ccggcctcgg actcaatgct gtagcatatt accggggcct    6060
tgatgtatcc gtcataccaa ctagcggaga cgtcattgtc gtagcaacgg acgctctaat    6120
gacgggcttt accggcgatt tcgactcagt gatcgactgc aatacatgtg tcacccagac    6180
agtcgacttc agcctggacc cgaccttcac cattgagacg acgaccgtgc acaagacgc    6240 ggtgtcacgc tcgcagcggc gaggcaggac tggtaggggc aggatgggca tttacaggtt    6300
tgtgactcca ggagaacggc cctcgggcat gttcgattcc tcggttctgt gcgagtgcta    6360
tgacgcgggc tgtgcttggt acgagctcac gcccgccgag acctcagtta ggttgcgggc    6420
ttacctaaac acaccagggt tgcccgtctg ccaggaccat ctggagttct gggagagcgt    6480
ctttacaggc ctcacccaca tagacgccca tttcttgtcc cagactaagc aggcaggaga    6540
caacttcccc tacctggtag cataccaggc tacggtgtgc gccagggctc aggctccacc    6600
tccatcgtgg gaccaaatgt ggaagtgtct catacggcta aagcctacgc tgcacgggcc    6660
aacgcccctg ctgtataggc tgggagccgt tcaaaacgag gttactacca cacacccat    6720 aaccaaatac atcatggcat gcatgtcggc tgacctggag gtcgtcacga gcacctgggt    6780
gctggtaggc ggagtcctag cagctctggc cgcgtattgc ctgacaacag gcagcgtggt    6840
cattgtgggc aggatcatct tgtccggaaa gccggccatc attcccgaca gggaagtcct    6900
ttaccgggag ttcgatgaga tggaagagtg cgcctcacac ctcccttaca tcgaacaggg    6960
aatgcagctc gccgaacaat tcaaacagaa ggcaatcggg ttgctgcaaa cagccaccaa    7020
gcaagcggag gctgctgctc ccgtggtgga atccaagtgg cggaccctcg aagccttctg    7080
ggcgaagcat atgtggaatt tcatcagcgg gatacaatat ttagcaggct tgtccactct    7140
gcctggcaac cccgcgatag catcactgat ggcattcaca gcctctatca ccagcccgct    7200
caccacccaa cataccctcc tgtttaacat cctgggggga tgggtggccg cccaacttgc    7260
tcctcccagc gctgcttctg ctttcgtagg cgccggcatc gctggagcgg ctgttggcag    7320
cataggcctt gggaaggtgc ttgtggatat tttggcaggt tatggagcag gggtggcagg    7380
```

```
cgcgctcgtg gcctttaagg tcatgagcgg cgagatgccc tccaccgagg acctggttaa   7440
cctactccct gctatcctct cccctggcgc cctagtcgtc ggggtcgtgt gcgcagcgat   7500
actgcgtcgg cacgtgggcc caggggaggg ggctgtgcag tggatgaacc ggctgatagc   7560
gttcgcttcg cggggtaacc acgtctcccc cacgcactat gtgcctgaga gcgacgctgc   7620
agcacgtgtc actcagatcc tctctagtct taccatcact cagctgctga agaggcttca   7680
ccagtggatc aacgaggact gctccacgcc atgctccggc tcgtggctaa gagatgtttg   7740
ggattggata tgcacggtgt tgactgattt caagacctgg ctccagtcca agctcctgcc   7800
gcgattgccg ggagtcccct tcttctcatg tcaacgtggg tacaagggag tctggcgggg   7860
cgacggcatc atgcaaacca cctgcccatg tggagcacag atcaccggac atgtgaaaaa   7920
cggttccatg aggatcgtgg ggcctaggac ctgtagtaac acgtggcatg aacattccc    7980 cattaacgcg tacaccacgg gcccctgcac gccctcccg  gcgccaaatt attctagggc   8040
gctgtggcgg gtggctgctg aggagtacgt ggaggttacg cgggtggggg atttccacta   8100
cgtgacgggc atgaccactg acaacgtaaa gtgcccgtgt caggttccgg cccccgaatt   8160
cttcacagaa gtggatgggg tgcggttgca caggtacgct ccagcgtgca aaccctcct   8220 acgggaggag gtcacattcc tggtcgggct caatcaatac ctggttgggt cacagctccc   8280
atgcgagccc gaaccggacg tagcagtgct cacttccatg ctcaccgacc cctcccacat   8340
tacggcggag acggctaagc gtaggctggc caggggatct ccccctcct tggccagctc    8400 atcagctatc cagctgtctg cgccttcctt gaaggcaaca tgcactaccc gtcatgactc   8460
cccggacgct gacctcatcg aggccaacct cctgtggcgg caggagatgg gcgggaacat   8520
cacccgcgtg gagtcagaaa ataaggtagt aattttggac tctttcgagc cgctccaagc   8580
ggaggaggat gagagggaag tatccgttcc ggcggagatc ctgcggaggt ccaggaaatt   8640
ccctcgagcg atgcccatat gggcacgccc ggattacaac cctccactgt tagagtcctg   8700
gaaggacccg gactacgtcc ctccagtggt acacgggtgt ccattgccgc ctgccaaggc   8760
ccctccgata ccacctccac ggaggaagag gacggttgtc ctgtcagaat ctaccgtgtc   8820
ttctgccttg gcggagctcg ccacaaagac cttcggcagc tccgaatcgt cggccgtcga   8880
cagcggcacg gcaacggcct ctcctgacca gccctccgac gacggcgacg cgggatccga   8940
cgttgagtcg tactcctcca tgccccccct tgagggggag ccggggatc  ccgatctcag   9000 cgacgggtct tggtctaccg taagcgagga ggctagtgag gacgtcgtct gctgctcgat   9060
gtcctacaca tggacaggcg ccctgatcac gccatgcgct gcggaggaaa ccaagctgcc   9120
catcaatgca ctgagcaact ctttgctccg tcaccacaac ttggtctatg ctacaacatc   9180
tcgcagcgca agcctgcggc agaagaaggt cacctttgac agactgcagg tcctggacga   9240
ccactaccgg gacgtgctca aggagatgaa ggcgaaggcg tccacagtta aggctaaact   9300
tctatccgtg gaggaagcct gtaagctgac gccccacat  tcggccagat ctaaatttgg   9360
ctatggggca aaggacgtcc ggaacctatc cagcaaggcc gttaaccaca tccgctccgt   9420
gtggaaggac ttgctggaag acactgagac accaattgac accaccatca tggcaaaaaa   9480
tgaggttttc tgcgtccaac cagagaaggg gggccgcaag ccagctcgcc ttatcgtatt   9540
cccagatttg ggggttcgtg tgtgcgagaa aatggccctt tacgatgtgg tctccaccct   9600
ccctcaggcc gtgatgggct cttcatacgg attccaatac tctcctggac agcgggtcga   9660
gttcctggtg aatgcctgga agcgaagaa  atgcccatg  ggcttcgcat atgacacccg   9720
ctgttttgac tcaacggtca ctgagaatga catccgtgtt gaggagtcaa tctaccaatg   9780
```

-continued

```
ttgtgacttg gccccccgaag ccagacaggc cataaggtcg ctcacagagc ggctttacat      9840 cggggggcccc ctgactaatt ctaaagggca gaactgcggc tatcgccggt gccgcgcgag      9900
cggtgtactg acgaccagct gcggtaatac cctcacatgt tacttgaagg ccgctgcggc      9960
ctgtcgagct gcgaagctcc aggactgcac gatgctcgta tgcggagacg accttgtcgt     10020
tatctgtgaa agcgcgggga cccaagagga cgaggcgagc ctacgggcct tcacggaggc     10080
tatgactaga tactctgccc cccctgggga cccgcccaaa ccagaatacg acttggagtt     10140
gataacatca tgctcctcca atgtgtcagt cgcgcacgat gcatctggca aaagggtgta     10200
ctatctcacc cgtgacccca ccaccccccct tgcgcgggct gcgtgggaga cagctagaca    10260
cactccagtc aattcctggc taggcaacat catcatgtat gcgcccacct tgtgggcaag     10320
gatgatcctg atgactcatt tcttctccat ccttctagct caggaacaac ttgaaaaagc     10380
cctagattgt cagatctacg gggcctgtta ctccattgag ccacttgacc tacctcagat     10440
cattcaacga ctccatggcc ttagcgcatt ttcactccat agttactctc caggtgagat     10500 caataggggtg gcttcatgcc tcaggaaact tggggtaccg cccttgcgag tctggagaca     10560
tcgggccaga agtgtccgcg ctaggctact gtcccagggg gggagggctg ccacttgtgg     10620
caagtacctc ttcaactggg cagtaaggac caagctcaaa ctcactccaa tcccggctgc     10680
gtcccagttg gatttatcca gctggttcgt tgctggttac agcgggggag acatatatca     10740
cagcctgtct cgtgcccgac cccgctggtt catgtggtgc ctactcctac tttctgtagg     10800
ggtaggcatc tatctactcc ccaaccgatg aacgggggacc taaacactcc aggccaatag     10860
gccatcctgt ttttttccct ttttttttt cttttttttt ttttttttt ttttttttt        10920 ttttctcct tttttttcc tcttttttc cttttcttttc ctttggtggc tccatcttag        10980
ccctagtcac ggctagctgt gaaaggtccg tgagccgctt gactgcagag agtgctgata     11040
ctggcctctc tgcagatcaa gt                                              11062
```

<210> SEQ ID NO 24
<211> LENGTH: 9605
<212> TYPE: DNA
<213> ORGANISM: Hepatitis C virus

<400> SEQUENCE: 24

```
gccagccccc gattgggggc gacactccac catagatcac tcccctgtga ggaactactg       60
tcttcacgca gaaagcgtct agccatggcg ttagtatgag tgtcgtgcag cctccaggac      120
cccccctccc gggagagcca tagtggtctg cggaaccggt gagtacaccg gaattgccag      180
gacgaccggg tcctttcttg gatcaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaacgt aacaccaacc gccgcccaca ggacgtcaag ttcccgggcg      420
gtggtcagat cgtcggtgga gtttaccgt tgccgcgcag gggccccagg ttgggtgtgc       480
gcgcgactag gaagacttcc gagcggtcgc aacctcgtgg aaggcgacaa cctatcccca      540
aggctcgcca gcccgaggt agggcctggg ctcagcccgg gtaccctgg cccctctatg        600 gcaatgaggg cttggggtgg gcaggatggc tcctgtcacc ccgtggctct cggcctagtt      660
ggggccccac ggacccccgg cgtaggtcgc gcaatttggg taaggtcatc gataccctca      720
cgtgcggctt cgccgatctc atggggtaca ttccgctcgt cggcgccccc ctaggggggcg     780
```

```
ctgccagggc cctggcgcat ggcgtccggg ttctggagga cggcgtgaac tatgcaacag      840
ggaatctgcc cggttgctcc tttctatct tccttttggc tttgctgtcc tgtttgacca      900
tcccagcttc cgcttatgaa gtgcgcaacg tatccggagt gtaccatgtc acgaacgact      960
gctccaacgc aagcattgtg tatgaggcag cggacatgat catgcatacc cccgggtgcg     1020
tgccctgcgt tcgggagaac aactcctccc gctgctgggt agcgctcact cccacgctcg     1080
cggccaggaa cgctagcgtc cccactacga cgatacgacg ccatgtcgat ttgctcgttg     1140
gggcggctgc tctctgctcc gctatgtacg tgggagatct ctgcggatct gttttcctcg     1200
tcgcccagct gttcaccttc tcgcctcgcc ggcacgagac agtacaggac tgcaattgct     1260
caatatatcc cggccacgtg acaggtcacc gtatggcttg ggatatgatg atgaactggt     1320
cacctacagc agcccctagtg gtatcgcagt tactccggat cccacaagct gtcgtggata     1380
tggtggcggg ggcccattgg ggagtcctag cgggccttgc ctactattcc atggtgggga     1440
actgggctaa ggttctgatt gtgatgctac tctttgccgg cgttgacggg ggaacctatg     1500
tgacaggggg gacgatggcc aaaaacaccc tcgggattac gtccctcttt tcacccgggt     1560
catcccagaa aatccagctt gtaaacacca acggcagctg gcacatcaac aggactgccc     1620
tgaactgcaa tgactccctc aacactgggt tccttgctgc gctgttctac gtgcacaagt     1680
tcaactcatc tggatgccca gagcgcatgg ccagctgcag ccccatcgac gcgttcgctc     1740
aggggtgggg gcccatcact acaatgagt cacacagctc ggaccagagg ccttattgtt     1800
ggcactacgc accccggccg tgcggtatcg tacccgcggc gcaggtgtgt ggtccagtgt     1860
actgcttcac cccaagccct gtcgtggtgg ggacgaccga ccggttcggc gtccctacgt     1920
acagttgggg ggagaatgag acggacgtgc tgcttcttaa caacacgcgg ccgccgcaag     1980
gcaactggtt tggctgtaca tggatgaata gcactgggtt caccaagacg tgcggggggcc     2040 ccccgtgtaa catcgggggg atcggcaata aaaccttgac ctgccccacg gactgcttcc     2100
ggaagcaccc cgaggccact tacaccaagt gtggttcggg gccttggttg acacccagat     2160
gcttggtcca ctaccatac aggctttggc actaccctg cactgtcaac tttaccatct     2220
tcaaggttag gatgtacgtg ggggagtgg agcacaggct cgaagccgca tgcaattgga     2280
ctcgaggaga gcgttgtaac ctggaggaca gggacagatc agagcttagc ccgctgctgc     2340
tgtctacaac ggagtggcag gtattgccct gttccttcac caccctaccg gctctgtcca     2400 ctggttgat ccatctccat cagaacgtcg tggacgtaca atacctgtac ggtatagggt     2460
cggcggttgt ctcctttgca atcaaatggg agtatgtcct gttgctcttc cttcttctgg     2520
cggacgcgcg cgtctgtgcc tgcttgtgga tgatgctgct gatagctcaa gctgaggccg     2580
ccctagagaa cctggtggtc ctcaacgcgg catccgtggc cggggcgcat ggcattctct     2640
ccttcctcgt gttcttctgt gctgcctggt acatcaaggg caggctggtc cctggggcgg     2700
catatgccct ctacgcgta tggccgctac tcctgctcct gctggcgtta ccaccacgag     2760
catacgccat ggaccgggag atggcagcat cgtgcggagg cgcggttttc gtaggtctga     2820
tactcttgac cttgtcaccg cactataagc tgttcctcgc taggctcata tggtggttac     2880
aatattttat caccagggcc gaggcacact tgcaagtgtg gatccccccc ctcaacgttc     2940
gggggggccg cgatgccgtc atcctcctca cgtgcgcgat ccaccagag ctaatctttta     3000 ccatcaccaa aatcttgctc gccatactcg gtccactcat ggtgctccag gctggtataa     3060
ccaaagtgcc gtacttcgtg cgcgcacacg ggctcattcg tgcatgcatg ctggtgcgga     3120
aggttgctgg gggtcattat gtccaaatgg ctctcatgaa gttggccgca ctgacaggta     3180
```

```
cgtacgttta tgaccatctc accccactgc gggactgggc ccacgcgggc ctacgagacc   3240
ttgcggtggc agttgagccc gtcgtcttct ctgatatgga gaccaaggtt atcacctggg   3300
gggcagacac cgcggcgtgt ggggacatca tcttgggcct gcccgtctcc gcccgcaggg   3360
ggagggagat acatctggga ccggcagaca gccttgaagg cagggggtgg cgactcctcg   3420
cgcctattac ggcctactcc aacagacgc gaggcctact tggctgcatc atcactagcc   3480
tcacaggccg ggacaggaac caggtcgagg gggaggtcca agtggtctcc accgcaacac   3540
aatctttcct ggcgacctgc gtcaatggcg tgtgttggac tgtctatcat ggtgccggct   3600
caaagaccct tgccggccca aagggcccaa tcacccaaat gtacaccaat gtggaccagg   3660
acctcgtcgg ctggcaagcg ccccccgggg cgcgttcctt gacaccatgc acctgcggca   3720
gctcggacct ttacttggtc acgaggcatg ccgatgtcat tccggtgcgc cggcggggcg   3780
acagcagggg gagcctactc tcccccaggc ccgtctccta cttgaagggc tcttcgggcg   3840
gtccactgct ctgcccctcg gggcacgctg tgggcatctt tcgggctgcc gtgtgcaccc   3900 gagggggttgc gaaggcggtg gactttgtac ccgtcgagtc tatggaaacc actatgcggt   3960
ccccggtctt cacggacaac tcgtcccctc cggccgtacc gcagacattc caggtggccc   4020
atctacacgc ccctactggt agcggcaaga gcactaaggt gccggctgcg tatgcagccc   4080
aagggtataa ggtgcttgtc ctgaacccgt ccgtcgccgc caccctaggt ttcggggcgt   4140
atatgtctaa ggcacatggt atcgacccta acatcagaac cggggtaagg accatcacca   4200
cgggtgcccc catcacgtac tccacctatg gcaagtttct tgccgacggt ggttgctctg   4260
ggggcgccta tgacatcata atatgtgatg agtgccactc aactgactcg accactatcc   4320
tgggcatcgg cacagtcctg gaccaagcgg agacggctgg agcgcgactc gtcgtgctcg   4380
ccaccgctac gcctccggga tcggtcaccg tgccacatcc aaacatcgag gaggtggctc   4440
tgtccagcac tggagaaatc ccctttttatg gcaaagccat ccccatcgag accatcaagg   4500
gggggaggca cctcatttc tgccattcca agaagaaatg tgatgagctc gccgcgaagc   4560
tgtccggcct cggactcaat gctgtagcat attaccgggg ccttgatgta tccgtcatac   4620
caactagcgg agacgtcatt gtcgtagcaa cggacgctct aatgacgggc tttaccggcg   4680
atttcgactc agtgatcgac tgcaatacat gtgtcaccca gacagtcgac ttcagcctgg   4740
acccgacctt caccattgag acgacgaccg tgccacaaga cgcggtgtca cgctcgcagc   4800
ggcgaggcag gactggtagg ggcaggatgg gcatttacag gtttgtgact ccaggagaac   4860
ggccctcggg catgttcgat tcctcggttc tgtgcgagtg ctatgacgcg ggctgtgctt   4920
ggtacgagct cacgcccgcc gagacctcag ttaggttgcg ggcttaccta aacacaccag   4980
ggttgcccgt ctgccaggac catctggagt tctgggagag cgtctttaca ggcctcaccc   5040
acatagacgc ccatttcttg tcccagacta agcaggcagg agacaacttc ccctacctgg   5100
tagcatacca ggctacggtg tgcgccaggg ctcaggctcc acctccatcg tgggaccaaa   5160
tgtggaagtg tctcatacgg ctaaagccta cgctgcacgg gccaacgccc ctgctgtata   5220
ggctgggagc cgttcaaaac gaggttacta ccacacaccc cataaccaaa tacatcatgg   5280
catgcatgtc ggctgacctg gaggtcgtca cgagcacctg ggtgctggta ggcggagtcc   5340
tagcagctct ggccgcgtat tgcctgacaa caggcagcgt ggtcattgtg gcaggatca   5400 tcttgtccgg aaagccggcc atcattcccg acagggaagt cctttaccgg gagttcgatg   5460
agatggaaga gtgcgcctca cacctccctt acatcgaaca gggaatgcag ctcgccgaac   5520
```

```
aattcaaaca gaaggcaatc gggttgctgc aaacagccac caagcaagcg gaggctgctg   5580
ctcccgtggt ggaatccaag tggcggaccc tcgaagcctt ctgggcgaag catatgtgga   5640
atttcatcag cgggatacaa tatttagcag gcttgtccac tctgcctggc aacccgcga    5700 tagcatcact gatggcattc acagcctcta tcaccagccc gctcaccacc aacataccc    5760 tcctgtttaa catcctgggg ggatgggtgg ccgcccaact tgctcctccc agcgctgctt   5820
ctgctttcgt aggcgccggc atcgctggag cggctgttgg cagcataggc cttgggaagg   5880
tgcttgtgga tattttggca ggttatggag caggggtggc aggcgcgctc gtggcctta    5940 aggtcatgag cggcgagatg ccctccaccg aggacctggt taacctactc cctgctatcc   6000
tctcccctgg cgccctagtc gtcggggtcg tgtgcgcagc gatactgcgt cggcacgtgg   6060
gcccagggga gggggctgtg cagtggatga accggctgat agcgttcgct cgcggggta    6120 accacgtctc ccccacgcac tatgtgcctg agagcgacgc tgcagcacgt gtcactcaga   6180
tcctctctag tcttaccatc actcagctgc tgaagaggct tcaccagtgg atcaacgagg   6240
actgctccac gccatgctcc ggctcgtggc taagagatgt ttgggattgg atatgcacgg   6300
tgttgactga tttcaagacc tggctccagt ccaagctcct gccgcgattg ccgggagtcc   6360
ccttcttctc atgtcaacgt gggtacaagg gagtctggcg gggcgacggc atcatgcaaa   6420
ccacctgccc atgtggagca cagatcaccg gacatgtgaa aaacggttcc atgaggatcg   6480
tggggcctag gacctgtagt aacacgtggc atggaacatt ccccattaac gcgtacacca   6540
cgggcccctg cacgccctcc ccggcgccaa attattctag ggcgctgtgg cgggtggctg   6600
ctgaggagta cgtggaggtt acgcgggtgg gggatttcca ctacgtgacg gcatgacca    6660 ctgacaacgt aaagtgcccg tgtcaggttc cggcccccga attcttcaca gaagtggatg   6720
gggtgcggtt gcacaggtac gctccagcgt gcaaacccct cctacgggag gaggtcacat   6780
tcctggtcgg gctcaatcaa tacctggttg ggtcacagct cccatgcgag cccgaaccgg   6840
acgtagcagt gctcacttcc atgctcaccg accctcca cattacggcg gagacggcta    6900
agcgtaggct ggccagggga tctcccccct ccttggccag ctcatcagct atccagctgt   6960
ctgcgccttc cttgaaggca acatgcacta cccgtcatga ctccccggac gctgacctca   7020
tcgaggccaa cctcctgtgg cggcaggaga tgggcgggaa catcacccgc gtggagtcag   7080
aaaataaggt agtaattttg gactctttcg agccgctcca agcggaggag gatgagaggg   7140
aagtatccgt tccggcggag atcctgcgga ggtccaggaa attccctcga gcgatgccca   7200
tatgggcacg cccggattac aaccctccac tgttagagtc ctggaaggac ccggactacg   7260
tccctccagt ggtacacggg tgtccattgc cgcctgccaa ggcccctccg ataccacctc   7320
cacggaggaa gaggacggtt gtcctgtcag aatctaccgt gtcttctgcc ttggcggagc   7380
tcgccacaaa gaccttcggc agctccgaat cgtcggccgt cgacagcggc acggcaacgg   7440
cctctcctga ccagccctcc gacgacgcg acgcgggatc cgacgttgag tcgtactcct   7500
ccatgccccc ccttgagggg agccggggg atcccgatct cagcgacggg tcttggtcta   7560
ccgtaagcga ggaggctagt gaggacgtcg tctgctgctc gatgtcctac acatggacag   7620
gcgccctgat cacgccatgc gctgcggagg aaaccaagct gcccatcaat gcactgagca   7680
actctttgct ccgtcaccac aacttggtct atgctacaac atctcgcagc gcaagcctgc   7740
ggcagaagaa ggtcacccttt gacagactgc aggtcctgga cgaccactac cgggacgtgc   7800
tcaaggagat gaaggcgaag gcgtccacag ttaaggctaa acttctatcc gtggaggaag   7860
cctgtaagct gacgccccca cattcggcca gatctaaatt tggctatggg gcaaaggacg   7920
```

-continued

| | |
|---|---|
| tccggaacct atccagcaag gccgttaacc acatccgctc cgtgtggaag gacttgctgg | 7980 |
| aagacactga dacaccaatt gacaccacca tcatggcaaa aaatgaggtt ttctgcgtcc | 8040 |
| aaccagagaa gggggggccgc aagccagctc gccttatcgt attcccagat ttgggggttc | 8100 |
| gtgtgtgcga gaaaatggcc ctttacgatg tggtctccac cctccctcag gccgtgatgg | 8160 |
| gctcttcata cggattccaa tactctcctg gacagcgggt cgagttcctg gtgaatgcct | 8220 |
| ggaaagcgaa gaaatgccct atgggcttcg catatgacac ccgctgtttt gactcaacgg | 8280 |
| tcactgagaa tgacatccgt gttgaggagt caatctacca atgttgtgac ttggcccccg | 8340 |
| aagccagaca ggccataagg tcgctcacag agcggcttta catcgggggc cccctgacta | 8400 |
| attctaaagg gcagaactgc ggctatcgcc ggtgccgcgc gagcggtgta ctgacgacca | 8460 |
| gctgcggtaa taccctcaca tgttacttga aggccgctgc ggcctgtcga gctgcgaagc | 8520 |
| tccaggactg cacgatgctc gtatgcggag acgaccttgt cgttatctgt gaaagcgcgg | 8580 |
| ggacccaaga ggacgaggcg agcctacggg ccttcacgga ggctatgact agatactctg | 8640 |
| cccccccctgg ggacccgccc aaaccagaat acgacttgga gttgataaca tcatgctcct | 8700 |
| ccaatgtgtc agtcgcgcac gatgcatctg gcaaaagggt gtactatctc accgtgacc | 8760 |
| ccaccacccc ccttgcgcgg gctgcgtggg agacagctag acacactcca gtcaattcct | 8820 |
| ggctaggcaa catcatcatg tatgcgccca ccttgtgggc aaggatgatc ctgatgactc | 8880 |
| atttcttctc catccttcta gctcaggaac aacttgaaaa agccctagat tgtcagatct | 8940 |
| acggggcctg ttactccatt gagccacttg acctacctca gatcattcaa cgactccatg | 9000 |
| gccttagcgc attttcactc catagttact ctccaggtga gatcaatagg gtggcttcat | 9060 |
| gcctcaggaa acttgggta ccgcccttgc gagtctggag acatcgggcc agaagtgtcc | 9120 |
| gcgctaggct actgtcccag ggggggaggg ctgccacttg tggcaagtac ctcttcaact | 9180 |
| gggcagtaag gaccaagctc aaactcactc caatcccggc tgcgtcccag ttggatttat | 9240 |
| ccagctggtt cgttgctggt tacagcgggg gagacatata tcacagcctg tctcgtgccc | 9300 |
| gaccccgctg gttcatgtgg tgcctactcc tactttctgt aggggtaggc atctatctac | 9360 |
| tccccaaccg atgaacgggg acctaaacac tccaggccaa taggccatcc tgttttttc | 9420 |
| ccttttttt tttcttttt ttttttttt tttttttt ttttttttct cctttttt | 9480 |
| tcctctttt ttccttttct ttcctttggt ggctccatct tagccctagt cacggctagc | 9540 |
| tgtgaaaggt ccgtgagccg cttgactgca gagagtgctg atactggcct ctctgcagat | 9600 |
| caagt | 9605 |

<210> SEQ ID NO 25
<211> LENGTH: 7139
<212> TYPE: DNA
<213> ORGANISM: Hepatitis C virus

<400> SEQUENCE: 25

| | |
|---|---|
| gccagccccc gattgggggc gacactccac catagatcac tcccctgtga ggaactactg | 60 |
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac cagaccacaa cggtttccct | 360 |

```
ctagcgggat caattccgcc cctctccctc ccccccccct aacgttactg gccgaagccg    420
cttggaataa ggccggtgtg cgtttgtcta tatgttattt tccaccatat tgccgtcttt    480
tggcaatgtg agggcccgga aacctggccc tgtcttcttg acgagcattc ctagggtct     540 ttcccctctc gccaaaggaa tgcaaggtct gttgaatgtc gtgaaggaag cagttcctct    600
ggaagcttct tgaagacaaa caacgtctgt agcgacccctt tgcaggcagc ggaaccccc    660 acctggcgac aggtgcctct gcggccaaaa gccacgtgta taagatacac ctgcaaaggc    720
ggcacaaccc cagtgccacg ttgtgagttg atagttgtg gaaagagtca aatggctctc     780
ctcaagcgta ttcaacaagg ggctgaagga tgcccagaag gtaccccatt gtatgggatc    840
tgatctgggg cctcggtgca catgctttac atgtgtttag tcgaggttaa aaaacgtcta    900
ggccccccga accacgggga cgtggttttc ctttgaaaaa cacgataata ccatggcgcc    960
tattacggcc tactcccaac agacgcgagg cctacttggc tgcatcatca ctagcctcac   1020
aggccgggac aggaaccagg tcgaggggga ggtccaagtg gtctccaccg caacacaatc   1080
tttcctggcg acctgcgtca atggcgtgtg ttggactgtc tatcatggtg ccggctcaaa   1140
gacccttgcc ggcccaaagg gcccaatcac ccaaatgtac accaatgtgg accaggacct   1200
cgtcggctgg caagcgcccc ccggggcgcg ttccttgaca ccatgcacct gcggcagctc   1260
ggacctttac ttggtcacga ggcatgccga tgtcattccg gtgcgccggc ggggcgacag   1320 caggggagc ctactctccc ccaggcccgt ctcctacttg aagggctctt cgggcggtcc    1380
actgctctgc ccctcgggc acgctgtggg catctttcgg gctgccgtgt gcacccgagg    1440
ggttgcgaag gcggtggact ttgtacccgt cgagtctatg gaaaccacta tgcggtcccc   1500
ggtcttcacg gacaactcgt cccctccggc cgtaccgcag acattccagg tggcccatct   1560
acacgcccct actggtagcg gcaagagcac taaggtgccg gctgcgtatg cagcccaagg   1620
gtataaggtg cttgtcctga acccgtccgt cgccgccacc ctaggttcg gggcgtatat    1680 gtctaaggca catggtatcg accctaacat cagaaccggg gtaaggacca tcaccacggg   1740
tgcccccatc acgtactcca cctatggcaa gtttcttgcc gacggtggtt gctctggggg   1800
cgcctatgac atcataatat gtgatgagtg ccactcaact gactcgacca ctatcctggg   1860
catcggcaca gtcctggacc aagcggagac ggctggagcg cgactcgtcg tgctcgccac   1920
cgctacgcct ccgggatcgg tcaccgtgcc acatccaaac atcgaggagg tggctctgtc   1980
cagcactgga gaaatcccct tttatggcaa agccatcccc atcgagacca tcaaggggg    2040 gaggcacctc attttctgcc attccaagaa gaaatgtgat gagctcgccg cgaagctgtc   2100
cggcctcgga ctcaatgctg tagcatatta ccggggcctt gatgtatccg tcataccaac   2160
tagcggagac gtcattgtcg tagcaacgga cgctctaatg acgggctta ccggcgattt    2220 cgactcagtg atcgactgca atacatgtgt cacccagaca gtcgacttca gcctggaccc   2280
gaccttcacc attgagacga cgaccgtgcc acaagacgcg tgtcacgct cgcagcggcg    2340 aggcaggact ggtaggggca ggatgggcat ttacaggttt gtgactccag agaacggcc    2400 ctcgggcatg ttcgattcct cggttctgtg cgagtgctat gacgcgggct gtgcttggta   2460
cgagctcacg cccgccgaga cctcagttag gttgcgggct tacctaaaca caccagggtt   2520 gccccgtctgc caggaccatc tggagttctg ggagagcgtc tttacaggcc tcacccacat   2580
agacgcccat ttcttgtccc agactaagca ggcaggagac aacttcccct acctggtagc   2640
ataccaggct acgtgtgcg ccagggctca ggctccacct ccatcgtggg accaaatgtg    2700
gaagtgtctc atacggctaa agcctacgct gcacgggcca acgcccctgc tgtataggct   2760
```

```
gggagccgtt caaaacgagg ttactaccac acaccccata accaaataca tcatggcatg    2820
catgtcggct gacctggagg tcgtcacgag cacctgggtg ctggtaggcg gagtcctagc    2880
agctctggcc gcgtattgcc tgacaacagg cagcgtggtc attgtgggca ggatcatctt    2940
gtccggaaag ccggccatca ttcccgacag ggaagtcctt taccgggagt tcgatgagat    3000
ggaagagtgc gcctcacacc tcccttacat cgaacaggga atgcagctcg ccgaacaatt    3060
caaacagaag gcaatcgggt tgctgcaaac agccaccaag caagcggagg ctgctgctcc    3120
cgtggtggaa tccaagtggc ggaccctcga agccttctgg gcgaagcata tgtggaattt    3180
catcagcggg atacaatatt tagcaggctt gtccactctg cctggcaacc ccgcgatagc    3240
atcactgatg gcattcacag cctctatcac cagcccgctc accacccaac ataccctcct    3300
gtttaacatc ctgggggatg ggtggccgcc caacttgctc ctcccagcgc tgcttctgct    3360
ttcgtaggcg ccggcatcgc tggagcggct gttggcagca taggccttgg aaggtgctt    3420 gtggatattt tggcaggtta tggagcaggg gtggcaggcg cgctcgtggc ctttaaggtc    3480
atgagcgcga gatgccctcc accgaggacc tggttaacct actccctgct atcctctccc    3540
ctggcgccct agtcgtcggg gtcgtgtgcg cagcgatact gcgtcggcac gtgggcccag    3600 ggagggggc tgtgcagtgg atgaaccggc tgatagcgtt cgcttcgcgg ggtaaccacg    3660
tctcccccac gcactatgtg cctgagagcg acgctgcagc acgtgtcact cagatcctct    3720
ctagtcttac catcactcag ctgctgaaga ggcttcacca gtggatcaac gaggactgct    3780
ccacgccatg ctccggctcg tggctaagag atgtttggga ttggatatgc acggtgttga    3840
ctgatttcaa gacctggctc cagtccaagc tcctgccgcg attgccggga gtccccttct    3900
tctcatgtca acgtgggtac aagggagtct ggcggggcga cggcatcatg caaaccacct    3960
gcccatgtgg agcacagatc accggacatg tgaaaaacgg ttccatgagg atcgtggggc    4020
ctaggacctg tagtaacacg tggcatggaa cattccccat taacgcgtac accacgggcc    4080
cctgcacgcc ctccccggcg ccaaattatt ctagggcgct gtggcgggtg gctgctgagg    4140
agtacgtgga ggttacgcgg gtgggggatt tccactacgt gacgggcatg accactgaca    4200
acgtaaagtg cccgtgtcag gttccggccc ccgaattctt cacagaagtg gatggggtgc    4260
ggttgcacag gtacgctcca gcgtgcaaac ccctcctacg ggaggaggtc acattcctgg    4320
tcgggctcaa tcaatacctg gttgggtcac agctcccatg cgagcccgaa ccggacgtag    4380
cagtgctcac ttccatgctc accgacccct cccacattac ggcggagacg gctaagcgta    4440
ggctggccag gggatctccc ccctccttgg ccagctcatc agctatccag ctgtctgcgc    4500
cttccttgaa ggcaacatgc actacccgtc atgactcccc ggacgctgac ctcatcgagg    4560
ccaacctcct gtggcggcag gagatgggcg gaacatcac ccgcgtggag tcagaaaata    4620
aggtagtaat tttggactct ttcgagccgc tccaagcgga ggaggatgag agggaagtat    4680
ccgttccggc ggagatcctg cggaggtcca ggaaattccc tcgagcgatg cccatatggg    4740
cacgcccgga ttacaaccct ccactgttag agtcctggaa ggaccggac tacgtccctc    4800 cagtggtaca cgggtgtcca ttgccgcctg ccaaggcccc tccgatacca cctccacgga    4860
ggaagaggac ggttgtcctg tcagaatcta ccgtgtcttc tgccttggcg agctcgcca    4920 caaagacctt cggcagctcc gaatcgtcgg ccgtcgacag cggcacggca acggcctctc    4980
ctgaccagcc ctccgacgac ggcgacgcgg gatccgacgt tgagtcgtac tcctccatgc    5040 cccccttga gggggagccg ggggatcccg atctcagcga cgggtcttgg tctaccgtaa    5100
```

-continued

```
gcgaggaggc tagtgaggac gtcgtctgct gctcgatgtc ctacacatgg acaggcgccc   5160
tgatcacgcc atgcgctgcg gaggaaacca agctgcccat caatgcactg agcaactctt   5220
tgctccgtca ccacaacttg gtctatgcta caacatctcg cagcgcaagc ctgcggcaga   5280
agaaggtcac ctttgacaga ctgcaggtcc tggacgacca ctaccgggac gtgctcaagg   5340
agatgaaggc gaaggcgtcc acagttaagg ctaaacttct atccgtggag gaagcctgta   5400
agctgacgcc cccacattcg gccagatcta aatttggcta tggggcaaag gacgtccgga   5460
acctatccag caaggccgtt aaccacatcc gctccgtgtg gaaggacttg ctggaagaca   5520
ctgagacacc aattgacacc accatcatgg caaaaaatga ggttttctgc gtccaaccag   5580
agaagggggg ccgcaagcca gctcgcctta tcgtattccc agatttgggg gttcgtgtgt   5640
gcgagaaaat ggccctttac gatgtggtct ccaccctccc tcaggccgtg atgggctctt   5700
catacggatt ccaatactct cctggacagc gggtcgagtt cctggtgaat gcctggaaag   5760
cgaagaaatg ccctatgggc ttcgcatatg acacccgctg ttttgactca acggtcactg   5820
agaatgacat ccgtgttgag gagtcaatct accaatgttg tgacttggcc cccgaagcca   5880
gacaggccat aaggtcgctc acagagcggc tttacatcgg gggcccccctg actaattcta   5940 aagggcagaa ctgcggctat cgccggtgcc gcgcgagcgg tgtactgacg accagctgcg   6000
gtaataccct cacatgttac ttgaaggccg ctgcggcctg tcgagctgcg aagctccagg   6060
actgcacgat gctcgtatgc ggagacgacc ttgtcgttat ctgtgaaagc gcggggaccc   6120
aagaggacga ggcgagccta cgggccttca cggaggctat gactagatac tctgcccccc   6180
ctggggaccc gcccaaacca gaatacgact tggagttgat aacatcatgc tcctccaatg   6240
tgtcagtcgc gcacgatgca tctggcaaaa gggtgtacta tctcacccgt gaccccacca   6300
ccccccttgc gcgggctgcg tgggagacag ctagacacac tccagtcaat tcctggctag   6360
gcaacatcat catgtatgcg cccaccttgt gggcaaggat gatcctgatg actcatttct   6420
tctccatcct tctagctcag gaacaacttg aaaaagccct agattgtcag atctacgggg   6480
cctgttactc cattgagcca cttgacctac ctcagatcat tcaacgactc catggcctta   6540
gcgcattttc actccatagt tactctccag gtgagatcaa tagggtggct tcatgcctca   6600
ggaaacttgg ggtaccgccc ttgcgagtct ggagacatcg ggccagaagt gtccgcgcta   6660
ggctactgtc ccaggggggg agggctgcca cttgtggcaa gtacctcttc aactgggcag   6720
taaggaccaa gctcaaactc actccaatcc cggctgcgtc ccagttggat ttatccagct   6780
ggttcgttgc tggttacagc gggggagaca tatatcacag cctgtctcgt gcccgacccc   6840
gctggttcat gtggtgccta ctcctacttt ctgtaggggt aggcatctat ctactcccca   6900
accgatgaac ggggacctaa acactccagg ccaataggcc atcctgtttt tttccctttt   6960
tttttttctt tttttttttt tttttttttt tttttttttt ttctcctttt tttttcctct   7020
ttttttcctt ttctttcctt tggtggctcc atcttagccc tagtcacggc tagctgtgaa   7080
aggtccgtga gccgcttgac tgcagagagt gctgatactg gcctctctgc agatcaagt    7139
```